US008158102B2

(12) United States Patent
Demers et al.

(10) Patent No.: US 8,158,102 B2
(45) Date of Patent: Apr. 17, 2012

(54) SYSTEM, DEVICE, AND METHOD FOR MIXING A SUBSTANCE WITH A LIQUID

(75) Inventors: Jason A. Demers, Manchester, NH (US); James D. Dale, Nashua, NH (US); Brian Tracey, Litchfield, NH (US); David W. McGill, Bedford, NH (US); Larry B. Gray, Merrimack, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 516 days.

(21) Appl. No.: 10/696,969

(22) Filed: Oct. 30, 2003

(65) Prior Publication Data

US 2005/0095576 A1 May 5, 2005

(51) Int. Cl.
*B01D 11/00* (2006.01)
*B01F 1/00* (2006.01)

(52) U.S. Cl. .................................................. 423/658.5

(58) Field of Classification Search ............... 366/167.1; 604/403, 411, 415, 416; 435/4; 423/658.5
See application file for complete search history.

(56) References Cited

U.S. PATENT DOCUMENTS

| | | | |
|---|---|---|---|
| 1,133,254 A | 3/1915 | Backus | |
| 1,664,576 A | 4/1928 | Stuart et al. | |
| 1,792,906 A | 2/1931 | Heilos | 251/209 |
| 2,313,551 A | 3/1943 | Hurlbut | 417/387 |
| 2,525,251 A | 10/1950 | Willard | 449/17 |
| 2,526,017 A | 10/1950 | Figg | 251/209 |
| 2,703,055 A | 3/1955 | Veth et al. | 417/205 |
| 2,776,854 A | 1/1957 | Billstrom | 292/256 |
| 2,834,504 A | 5/1958 | Joseph | 220/211 |
| 2,902,253 A | 9/1959 | Page | 251/209 |
| 3,048,121 A | 8/1962 | Sheesley | 417/394 |
| 3,339,956 A | 9/1967 | Bencene | 292/127 |
| 3,449,864 A | 6/1969 | Prost-Dame et al. | 49/477.1 |
| 3,481,076 A | 12/1969 | Bedard | 49/279 |
| 3,540,694 A | 11/1970 | Cornelius | 251/209 |
| 3,570,486 A | 3/1971 | Engelsher et al. | 128/218 |
| 3,722,858 A | 3/1973 | Sugimoto et al. | 251/209 |
| 3,727,882 A | 4/1973 | Burris et al. | 251/209 |
| 3,814,548 A | 6/1974 | Rupp | 417/395 |
| 3,856,338 A | 12/1974 | Johnsson | 292/256 |
| 4,072,934 A | 2/1978 | Hiller et al. | 340/243 |
| 4,073,521 A | 2/1978 | Mena | 292/256.65 |
| 4,093,176 A | 6/1978 | Contastin | 249/167 |
| 4,161,264 A | 7/1979 | Malmgren et al. | 222/135 |
| 4,212,589 A | 7/1980 | Bosio | 417/12 |
| 4,230,300 A | 10/1980 | Wiltse | 251/205 |
| 4,247,018 A | 1/1981 | Credle | 222/1 |
| 4,431,425 A | 2/1984 | Thompson et al. | 604/246 |
| 4,468,219 A | 8/1984 | George et al. | 604/67 |
| 4,479,760 A | 10/1984 | Bilstad et al. | 417/375 |
| 4,479,761 A | 10/1984 | Bilstad et al. | 417/395 |
| 4,479,762 A | 10/1984 | Bilstad et al. | 417/395 |
| 4,576,211 A | 3/1986 | Valentini et al. | 141/329 |
| 4,634,430 A | 1/1987 | Polaschegg | 604/141 |
| 4,648,868 A | 3/1987 | Hardwick et al. | 604/32 |
| 4,650,339 A | 3/1987 | Chetcuti et al. | 366/142 |
| 4,662,540 A | 5/1987 | Schroter | 222/55 |
| 4,662,829 A | 5/1987 | Nehring | 417/395 |
| 4,667,927 A | 5/1987 | Oscarsson | 251/209 |
| 4,696,671 A | 9/1987 | Epstein et al. | 604/67 |
| 4,698,160 A | 10/1987 | Haraguchi | 210/647 |
| 4,718,447 A | 1/1988 | Marshall | 137/268 |
| 4,721,138 A | 1/1988 | Simonazzi | 141/150 |
| 4,778,451 A | 10/1988 | Kamen | 604/67 |
| 4,798,580 A | 1/1989 | DeMeo et al. | 604/60 |
| 4,804,366 A | 2/1989 | Zdeb et al. | 604/85 |
| 4,807,660 A | 2/1989 | Aslanian | 137/382 |
| 4,808,161 A | 2/1989 | Kamen | 604/67 |
| 4,818,186 A | 4/1989 | Pastrone et al. | 417/63 |
| 4,826,482 A | 5/1989 | Kamen | 604/67 |
| 4,828,543 A | 5/1989 | Weiss et al. | 604/609 |
| 4,833,922 A | 5/1989 | Frick et al. | 73/756 |
| 4,850,978 A | 7/1989 | Dudar et al. | 604/201 |
| 4,855,714 A | 8/1989 | Clarkson et al. | 340/521 |
| 4,925,444 A | 5/1990 | Orkin et al. | 604/250 |
| 4,927,198 A | 5/1990 | Fennell et al. | 292/306 |
| 4,976,162 A | 12/1990 | Kamen | 73/865.9 |
| 5,005,604 A | 4/1991 | Aslanian | 137/556 |

(Continued)

FOREIGN PATENT DOCUMENTS

WO    WO 87/06119    10/1987

(Continued)

OTHER PUBLICATIONS

*The International Search Report and the Written Opinion of the International Searching Authority*, International Searching Authority, Jun. 14, 2005, 21 pages.

(Continued)

*Primary Examiner* — Marcela M Cordero Garcia
(74) *Attorney, Agent, or Firm* — Marc J. Gorayeb

(57) ABSTRACT

A system, device, and method for mixing a substance with a liquid pumps the liquid into a container of the substance to produce a solution. The container may be part of a container assembly including a port assembly for coupling with the container to produce an inlet and/or and outlet port for the container. The container assembly may be received within a receiving chamber for causing the coupling. The solution may be permitted to flow out of the outlet port when the solution rises within the container to a level of the outlet port so that the substance is partially diluted before flowing out of the outlet port.

41 Claims, 38 Drawing Sheets

U.S. PATENT DOCUMENTS

| | | | |
|---|---|---|---|
| 5,006,050 A | 4/1991 | Cooke et al. | 417/478 |
| 5,045,068 A | 9/1991 | Kawai et al. | 604/246 |
| 5,051,922 A | 9/1991 | Toral et al. | 364/510 |
| 5,062,774 A | 11/1991 | Kramer et al. | 417/413 |
| 5,069,792 A | 12/1991 | Prince et al. | 210/627 |
| 5,088,515 A | 2/1992 | Kamen | 137/15 |
| 5,098,262 A | 3/1992 | Wecker et al. | 417/479 |
| 5,098,371 A | 3/1992 | Juji et al. | 604/4 |
| 5,113,904 A | 5/1992 | Aslanian | 137/556 |
| 5,116,316 A | 5/1992 | Sertic et al. | 604/83 |
| 5,122,116 A | 6/1992 | Kriesel et al. | 604/89 |
| 5,146,414 A | 9/1992 | McKown et al. | 364/510 |
| 5,150,796 A | 9/1992 | Pierson | 209/370 |
| 5,156,186 A | 10/1992 | Manska | 137/556 |
| 5,167,837 A | 12/1992 | Snodgrass et al. | 210/767 |
| 5,178,182 A | 1/1993 | Kamen | 137/454.2 |
| 5,186,333 A | 2/1993 | Pierson et al. | 209/370 |
| 5,197,787 A | 3/1993 | Matsuda et al. | 303/10 |
| 5,255,072 A | 10/1993 | Mikasa et al. | 356/432 |
| 5,267,956 A | 12/1993 | Beuchat | 604/30 |
| 5,272,646 A | 12/1993 | Farmer | 364/509 |
| 5,279,504 A | 1/1994 | Williams | 417/395 |
| 5,290,076 A | 3/1994 | Smith | 292/25 |
| 5,292,306 A | 3/1994 | Wynkoop et al. | 604/51 |
| 5,294,157 A | 3/1994 | Smith et al. | 292/25 |
| 5,302,093 A | 4/1994 | Owens et al. | 417/474 |
| 5,325,884 A | 7/1994 | Mirel et al. | 137/110 |
| 5,330,426 A | 7/1994 | Kriesel et al. | 604/89 |
| 5,336,053 A | 8/1994 | Wynkoop | 417/53 |
| D350,823 S | 9/1994 | Lanigan | D24/111 |
| 5,350,357 A | 9/1994 | Kamen et al. | 604/29 |
| 5,351,686 A | 10/1994 | Steuer et al. | 600/310 |
| 5,355,890 A | 10/1994 | Aguirre et al. | 128/680 |
| 5,378,126 A | 1/1995 | Abrahamson et al. | 417/479 |
| 5,384,714 A | 1/1995 | Kidd | 702/51 |
| 5,385,540 A | 1/1995 | Abbott et al. | 604/4 |
| 5,401,059 A | 3/1995 | Ferrario | 283/67 |
| 5,408,420 A | 4/1995 | Slocum et al. | 702/51 |
| 5,411,472 A | 5/1995 | Steg et al. | 604/4 |
| 5,421,823 A | 6/1995 | Kamen et al. | 604/28 |
| 5,423,738 A | 6/1995 | Robinson et al. | 604/601 |
| 5,428,527 A | 6/1995 | Niemi | 364/152 |
| 5,429,485 A | 7/1995 | Dodge | 417/442 |
| 5,431,626 A | 7/1995 | Bryant et al. | 604/65 |
| 5,438,510 A | 8/1995 | Bryant et al. | 364/413.11 |
| 5,439,355 A | 8/1995 | Jimison et al. | 417/63 |
| 5,463,228 A | 10/1995 | Krause | 250/577 |
| 5,466,220 A * | 11/1995 | Brenneman | 604/87 |
| 5,474,683 A | 12/1995 | Bryant et al. | 210/646 |
| 5,478,337 A | 12/1995 | Okamoto et al. | 604/413 |
| 5,482,440 A | 1/1996 | Dennehy et al. | 417/63 |
| 5,558,255 A | 9/1996 | Sancoff et al. | 222/189.06 |
| 5,575,310 A | 11/1996 | Kamen et al. | 137/614.11 |
| 5,578,012 A | 11/1996 | Kamen et al. | 604/152 |
| 5,579,244 A | 11/1996 | Brown | 364/558 |
| 5,584,671 A | 12/1996 | Schweitzer, Jr. et al. | 417/298 |
| 5,588,816 A | 12/1996 | Abbott et al. | 417/479 |
| 5,593,290 A | 1/1997 | Greisch et al. | 417/478 |
| 5,628,908 A | 5/1997 | Kamen et al. | 210/646 |
| 5,634,896 A | 6/1997 | Bryant et al. | 604/29 |
| 5,638,737 A | 6/1997 | Mattson et al. | 92/101 |
| 5,647,391 A | 7/1997 | Chan et al. | 366/152.4 |
| 5,649,810 A | 7/1997 | Schweitzer, Jr. et al. | 417/298 |
| 5,651,775 A | 7/1997 | Walker et al. | 604/207 |
| 5,681,285 A | 10/1997 | Ford et al. | 604/151 |
| 5,713,865 A | 2/1998 | Manning et al. | 604/122 |
| 5,716,343 A | 2/1998 | Kriesel et al. | 604/132 |
| 5,755,683 A | 5/1998 | Houle et al. | 604/30 |
| 5,776,103 A | 7/1998 | Kriesel et al. | 604/132 |
| 5,795,328 A | 8/1998 | Barnitz et al. | 604/67 |
| 5,808,181 A | 9/1998 | Wamsiedler et al. | 210/646 |
| 5,816,779 A | 10/1998 | Lawless et al. | 417/63 |
| 5,823,026 A | 10/1998 | Finke | 70/276 |
| 5,837,905 A | 11/1998 | Strauss et al. | 73/861.63 |
| 5,868,162 A | 2/1999 | Dickerson, Jr. | 137/557 |
| 5,879,328 A | 3/1999 | Holmberg et al. | 604/82 |
| 5,883,299 A | 3/1999 | Green et al. | 417/63 |
| 5,935,105 A | 8/1999 | Manning et al. | 604/122 |
| 5,938,634 A | 8/1999 | Packard | 604/29 |
| 5,965,821 A | 10/1999 | Grudzien | 73/724 |
| 5,989,423 A | 11/1999 | Kamen et al. | 210/258 |
| 6,022,483 A | 2/2000 | Aral | 216/59 |
| 6,041,801 A | 3/2000 | Gray et al. | 137/14 |
| 6,065,941 A | 5/2000 | Gray et al. | 417/63 |
| 6,070,761 A | 6/2000 | Bloom et al. | 222/81 |
| 6,109,881 A | 8/2000 | Snodgrass et al. | 417/53 |
| 6,136,586 A | 10/2000 | Budowsky | 435/238 |
| 6,210,361 B1 | 4/2001 | Kamen et al. | 604/82 |
| 6,223,130 B1 | 4/2001 | Gray et al. | 702/51 |
| 6,234,997 B1 | 5/2001 | Kamen et al. | 604/131 |
| 6,245,570 B1 | 6/2001 | Grimm et al. | 436/55 |
| 6,264,458 B1 | 7/2001 | Marcuz et al. | 425/451.9 |
| 6,302,653 B1 | 10/2001 | Bryant et al. | 417/53 |
| 6,343,614 B1 | 2/2002 | Gray et al. | 137/14 |
| 6,364,857 B1 | 4/2002 | Gray et al. | 604/153 |
| 6,382,923 B1 | 5/2002 | Gray | 417/53 |
| 6,416,293 B1 | 7/2002 | Bouchard et al. | 417/53 |
| 6,464,667 B1 | 10/2002 | Kamen et al. | 604/131 |
| 6,485,263 B1 | 11/2002 | Bryant et al. | 417/53 |
| 6,503,062 B1 | 1/2003 | Gray et al. | 417/53 |
| 6,520,747 B2 | 2/2003 | Gray et al. | 417/63 |
| 6,527,758 B2 * | 3/2003 | Ko | 604/403 |
| 6,604,908 B1 | 8/2003 | Bryant et al. | 417/26 |
| 6,610,040 B1 * | 8/2003 | Fowles et al. | 604/413 |
| 6,663,359 B2 | 12/2003 | Gray et al. | 417/383 |
| 7,011,742 B2 | 3/2006 | Rosiello | 210/109 |
| 7,461,968 B2 * | 12/2008 | Demers et al. | 366/152.1 |
| 2001/0024624 A1 * | 9/2001 | Schmidt et al. | 422/104 |
| 2003/0229302 A1 | 12/2003 | Robinson et al. | 604/4.01 |
| 2005/0096583 A1 * | 5/2005 | Demers et al. | 604/15 |

FOREIGN PATENT DOCUMENTS

| | | |
|---|---|---|
| WO | WO 94/22566 | 10/1994 |
| WO | WO 99/10028 | 3/1999 |
| WO | WO 01/18396 A1 | 3/2001 |
| WO | WO 03/086509 A1 | 10/2003 |

OTHER PUBLICATIONS

*The International Search Report and the Written Opinion of the International Searching Authority*, International Searching Authority, Apr. 4, 2005, 13 pages.

*Invitation to Pay Additional Fees/Communication Relating to the Results of the Partial International Search*, International Searching Authority, May 3, 2005, 7 pages.

* cited by examiner

1900

SYSTEM, DEVICE, AND METHOD FOR MIXING A SUBSTANCE WITH A LIQUID

CROSS-REFERENCE TO RELATED APPLICATION(S)

The present application may include subject matter related to one or more of the following commonly-owned United States patent applications, each of which was filed on even date herewith and is hereby incorporated herein by reference in its entirety:

U.S. patent application Ser. No. 10/696,893 entitled SYSTEM, DEVICE, AND METHOD FOR MIXING LIQUIDS (referred to herein as "Application D71");

U.S. patent application Ser. No. 10/696,818 entitled TWO-STAGE MIXING SYSTEM, APPARATUS, AND METHOD (referred to herein as "Application D72");

U.S. patent application Ser. No. 10/697,176 entitled SYSTEM AND METHOD FOR PUMPING FLUID USING A PUMP CASSETTE (referred to herein as "Application D73");

U.S. patent application Ser. No. 10/696,984 entitled DOOR LOCKING MECHANISM (referred to herein as "Application D74");

U.S. patent application Ser. No. 10/697,450 entitled BEZEL ASSEMBLY FOR PNEUMATIC CONTROL (referred to herein as "Application D75");

U.S. patent application Ser. No. 10/697,862 entitled PUMP CASSETTE WITH SPIKING ASSEMBLY (referred to herein as "Application D84"); and U.S. patent application Ser. No. 10/696,990 entitled PUMP CASSETTE BANK (referred to herein as "Application D85").

FIELD OF THE INVENTION

The present invention relates generally to pumping liquids, and more particularly to mixing a substance with a liquid.

BACKGROUND OF THE INVENTION

Millions of people receive blood transfusions each year. Although helpful in many cases, blood transfusions have associated risks. Among others, there is a risk that microorganisms capable of causing disease (i.e., pathogens) could pass from the donor blood to the ultimate blood recipient. For example, untreated blood used in a blood transfusion could have pathogens causing the West Nile Virus, or AIDS. It thus is critical for the public health to ensure that transfused blood is substantially free of pathogens.

The medical community has responded to this need by developing various techniques for removing known and unknown pathogens from donated blood. One technique involves mixing precise amounts of a diluted anti-pathogen compound with blood. Some time after mixing, a rinsing process removes the anti-pathogen compound from the blood. One complexity with this process, however, is the fact that the diluted anti-pathogen compound has a very short shelf life (e.g., on the order of about four hours). Accordingly, the diluted anti-pathogen compound must be produced a relatively short time before it is mixed with blood.

The anti-pathogen compound is not easy to handle before it is diluted. To the contrary, it has a very high pH (e.g., on the order of 11.0 or higher) and thus, is highly caustic and toxic. Mere contact with the undiluted solution can melt plastic, or burn flesh. Because of these undesirable properties, the undiluted solution typically is manually diluted by highly trained laboratory technicians that necessarily must be protected from direct contact with it. Consequently, laboratory technicians often are required to wear relatively impermeable protective gear while diluting the solution behind a chemical laminar flowhood. Such a process, however, is inherently slow, imprecise, and costly due to the multitude of safety requirements. Moreover, even with safeguards, diluting the undiluted solution still poses a risk to the laboratory technician.

SUMMARY OF THE INVENTION

Embodiments of the present invention provide for safely and efficiently mixing a substance with a liquid.

In accordance with one aspect of the invention, the substance is contained in a container assembly having a sealed container that contains the substance. The container assembly is joined with a port assembly within a receiving chamber. The port assembly provides at least an inlet to the container, and typically also an outlet from the container. A liquid is added to the container through the inlet to produce a solution of substance and liquid. Continued ingress of liquid may cause the solution to flow out of the container through the outlet.

In accordance with other aspect of the invention, the substance is a caustic substance that is provided in a primary container having a bottom and a top, with the caustic substance filling the primary container from the bottom to a given point between the bottom and the top. An outlet is provided in the primary container, such that the outlet is between the given point and the top. A predetermined amount of liquid is added to the primary container to produce a combined caustic substance and liquid solution that rises at least to the level of the outlet. At least some of the solution is permitted to flow from the primary container through the outlet after the solution rises to the outlet.

DETAILED DESCRIPTION OF A PREFERRED EMBODIMENT

Embodiments of the present invention provide for safely and efficiently mixing a substance with a liquid. For convenience, this mixing process may be referred to hereinafter as "compounding," and an apparatus that performs such compounding may be referred to hereinafter as a "compounder" or "compounder pump."

In certain embodiments of the present invention, the substance is contained in a container assembly having a sealed container that contains the substance. The container assembly is joined with a port assembly within a receiving chamber. The port assembly provides at least an inlet to the container, and typically also an outlet from the container. A liquid is added to the container through the inlet to produce a solution of substance and liquid. Continued ingress of liquid may cause the solution to flow out of the container through the outlet.

Figure 19:
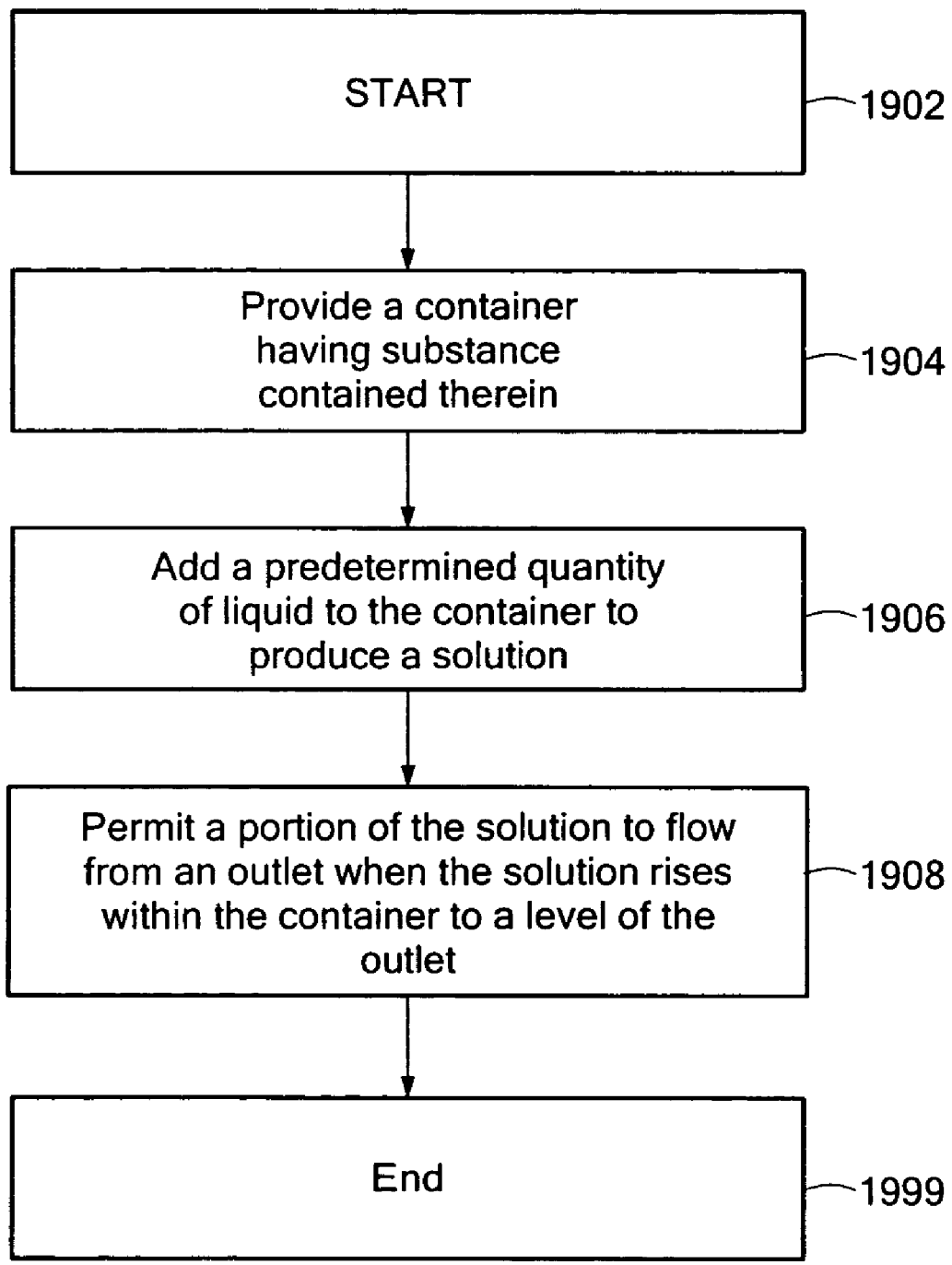
FIG. 19 shows a logic flow diagram showing exemplary logic for mixing a substance with a liquid in accordance with an embodiment of the present invention.

FIG. 19 is a logic flow diagram showing exemplary logic 1900 for mixing a substance with a liquid in accordance with an embodiment of the present invention. Beginning in block 1902, a container having a substance contained therein is provided, in block 1904. A predetermined quantity of a liquid is added to the container to produce a solution, in block 1906. The solution is permitted to flow from an outlet of the container to a receptacle when the solution rises within the container to a level of the outlet, in block 1908. Typically, liquid continues to be added to the container so that the resulting solution in the receptacle reaches has a predetermined concentration of substance to liquid. The logic ends in block 1999.

In certain embodiments of the present invention, the substance is a caustic substance that is provided in a primary container having a bottom and a top, with the caustic substance filling the primary container from the bottom to a given point between the bottom and the top. An outlet is provided in the primary container, such that the outlet is between the given point and the top. A predetermined amount of liquid is added to the primary container to produce a combined caustic substance and liquid solution that rises at least to the level of the outlet. At least some of the solution is permitted to flow from the primary container through the outlet after the solution rises to the outlet.

In exemplary embodiments of the present invention, the substance to be mixed with the liquid is a caustic anti-pathogen compound known as PEN110™ or INACTINE™, which is an organic solvent with a pH over 11 that is distributed by V.I. Technologies, Inc. of Watertown, Mass. Such an anti-pathogen compound can be used to reduce pathogens in a substance such as blood. One problem with such an anti-pathogen compound is that it typically cannot be added directly to the blood (or other substance) targeted for pathogen reduction. Therefore, the anti-pathogen compound is preferably mixed with a buffer solution, such as sodium phosphate, to form a working solution that then can be added to the blood or other substance to reduce pathogens in the blood. Because of the caustic nature of the anti-pathogen compound, the anti-pathogen compound should not come into contact with certain materials, such as plastic tubing commonly used to carry fluids in pump mechanisms. Therefore, in exemplary embodiments of the present invention, mixing is preferably accomplished by pumping the buffer solution into an anti-pathogen compound container through an inlet in order to form a partially diluted solution of anti-pathogen compound and buffer solution. The continued ingress of buffer solution to the anti-pathogen compound container through the inlet causes further dilution and also causes the partially diluted solution to flow out of the anti-pathogen compound container through an outlet to a working solution container. By partially diluting the anti-pathogen compound within the anti-pathogen compound container, the undiluted anti-pathogen compound does not come into contact with anything outside of the anti-pathogen compound container, including human operators, the pump mechanism (including tubing from the anti-pathogen compound container to the working solution container), and the external environment in general. The anti-pathogen compound is typically diluted to a predetermined concentration (e.g., 1 part anti-pathogen compound to 99 parts buffer solution), within predetermined tolerances. The anti-pathogen compound container is preferably sealed following dilution to allow for safe disposal of the anti-pathogen compound container.

System Overview

Figure 1A:
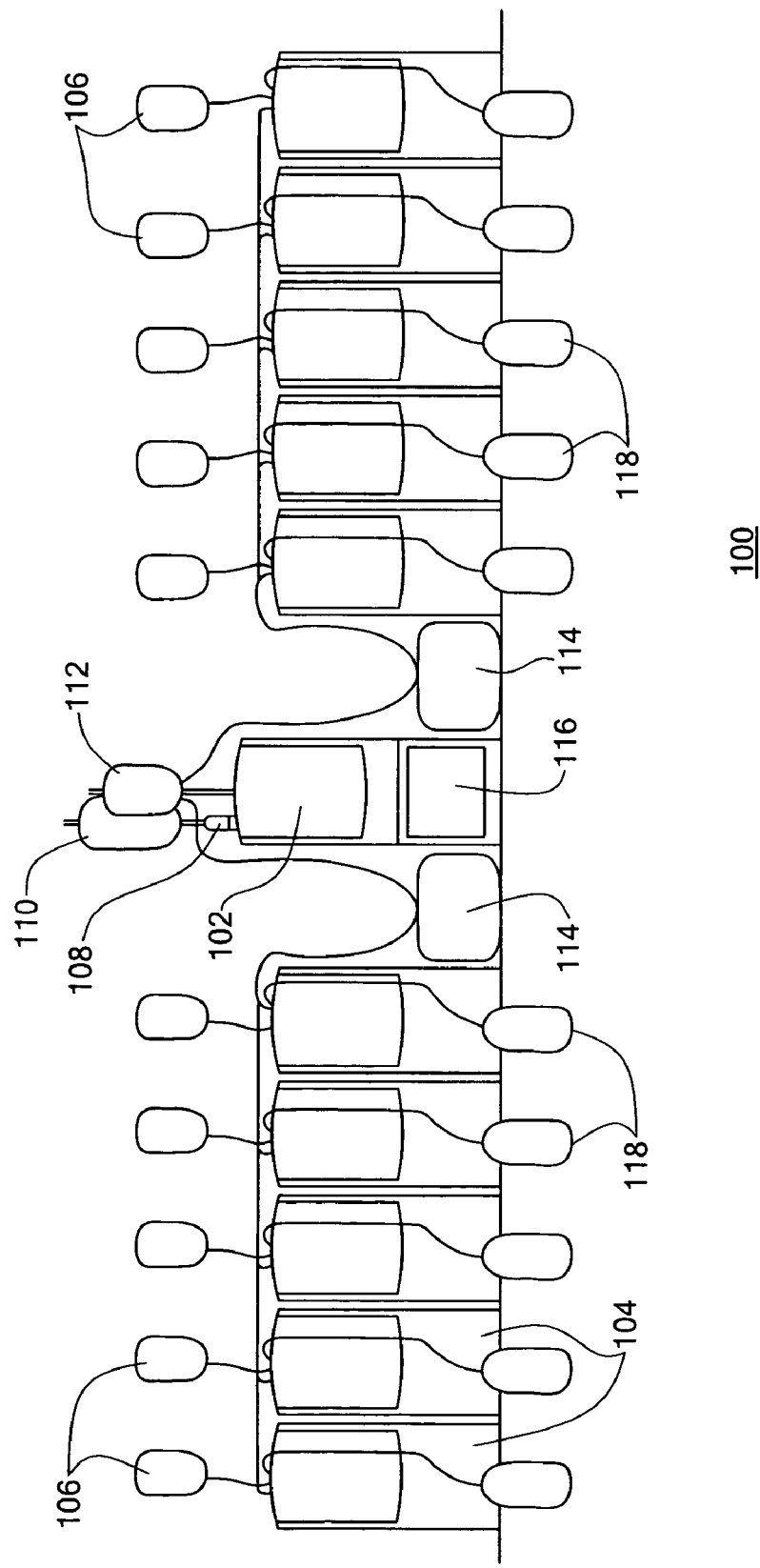
FIG. 1A shows an exemplary blood processing system 100 having a compounder in accordance with an embodiment of the present invention.

FIG. 1A shows an exemplary blood processing system 100 having a compounder in accordance with an embodiment of the present invention. Among other things, the blood processing system 100 includes a single compounder pump 102 and ten essentially identical blood pumps 104 organized as two banks of five blood pumps each. The compounder pump 102 pumps buffer solution from a buffer solution container 110 into a vial of anti-pathogen compound 108. The mixture, referred to as a working solution, is pumped into a working solution container 112. Each of the blood pumps 104 mixes working solution from the working solution container 112 with red blood cell concentrate (RBCC) 106 to form an incubation solution that is pumped into an incubation bag 118. The incubation solution is typically allowed to incubate for some period of time, after which it is rinsed to remove the anti-pathogen compound to produce a pathogen reduced blood product. The blood processing system 100 typically also includes two sterile docks 114 that are used by the operator to splice together plastic tubing as necessary for various blood processing operations. The blood processing system 100 is controlled through a user interface 116.

Figure 1B:
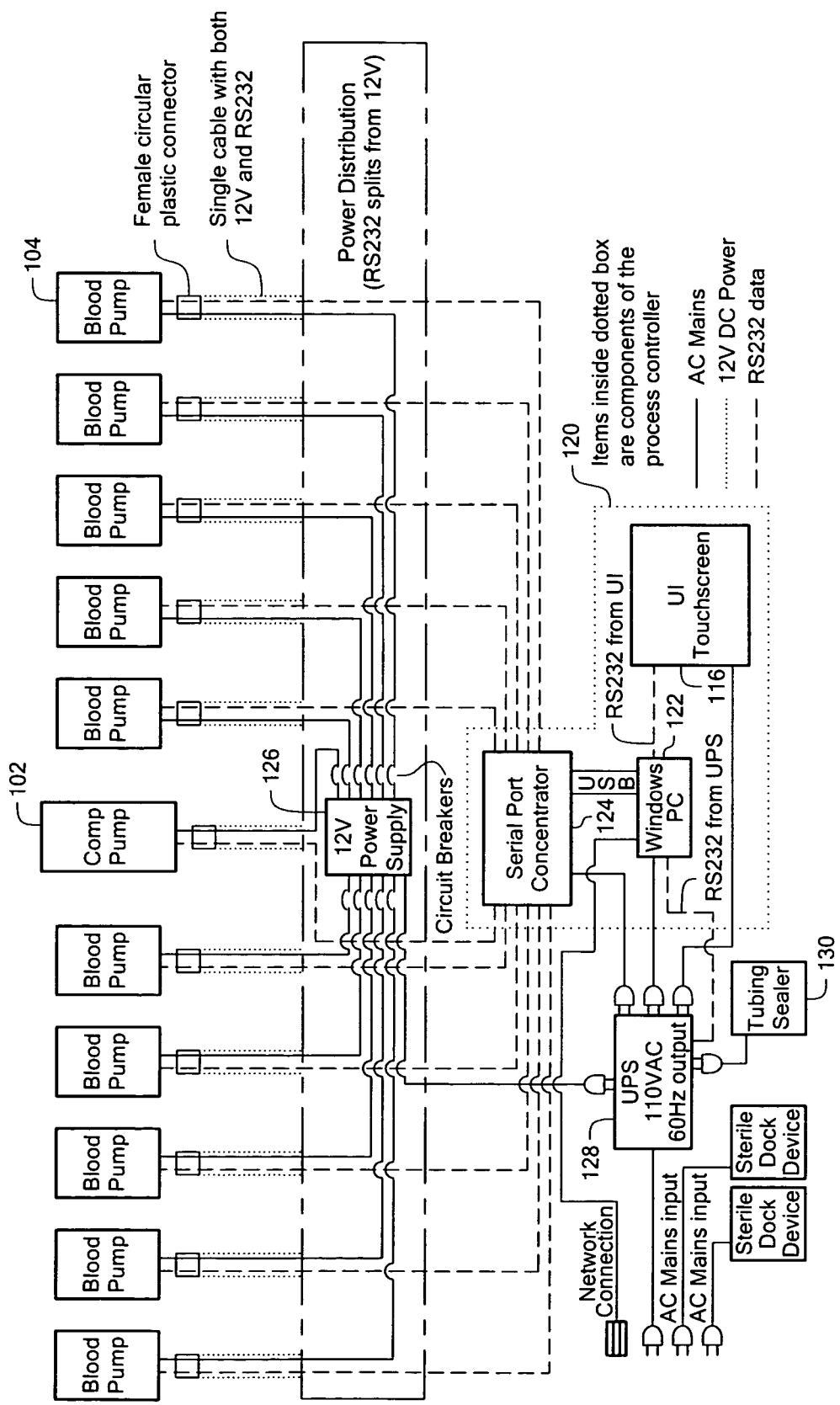
FIG. 1B shows an exemplary wiring diagram for one embodiment of the blood processing system shown in FIG. 1A.

FIG. 1B shows an exemplary wiring diagram for one embodiment of the blood processing system 100. The compounder pump 102 and the blood pumps 104 are typically powered from a common 12-Volt external power supply 126, and are controlled by an external process controller 120. The process controller 120 includes the user interface 116, a computer 122, and a serial port concentrator 124. The compounder pump 102 and the blood pumps 104 are in communication with the process controller 120 through the serial port concentrator 124, for example, over RS-232 communication links. The blood processing system 100 typically includes a tubing sealer 130 for sealing plastic tubing as necessary for various blood processing operations. The blood processing system 100 typically includes an uninterruptible power supply (UPS) 128 for maintaining electrical power to the 12-Volt power supply, the process controller, and other components in the event of a primary power loss.

Figure 1C:
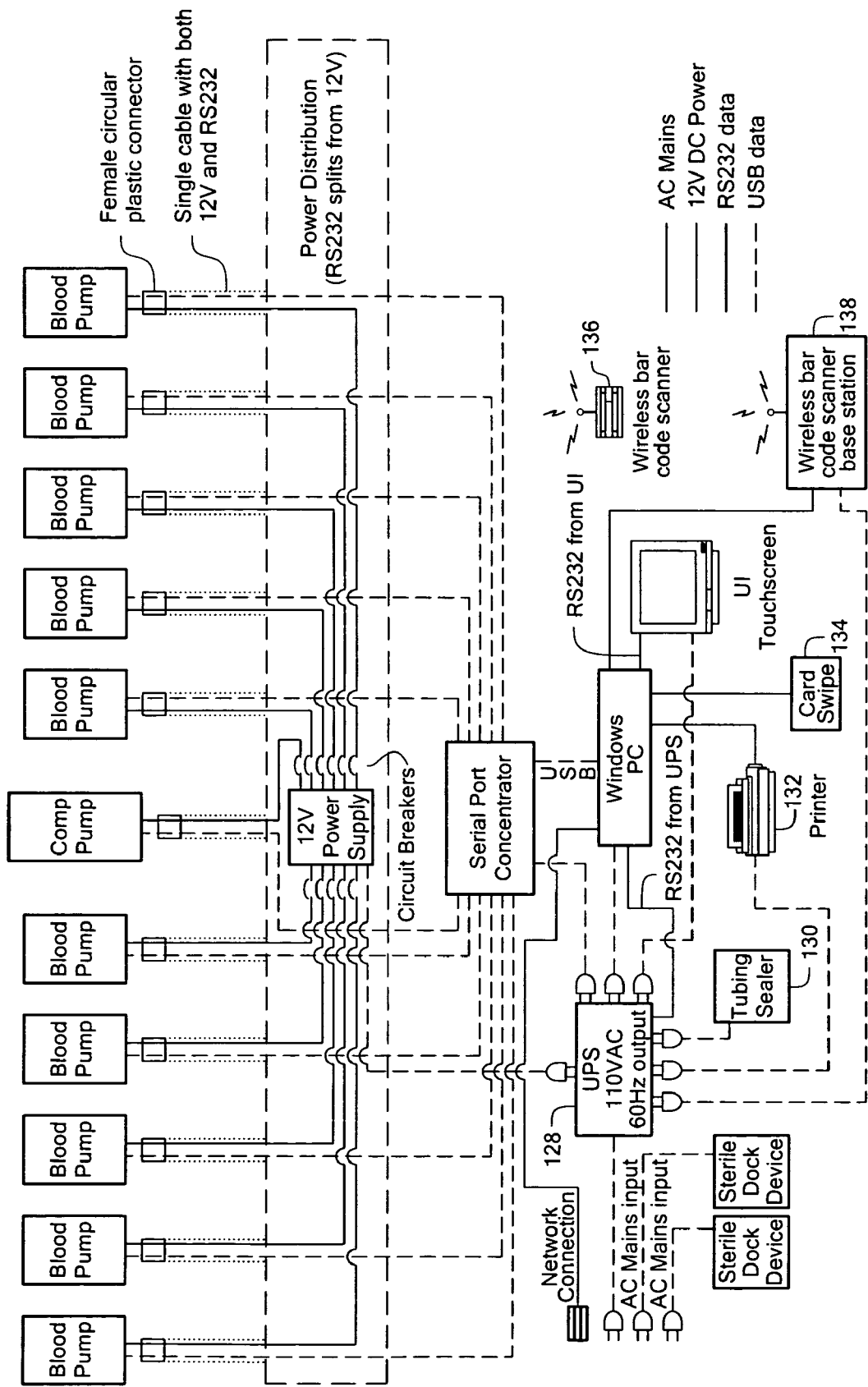
FIG. 1C shows an exemplary wiring diagram for another embodiment of the blood processing system shown in FIG. 1A.

FIG. 1C shows an exemplary wiring diagram for another embodiment of the blood processing system 100. The blood processing system 100 may include a printer in communication with the process controller for printing out reports. The blood processing system 100 may include a card reader 134 in communication with the process controller for card-based operator identification. The blood processing system 100 may include a wireless bar code scanner base station 138 in communication with the process controller for receiving bar code information scanned using a wireless bar code scanner 136. Bar codes are typically used to track the various solution containers and the pumps on which those containers were processed.

The process controller 120 coordinates the actions of the compounder pump 102, the blood pumps 104, and the operator throughout the various mixing operations. The process controller 120 initiates high level embedded commands within the pumps to move and mix the fluids. The process controller 120 instructs the operator through the setup and teardown of each process through the user interface 116. The user interface 116 is also used to inform the operator of any anomalies that may occur during mixing operations.

When the blood processing system 100 is operating from the uninterruptible power supply 128 and at other appropriate times, the process controller 120 will prevent compounding and other pump operations from starting, although the pumps will generally be allowed to complete any ongoing operations. Furthermore, if the process controller fails, the pumps have internal logic for safely completing or terminating any ongoing operations.

Vial Assembly

The anti-pathogen compound is typically provided as a container assembly including a sealed anti-pathogen compound container (typically a sealed glass vial partially filled with anti-pathogen compound) within a protective holder. The protective holder is designed to prevent breakage of the sealed anti-pathogen compound container in case the container assembly is dropped or otherwise mishandled, within predetermined limits. For convenience, the anti-pathogen compound container may be referred to hereinafter a "vial," the protective holder may be referred to hereinafter as a "vial receptacle," and the container assembly may be referred to hereinafter as a "vial assembly."

Figure 2B:
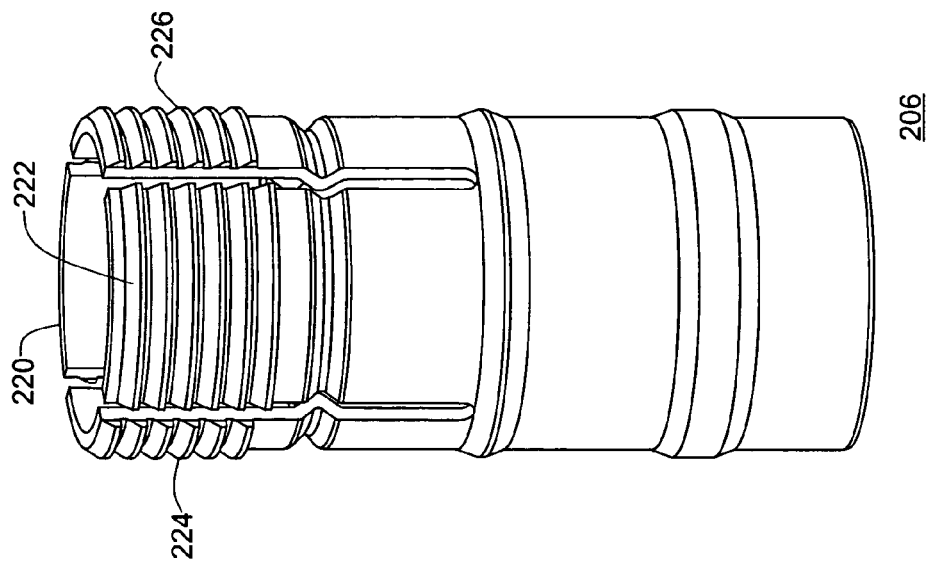
FIG. 2B shows a perspective view of the vial receptacle in accordance with an embodiment of the present invention.
Figure 2A:
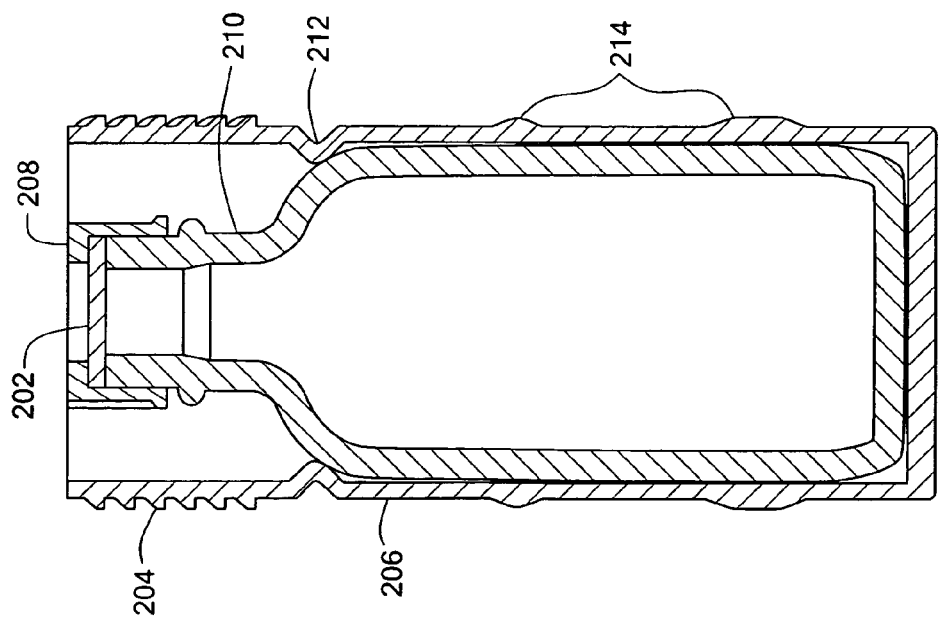
FIG. 2A shows an exemplary vial assembly in accordance with an embodiment of the present invention.

FIG. 2A shows an exemplary vial assembly 200 in accordance with an embodiment of the present invention. The vial assembly 200 includes a vial 210 within a vial receptacle 206. The vial 210 is sealed with a polypropylene screw-on vial cap 208 including a Teflon-faced silicone septum 202 that is capable of being pierced by the spikes of a spike receptacle, as discussed below. The vial receptacle 206 includes a vial containment rib 212 for holding the vial 210 within the vial receptacle 206. The vial receptacle 206 also includes one or more rows of spike receptacle engagement teeth 204 that are undercut for engaging a corresponding vial receptacle locking feature on the spike receptacle so that the spike receptacle cannot be easily removed from the vial receptacle 206 after the vial 210 is spiked, as discussed below. Multiple rows of spike receptacle engagement teeth 204 are typically included to accommodate vial height tolerances so that spiking and locking can be accomplished with various vial heights. The vial receptacle 206 also includes switch engagement features 214 that are essentially protruding rings that operate various switches in a spiking cylinder, as discussed below.

FIG. 2B shows a perspective view of the vial receptacle 206 in accordance with an embodiment of the present invention. The top portion of the vial receptacle 206 incorporating the spike receptacle engagement teeth 204 is preferably divided into four tabs 220, 222, 224, and 226. The tabs are able to deflect inward during spiking so as to facilitate engagement with the vial receptacle locking feature on the spike receptacle, as discussed below. Each tab includes multiple rows of spike receptacle engagement teeth. The teeth on each pair of opposing tabs are essentially aligned, although the teeth on adjacent pairs of tabs are staggered by approximately half the height of a tooth. Among other things, this staggering of the spike receptacle engagement teeth 204 provides twice the number of engagement locations without having to reduce the size of the teeth.

Compounder Disposables

In order to create the inlet and outlet for diluting the anti-pathogen compound in the vial 210 as discussed above, the septum 202 is preferably pierced by a port assembly having two hollow spikes, one acting as the inlet and the other acting as the outlet. For convenience, this piercing operation may be referred to hereinafter as "spiking," and the port assembly may be referred to hereinafter as a "spike receptacle." The outlet spike is connected through plastic tubing to the working solution container. The inlet spike is connected through plastic tubing to the output port of a pump cassette. The pump cassette also has an inlet port that can be connected through plastic tubing to a buffer solution container. The pump cassette is installed in the compounder and serves as an interface between the compounder, the vial 210, and the buffer solution container for pumping buffer solution from the buffer solution container to the vial 210, as discussed below.

In order to dilute the anti-pathogen compound, the buffer solution is typically drawn from the buffer solution container through the inlet port into a chamber of the pump cassette and is then pumped from the pump cassette chamber through the outlet port to the inlet spike and into the vial. In exemplary embodiments of the present invention, the spiking operation and the pumping operations (including drawing the buffer solution from the buffer solution container and pumping the buffer solution to the inlet spike) are controlled pneumatically, as discussed below.

In a typical embodiment of the present invention, the pump cassette, the spike receptacle, the working solution container, and various plastic tubes connected thereto form a compounder disposable set. The compounder disposable set is used for a single compounding operation and is then discarded. The compounder disposable set is described in greater detail in Application D84.

Figure 3A:
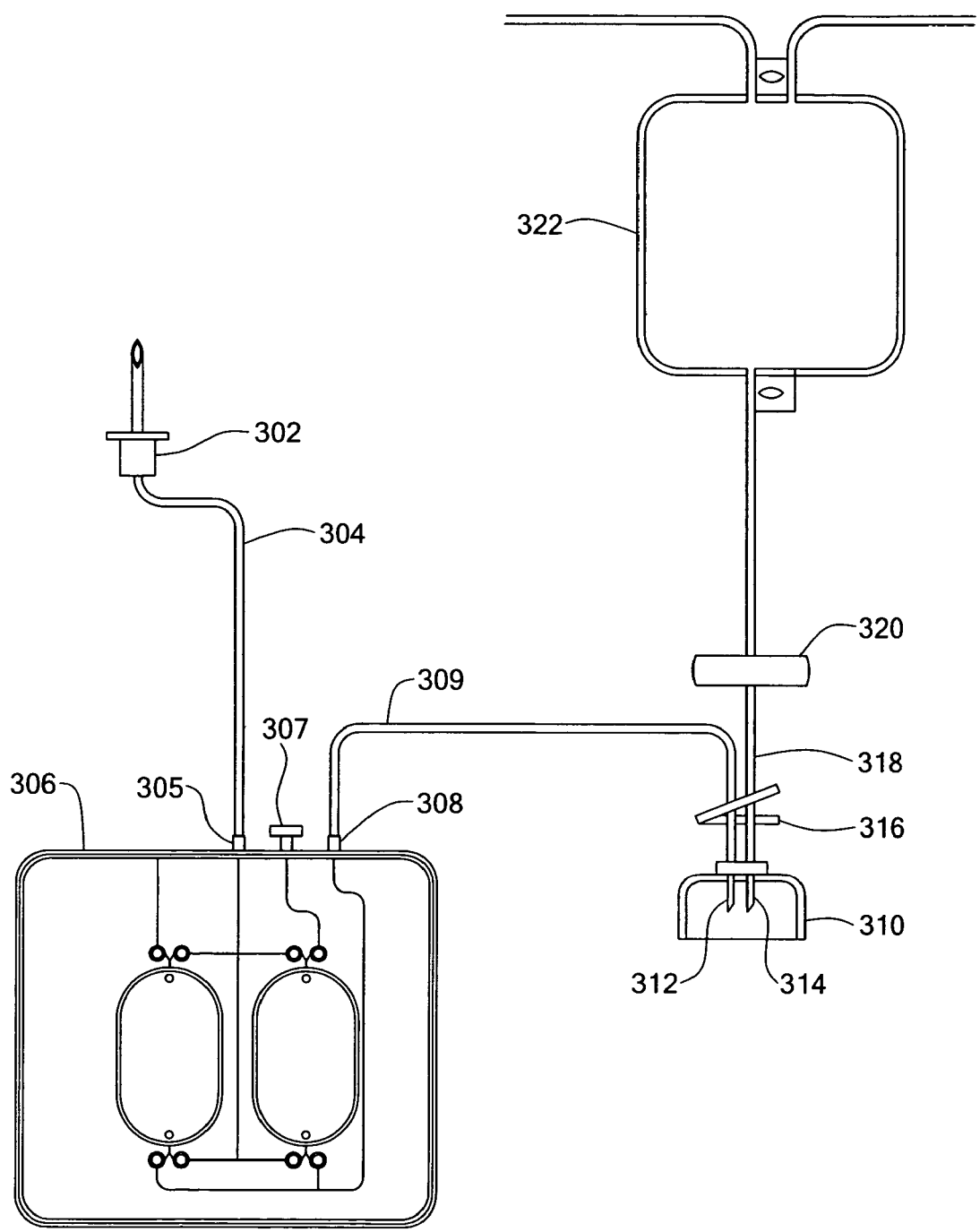
FIG. 3A shows an exemplary compounder disposable set in accordance with an embodiment of the present invention.

FIG. 3A shows an exemplary compounder disposable set 300 in accordance with an embodiment of the present invention. The compounder disposable set 300 includes a pump cassette 306 including an inlet port 305, and outlet port 308, and a vent 307. The inlet port 305 is connected to one end of a plastic tube 304 having, on its other end, a buffer bag spike 302 for piercing a buffer solution container. The outlet port 308 is connected to one end of a plastic tube 309, the other end of which is connected to an inlet spike 312 of a spike receptacle 310. An outlet spike 314 of the spike receptacle 310 is connected to a tube 318 that leads through a filter 320 to a working solution container 322. A tubing clamp 316 is used to crimp the tubes 309 and 316 near the spike receptacle 310 after the compounding operation is complete.

Figure 3B:
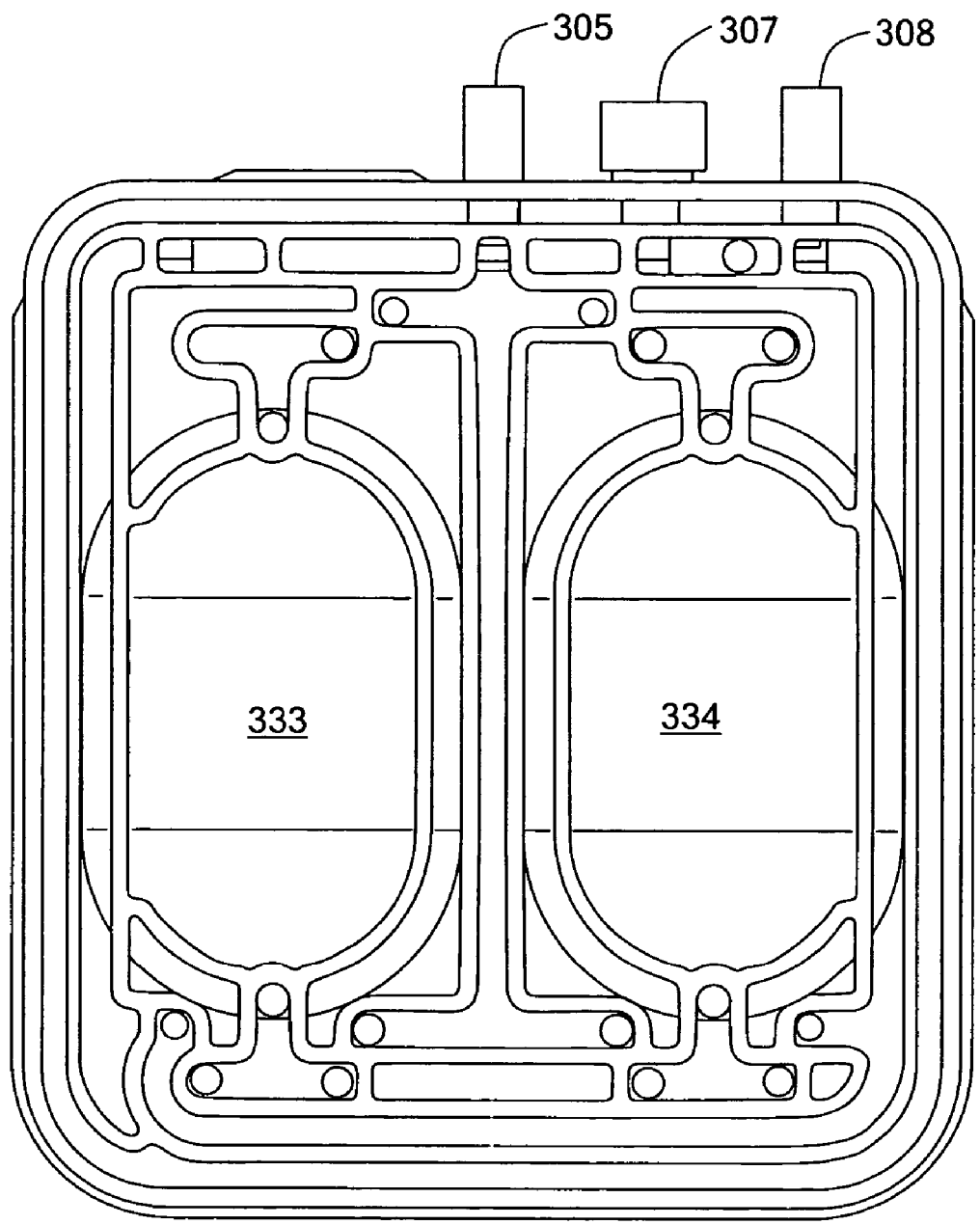
FIG. 3B shows a front view of the compounder pump cassette in accordance with an embodiment of the present invention.

FIG. 3B shows a front view of the compounder pump cassette 306 in greater detail. The pump cassette 306 is essentially a rigid core including formations and sealing ribs 340 constituting various pumping chambers, fluid valves, and fluid pathways (channels). The rigid core is covered on each side by a flexible membrane. The flexible membranes seal against the core and isolate the compounder pump 102 from fluids within the cassette. The pump cassette 306 is designed to interface with the compounder pump 102 in only one direction. For example, the pump cassette 306 typically includes an asymmetric feature (such as the placement of tubing) that prevents the compounder door from closing if the pump cassette 306 is inserted incorrectly.

The pump cassette 306 includes the outlet port 308, the vent port 307, and the inlet port 305. The pump cassette 306 also includes two pumping chambers 333 and 334 that are used to draw buffer solution from the buffer solution container through the inlet port 305 and pump the buffer solution to the vial 210 through the outlet port 308.

Figure 3C:
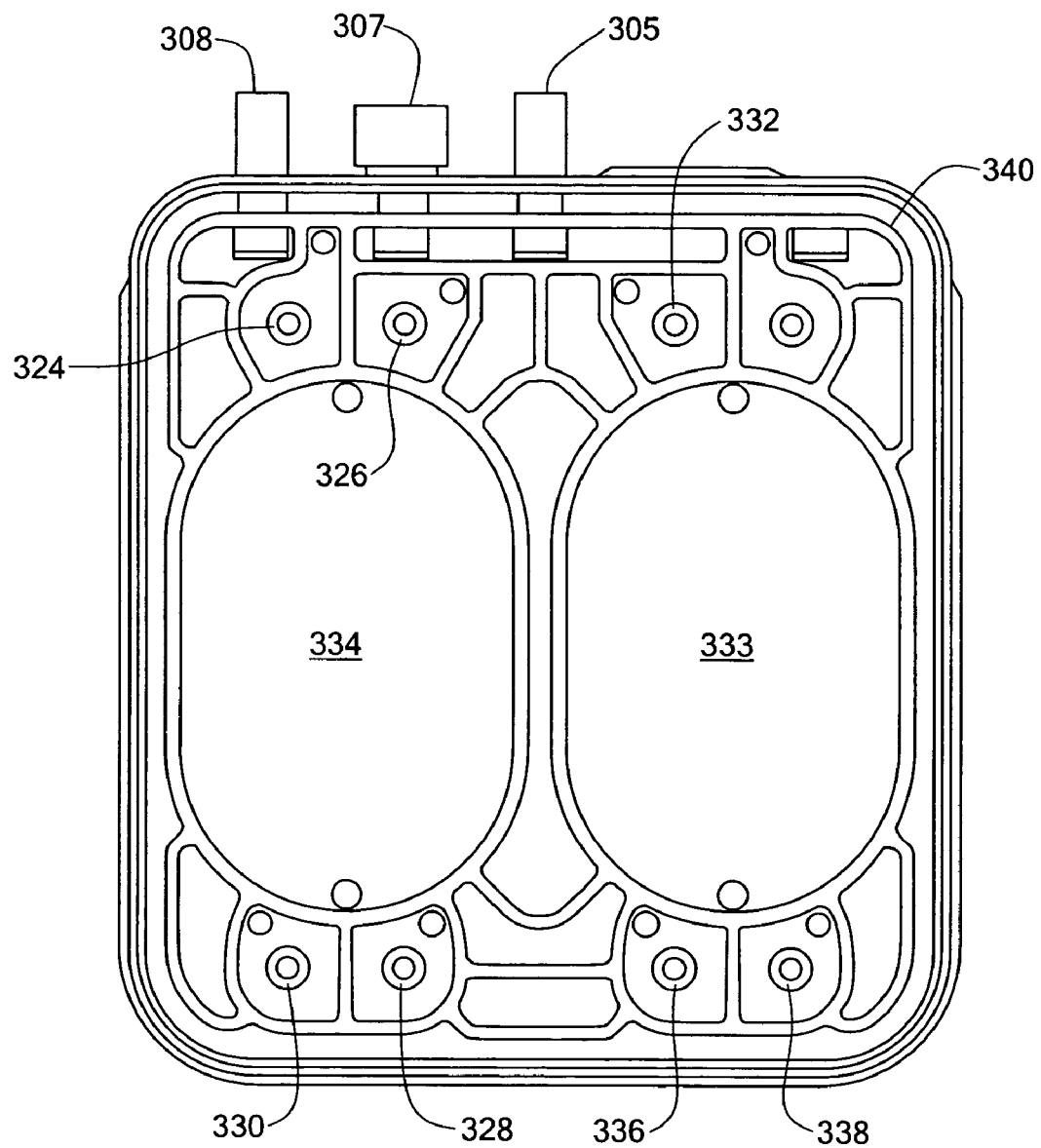
FIG. 3C shows a rear view of the compounder pump cassette in accordance with an embodiment of the present invention.

FIG. 3C shows a rear view of the compounder pump cassette 306. In addition to the inlet port 305, the vent port 307, the outlet port 308, and the pump chambers 333 and 334, the pump cassette 306 includes various "volcano" valves 324, 326, 328, 330, 332, 336, and 338 that are used to open and close various fluid pathways within the pump cassette 306. The volcano valves and the pumping chambers are preferably operated pneumatically from the rear side of the pump cassette 306, as discussed below. The valve 324 is used to control pumping through the vent port, for example, to allow air to be pumped from the pump chambers 333 and 334 out the vent port 307. The valves 326 and 332 are used for priming the pump chambers 334 and 333, respectively. The valves 328 and 336 are used to control pumping of buffer solution through the inlet port 305 into the pump chambers 334 and 333, respectively. The valves 330 and 338 are used to control pumping of buffer solution through the outlet port 308 from the pump chambers 334 and 333, respectively.

Figure 3D:
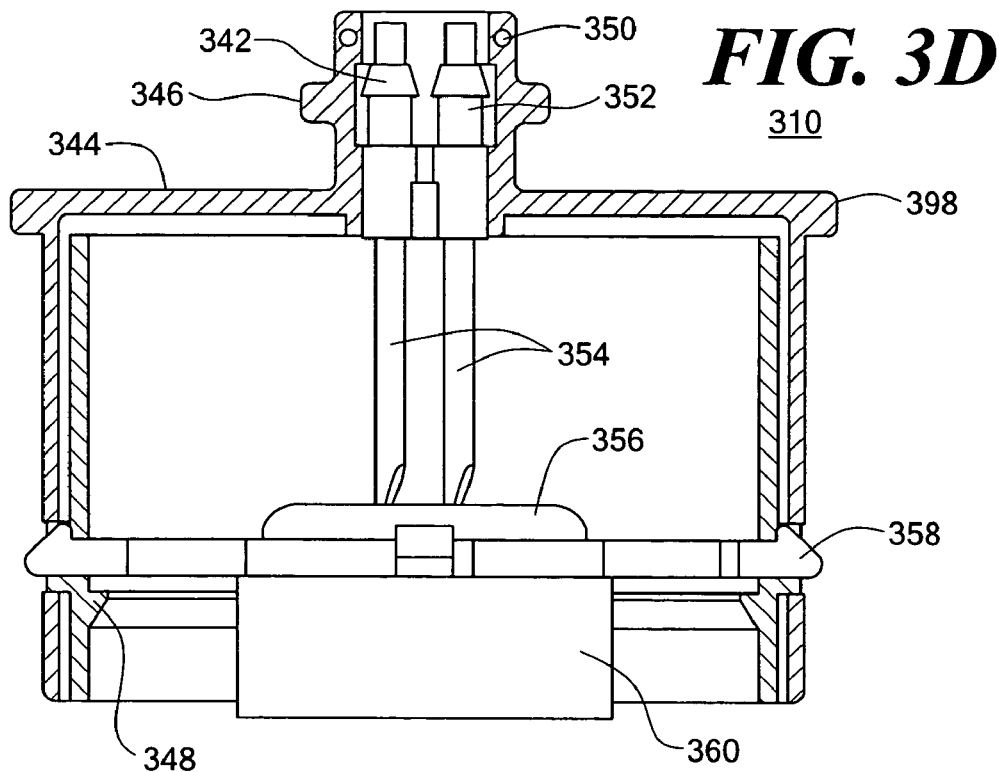
FIG. 3D shows a cross-sectional view of the spike receptacle in accordance with an embodiment of the present invention.

FIG. 3D shows a cross-sectional view of the spike receptacle 310 in greater detail. The spike receptacle 310 includes a housing 344 that holds spikes 354 and a guard 360, and is designed to mate with the vial receptacle 206 during spiking, as discussed below. The housing 344 is preferably made up of two identical halves that, when joined together, are held together by ribs on each side that align with and are engaged by slots on the other side.

The spikes 354 are contained by a polycarbonate spike holder 352 that is preferably overmolded onto the two spikes 354. The overmolded spike holder 352 includes tubing barbs 342. Tubing is attached to the spikes over the tubing barbs 342. The overmolded spike holder 352 helps maintain parallelism of the spikes 354, and provides a fluid-tight connection with the tubing.

The top portion of the housing 344 has an area that engages the overmold's barb feature so as to capture the tubing within the housing 344. This creates a double-mechanical (as well as bonded) feature that permanently attaches the tubing to the spike. The spike housing 344 also features an undercut vial receptacle locking feature 348 that engages the spike receptacle engagement teeth 204 of the vial receptacle 206 to permanently attach the spike receptacle 310 to the vial receptacle 206 after spiking, as discussed below. The spike housing 344 also includes a rim 398 that is slightly wider than the remainder of the housing 344. The rim 398 prevents the spike receptacle 310 from being fully inserted into the vial spike assembly 406. The rim 398 includes two orientation tabs 399 that are used to align the spike receptacle 310 within the vial spike assembly 406.

The guard 360 protects the spikes 354 and protects the operator from the spikes 354. The guard 360 includes a center hole that is filled or covered with an elastomeric (silicone) grommet 356. The guard 360 is designed to engage the vial cap 208, and has four release tabs 358 that hold it loosely in the housing 344. The release tabs 358 protrude out through slots in the housing 344, making it difficult to move the guard 360 when the tabs 358 are in place. When the assembly is placed into the vial spiking assembly, the fingers are pushed in by the inner wall of the spiking cylinder, releasing the guard 360 so that spiking can occur through the grommet 356, as discussed below. The grommet 356 also acts as a redundant seal between the vial cap 208 and the spike guard 360 in case fluid were to leak through the septum 202 around the spikes 354 during pumping.

The spike receptacle 310 includes a sensor feature 346 that is essentially a protruding ring near the top of the spike receptacle 310. The sensor feature 346 is designed to engage a switch in a locking mechanism of the vial spiking assembly, as discussed below.

Figure 3E:
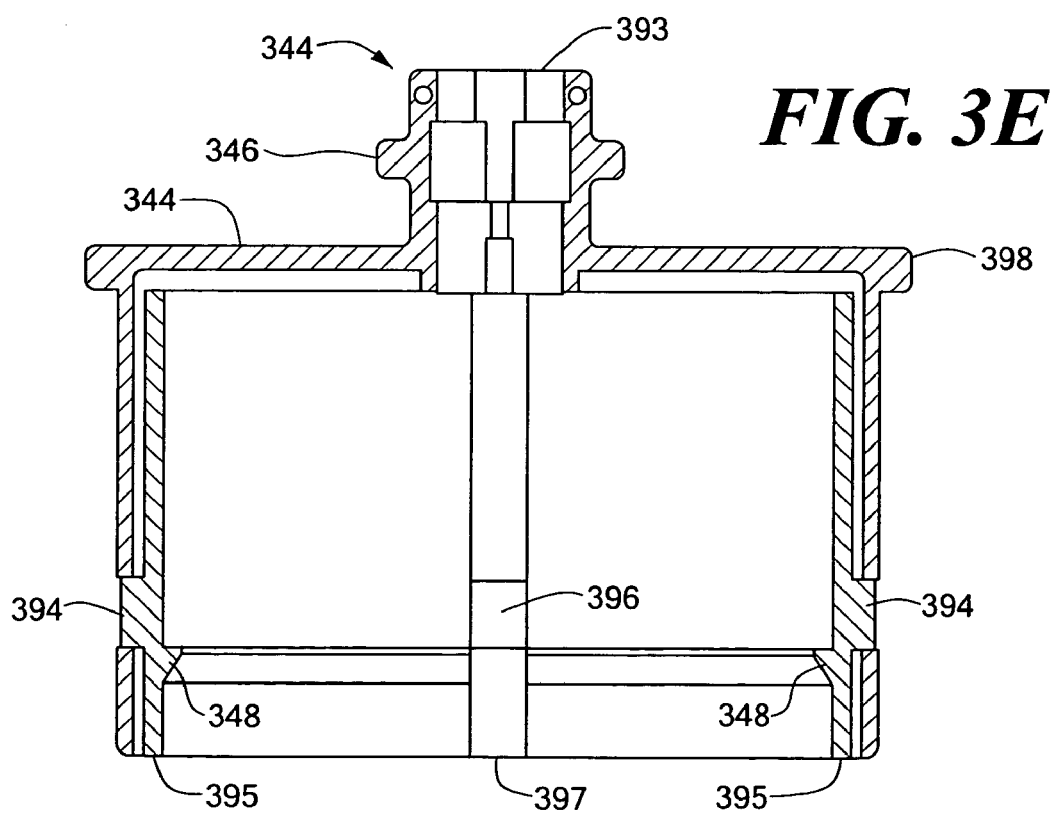
FIG. 3E shows a side view of a spike receptacle housing section in accordance with an embodiment of the present invention.

FIG. 3E shows a side view of a spike receptacle housing section 344 in accordance with an embodiment of the present invention. Among other things, the housing section 344 includes the rim 398, which preferably extends around the outer periphery of the housing section 344, and the undercut vial receptacle locking feature 348, which preferably extends around the inner periphery of the housing section 344. The housing section 344 includes a center channel 397 with a slot 396 for engaging a tab 358 of the guard 360, and also includes a partial channel 395 with a partial slot 394 at each edge such that, when two housing sections 344 are joined, four channels with slots are formed (two central and two where the housing sections meet. When the guard tabs are positioned within the slots, the guard 360 is held substantially in place so as to cover the spikes. When the guard tabs are released from the slots during spiking, the guard 360 is able to slide upward along the channels to allow spiking to occur, and also to provide a redundant seal against the vial in case fluid leaks from around the spikes. The housing section 344 includes formations 393 for receiving and engaging the overmolded spike holder 352 with attached tubing so as to hold the spikes and associated tubing in place.

Figure 3F:
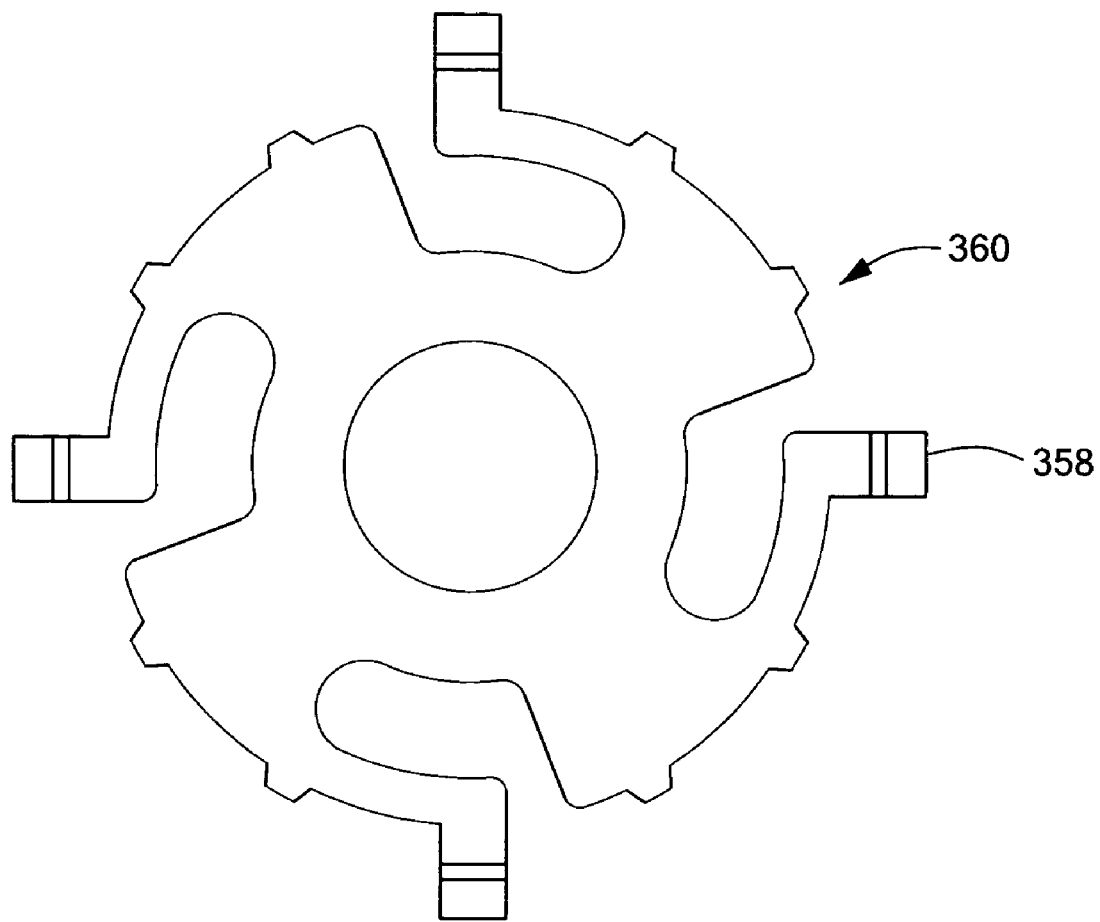
FIG. 3F shows a top view of a spike receptacle guard in accordance with an embodiment of the present invention.

FIG. 3F shows a top view of the guard 360 in accordance with an embodiment of the present invention. The guard 360 includes four tabs 358 that are positioned within, and are engaged by, the channels and slots in the housing 344. The tabs 358 are pushed inward during spiking in order to release the tabs from the slots in the housing 344.

Figure 3G:
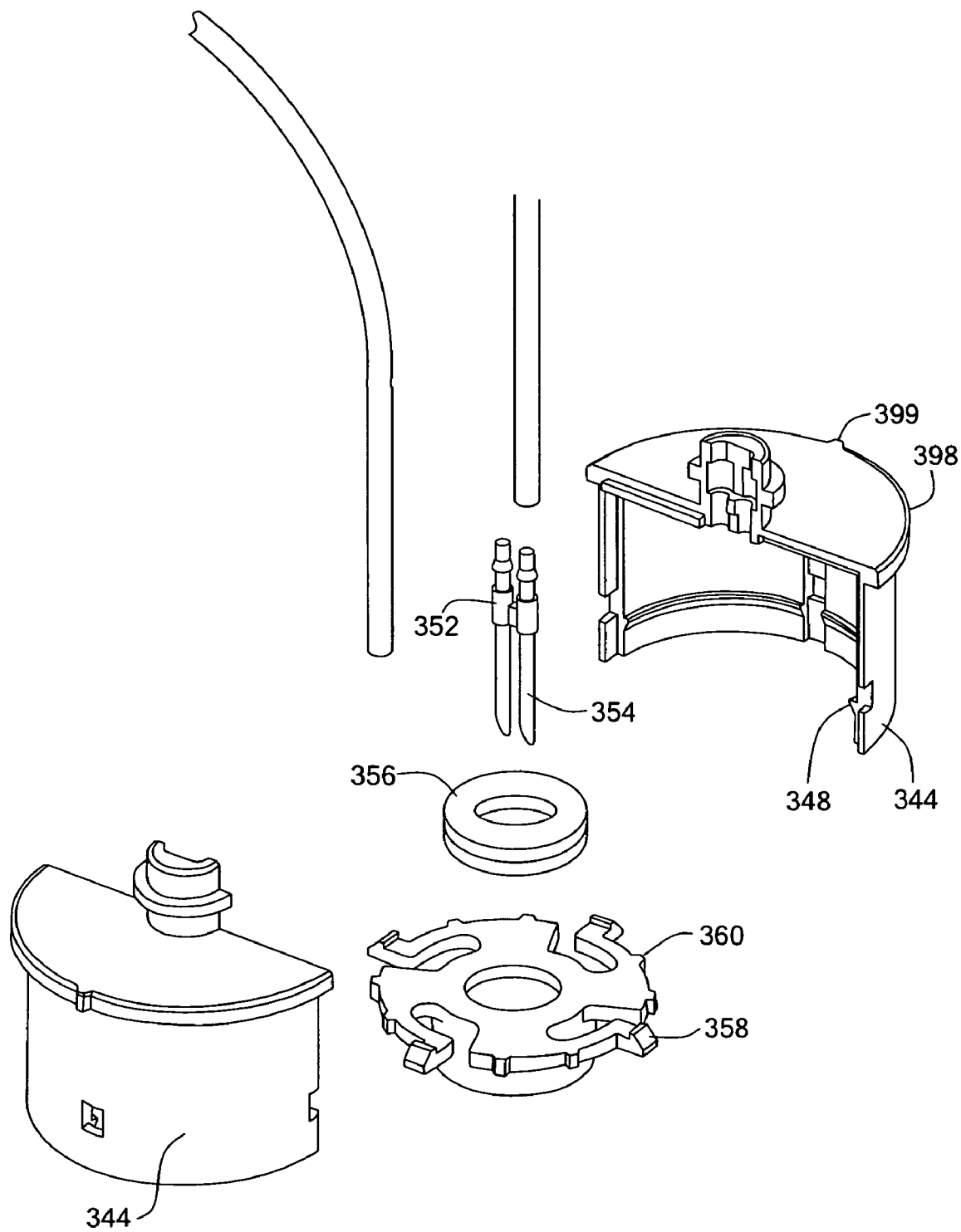
FIG. 3G shows an exploded perspective view of the spike receptacle in accordance with an embodiment of the present invention.
Figure 3H:
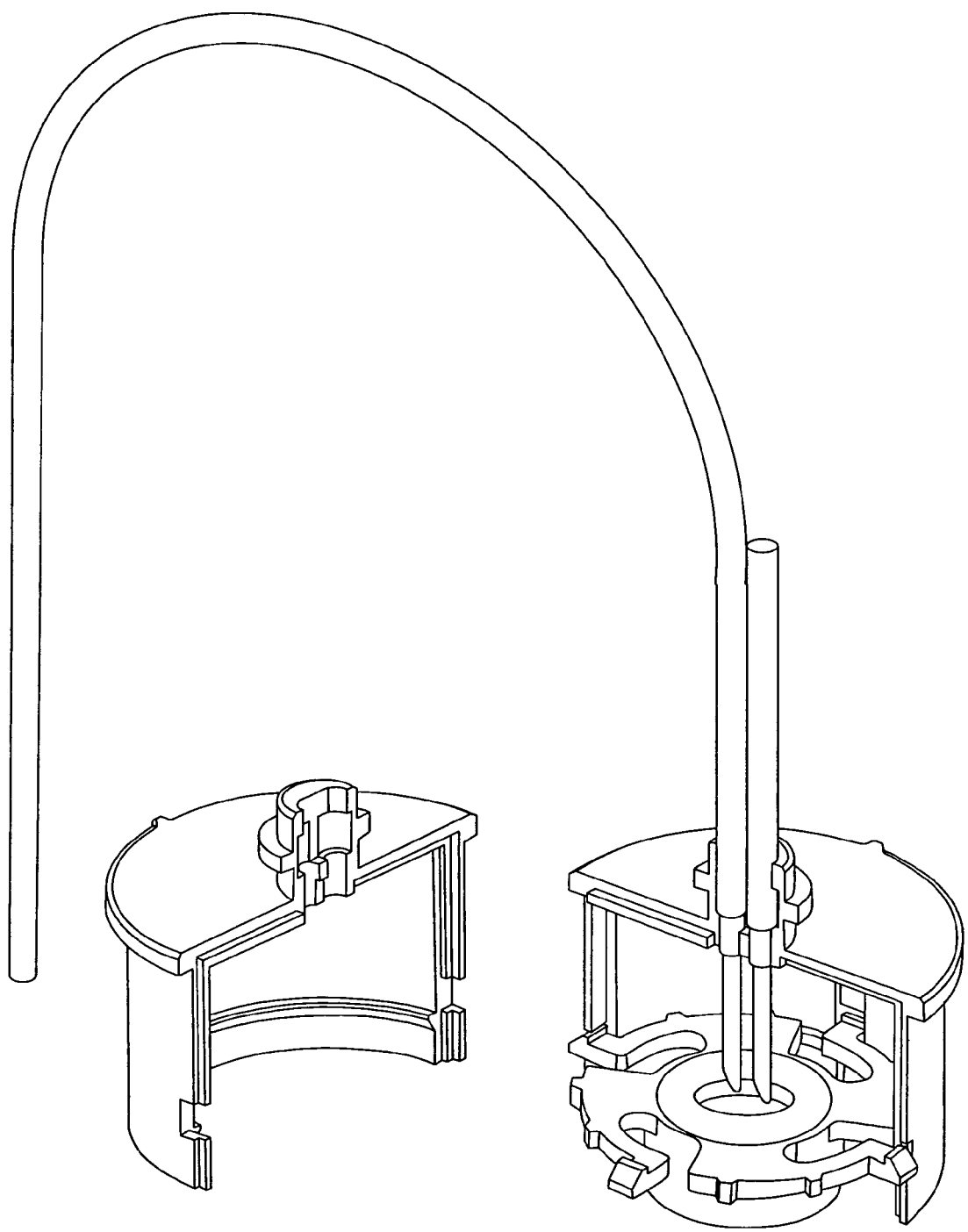
FIG. 3H shows a cut-out perspective view of the spike receptacle in accordance with an embodiment of the present invention.

FIG. 3G shows an exploded perspective view of the spike receptacle 310 in accordance with an embodiment of the present invention. The spike receptacle 310 includes two housing sections 344, guard 360, grommet 356, spikes 354 with overmolded spike holder 352, and associated tubing. The tubing is pushed onto the overmolded spike holder 352 over the barbs. The grommet 356 is inserted into a hole in the guard 360 such that it is held in place by the guard 360 and covers the hole in the guard 360. As shown in FIG. 3H, the overmolded spike holder 352 with attached tubing fits into corresponding formations of the housing sections 344, and the tabs of the guard 360 fit into the slots in the housing sections 344.

With reference again to FIG. 2B, during spiking, the spike receptacle 310 and the vial receptacle 206 are forced together such that the spike receptacle 310 becomes locked onto the vial receptacle 206 over the tabs 220, 222, 224, and 226. During spiking, the tabs deflect inward as needed to allow the vial receptacle locking feature 348 to pass over successive rows of spike receptacle engagement teeth 204 until the vial receptacle 206 is seated as far onto the vial receptacle 206 as possible. The staggered teeth provide twice as many engagement points for the vial receptacle locking feature 348 compared to teeth that are not staggered.

While the spiking receptacle 310 preferably includes two hollow spikes for forming the inlet and outlet, it should be noted that the present invention is in no way limited to two spikes. A single spike having both an inlet channel and an outlet channel could be used. Alternatively, multiple inlet spikes and/or multiple outlet spikes could be used.

Figure 3I:
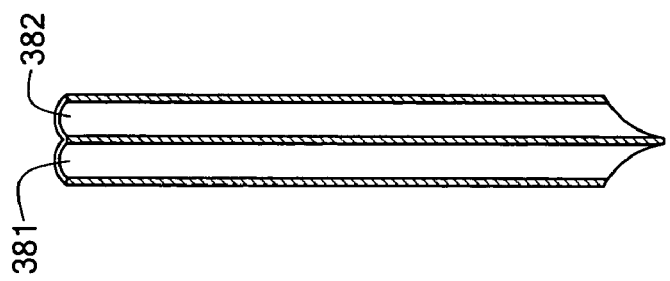
FIG. 3I shows a cross-sectional view of an exemplary spike having two fluid channels in accordance with an embodiment of the present invention.

FIG. 3I shows a cross-sectional view of an exemplary spike having two fluid channels 381 and 382 in accordance with an embodiment of the present invention. In a typical embodiment of the invention, one of the fluid channels would be used to provide an inlet to the vial, while the other fluid channel would be used to provide an outlet from the vial. Appropriate tubing connections would typically be provided to allow separate tubing to be connected to the two fluid channels.

Compounder

As discussed above, the compounder 102 creates a working solution of anti-pathogen compound and buffer solution. A disposable pump cassette 306 serves as an interface between the compounder 102, the vial 210, the buffer solution container, and the working solution container, so that no anti-pathogen compound, buffer solution, or working solution comes into actual contact with the components of the compounder 102. The compounder 102 preferably uses pneumatics to operate the pump cassette 306 as well as other components, as discussed below. Each compounding cycle of the compounder 102 typically makes a sufficient quantity of working solution for processing 30 RBCC containers by the ten blood pumps 104.

The compounder produces the working solution by pumping a quantity of buffer solution from the buffer solution container to the vial so as to mix with the anti-pathogen compound in the vial to produce working solution. Adding the buffer solution to the vial causes the level of the working solution to rise within the vial. When the working solution rises to the level of an outlet provided in the vial, the working solution is permitted to flow from the vial to the working solution container.

The compounder 102 preferably includes a library of generic pump control (N-Pump) functions. The N-Pump library functions are used to perform various generic pumping operations such as, for example, pumping fluid into a chamber of the pump cassette, pumping fluid out of a chamber of the pump cassette, measuring the amount of fluid pumped, performing air detection, and maintaining tank pressures. The compounder 102 preferably also includes a Fluid Logic Module (FLM) that contains higher level functions that employ the N-Pump library functions to implement compounder-specific functions (such as specific logic for mixing the buffer solution with the anti-pathogen compound to produce the working solution).

The compounder 102 includes one master board connected to two pump boards that together perform the N-Pump and FLM functions. The master board communicates to each of the pump boards via a multi-drop RS-485 bus. Each pump board controls a single pump chamber of the pump cassette 306 and the valves on its board.

In the compounder 102, the pump chambers are synchronized to pump in series. Thus, as one chamber is filling with buffer solution, the other chamber will be delivering buffer solution to the vial. The pumping algorithm is typically terminated when the volume of buffer solution pumped is within one pump stroke of the target volume.

Figure 4:
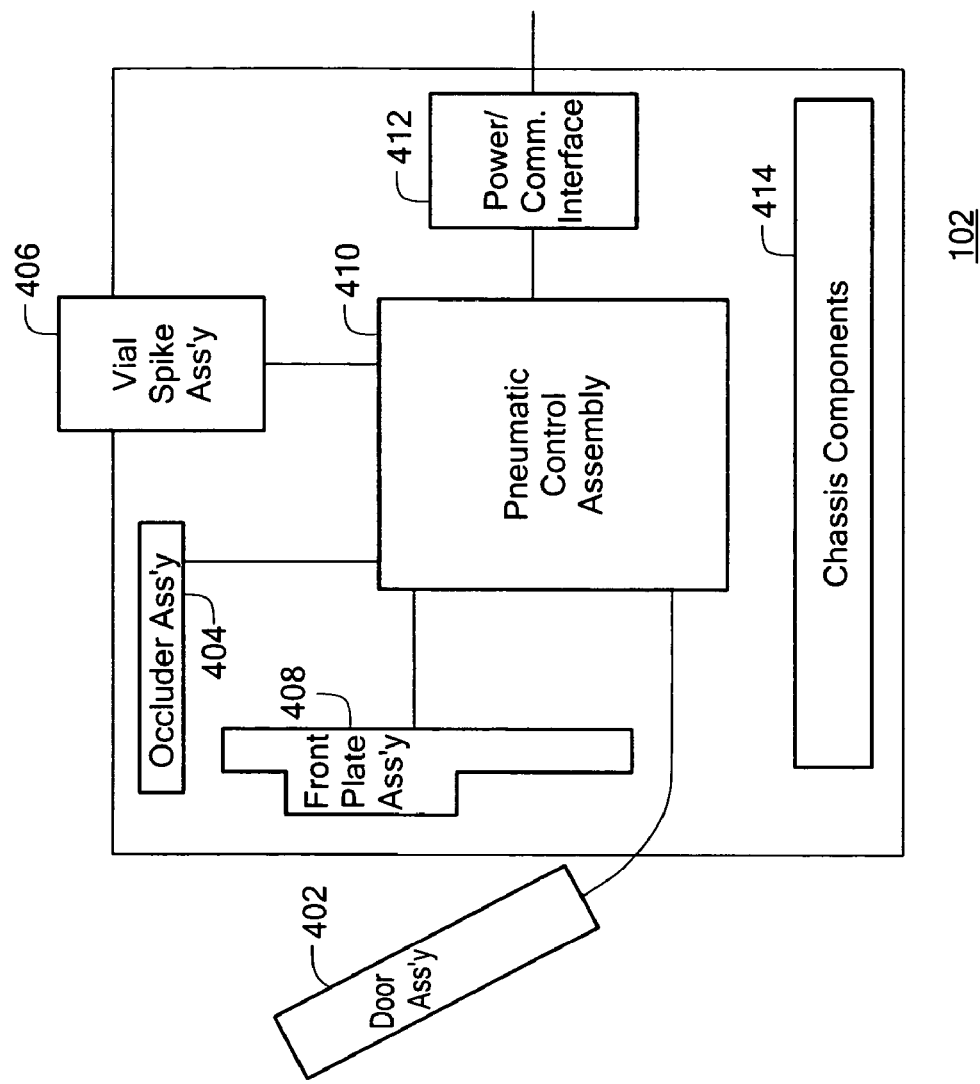
FIG. 4 shows a conceptual block diagram of the compounder in accordance with an embodiment of the present invention.

FIG. 4 shows a conceptual block diagram of the compounder 102 in accordance with an embodiment of the present invention. Among other things, the compounder 102 includes a door assembly 402, an occluder assembly 404, a vial spike assembly 406, a front plate assembly 408, a pneumatic control assembly 410, a power/communication interface 412 including connectors for the 12-Volt power supply and the RS-232 communication link to the process controller 120, and chassis components 414. Each of these assemblies will be discussed below.

Pneumatic Control Assembly

Figure 5A:
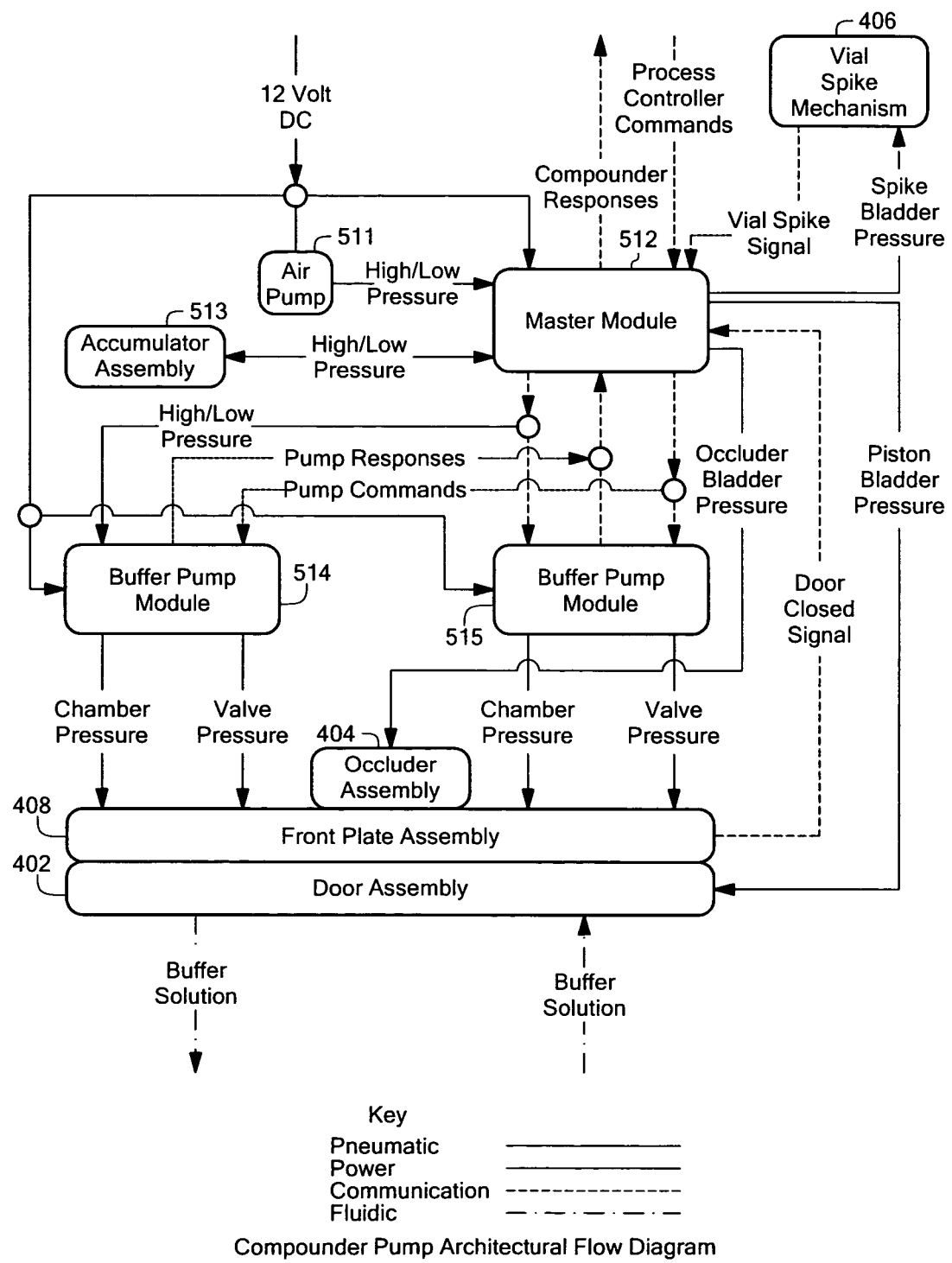
FIG. 5A is an architectural flow diagram showing the relationship between the pneumatic control assembly and the other assemblies in accordance with an embodiment of the present invention.

The pneumatic control assembly 410 provides positive and negative air pressure for operating the various other pneumatically controlled components and also acts as the general controller for the compounder 102. FIG. 5A is an architectural flow diagram showing the relationship between the pneumatic control assembly 410 and the other assemblies in accordance with an embodiment of the present invention. In this figure, the pneumatic control assembly 410 is represented by master module 512, accumulator assembly 513, and two buffer pump modules 514 and 515. The air pump 511 is considered to be one of the chassis components 414. The air pump 511 generates high and low air pressure for the master module 512, which stores high and low air pressure in the accumulator assembly 513. The pneumatic control assembly 410 directs air pressure (positive and negative), from the DC air pump 411, to the various pneumatic mechanisms of the pump. The master module 512 pneumatically controls a bladder in the occluder assembly 404, a bladder in the door assembly 402, and a bladder in the vial spiking assembly 406, as discussed below. The master module 512 provides high and low air pressure to the buffer pump modules 514 and 515. Each buffer pump module 514 and 515 controls a single pump chamber of the pump cassette 306 through the front plate assembly 408 and the valves on its module.

Figure 5C:
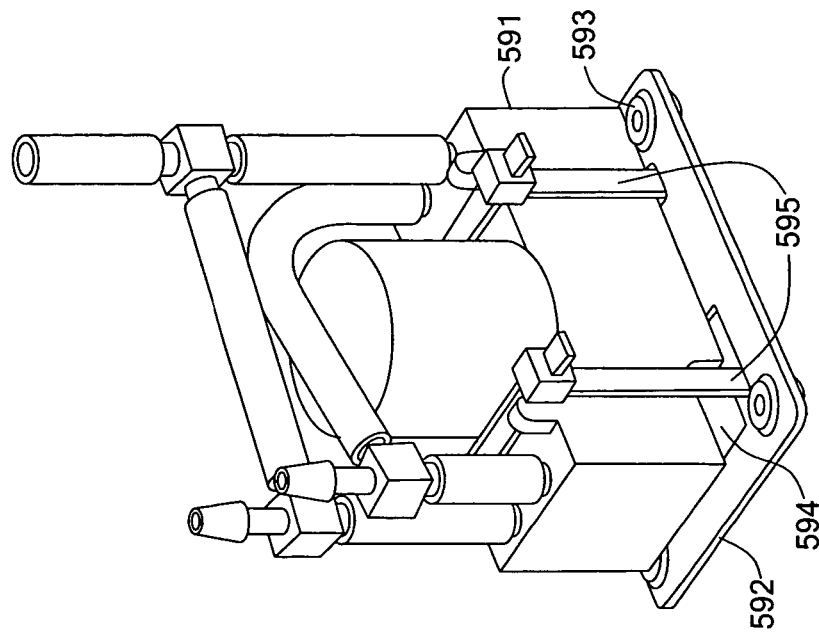
FIG. 5C shows an exemplary embodiment of the air pump in accordance with an embodiment of the present invention.
Figure 5B:
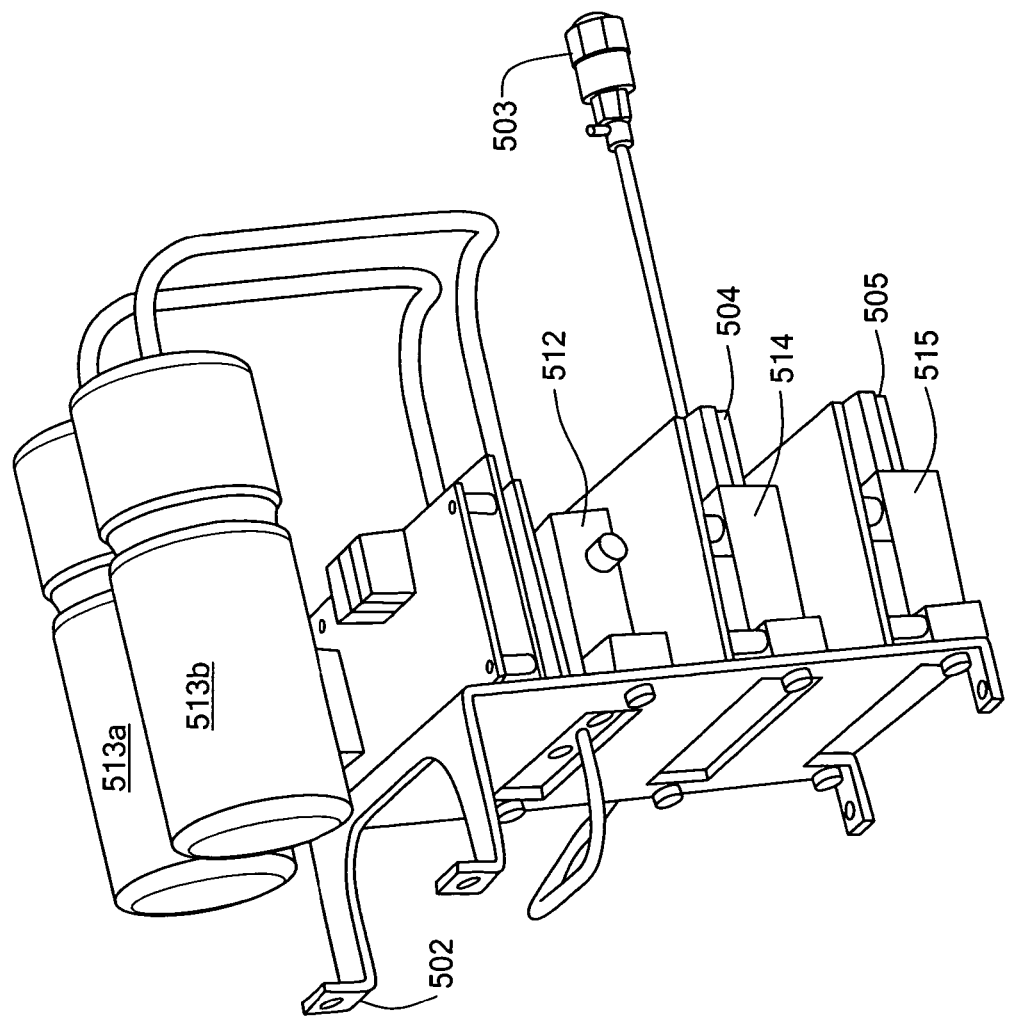
FIG. 5B shows an exemplary embodiment of the pneumatic control assembly in accordance with an embodiment of the present invention.

FIG. 5B shows an exemplary embodiment of the pneumatic control assembly 410 in accordance with an embodiment of the present invention. Among other things, the pneumatic control assembly 410 includes manifold mounting bracket 502, a negative pressure accumulator (pressure bottle) 513a, a positive pressure accumulator (pressure bottle) 513b, a manual door vent mechanism 503, the Tank Management Module Assembly 512, the two Chamber Module Assemblies 514 and 515, and associated tubing and fittings.

The tank management module 512 includes an input/output (I/O) board, a CPU board, a valve-interface board, a pneumatic manifold system, pneumatic valves, pressure transducers 2-vent covers (mufflers), stand-offs, and associated tubing and fittings. The tank management module 512 is used to control the pressures in the accumulators 513, a bladder in the door assembly 402, a bladder in the occluder assembly 404, and a bladder in the vial spiking assembly 406. The I/O board contains electrical controls for controlling LEDs that provide status information to the operator and for controlling various sensors in the vial spiking assembly 406. The pressure transducers are used to monitor the pressures of the accumulators 513 and the bladder in the door assembly 402.

In the un-powered state, the pneumatic valve that controls flow to the bladder in the door assembly 402 preferably shuts closed. This prevents the door from being opened in the event of a loss of power.

In the un-powered state, the pneumatic valve that controls flow to the bladder in the occluder assembly 404 is preferably channeled to vent. This causes the occluder to occlude the tubing to prevent further flow of fluid through the tubing, as discussed below.

Each chamber module 514 and 515 includes a CPU board, a valve interface board, pneumatic manifold system, pneumatic valves (including a VSO (variable) valve), a VSX chamber (504 and 505 respectively), O-ring, copper mesh, vent cover (muffler), stand-offs, pressure transducers, and associated tubing and fittings. Each chamber module assembly controls the pneumatics for one of the pumping chambers and its associated valves. The VSX chambers 504 and 505 act as reference volumes in order to measure the volume of fluid that is delivered with the FMS system. The pressure transducers are used to monitor the pressure of the VSX chamber, and of the pumping chamber. The positive pneumatic system contains a pressure relief valve to prevent the air pump from pressurizing the positive system to greater than 16.0 psig.

In the un-powered state, all of the pneumatic valves preferably open the fluid valves to the positive pressure line. This ensures that the fluid valves are closed if there is a loss of power.

The compounder 102 typically includes three microprocessor systems, one on the tank management module 512 and one on each of the chamber modules 514 and 515. These three microprocessor systems monitor each other for normal operation. Each microprocessor system also monitors key internal processes and data for validity. If any of these monitors fail, a failsafe line permits any of the three processors to stop pumping operations, close all of the fluid valves and occluder, and send an anomaly signal to the process controller. If the compounder 102 detects an anomaly with the commands received from the process controller (e.g., commands received out of sequence), then the compounder will stop fluid flow and send an anomaly signal to the process controller.

FIG. 5C shows an exemplary embodiment of the air pump 511 in accordance with an embodiment of the present invention. The air pump 511 includes a pump motor 591 mounted to a pump plate 592 using double-sided tape 594 and two miniature nylon cable ties 595. Four ribbed isolator grommets 593 are inserted into corresponding openings in the pump plate 592.

Front Plate Assembly

The front plate assembly 408 includes all necessary pneumatic pathways to interface to the disposable pump cassette 306. The front plate assembly 408 includes a bezel and a bezel gasket through which the pump cassette 306 is operated. During operation of the compounder 102, the pump cassette 306 is positioned in the door assembly 402 and is pressed against the front plate assembly 408 in alignment with the bezel and bezel gasket by a bladder in the door assembly 402, as discussed below. Air lines connected to the bezel from the pneumatic control assembly 410 are used to displace membranes of the bezel gasket to operate the various valves and chambers of the pump cassette 306.

Figure 6:
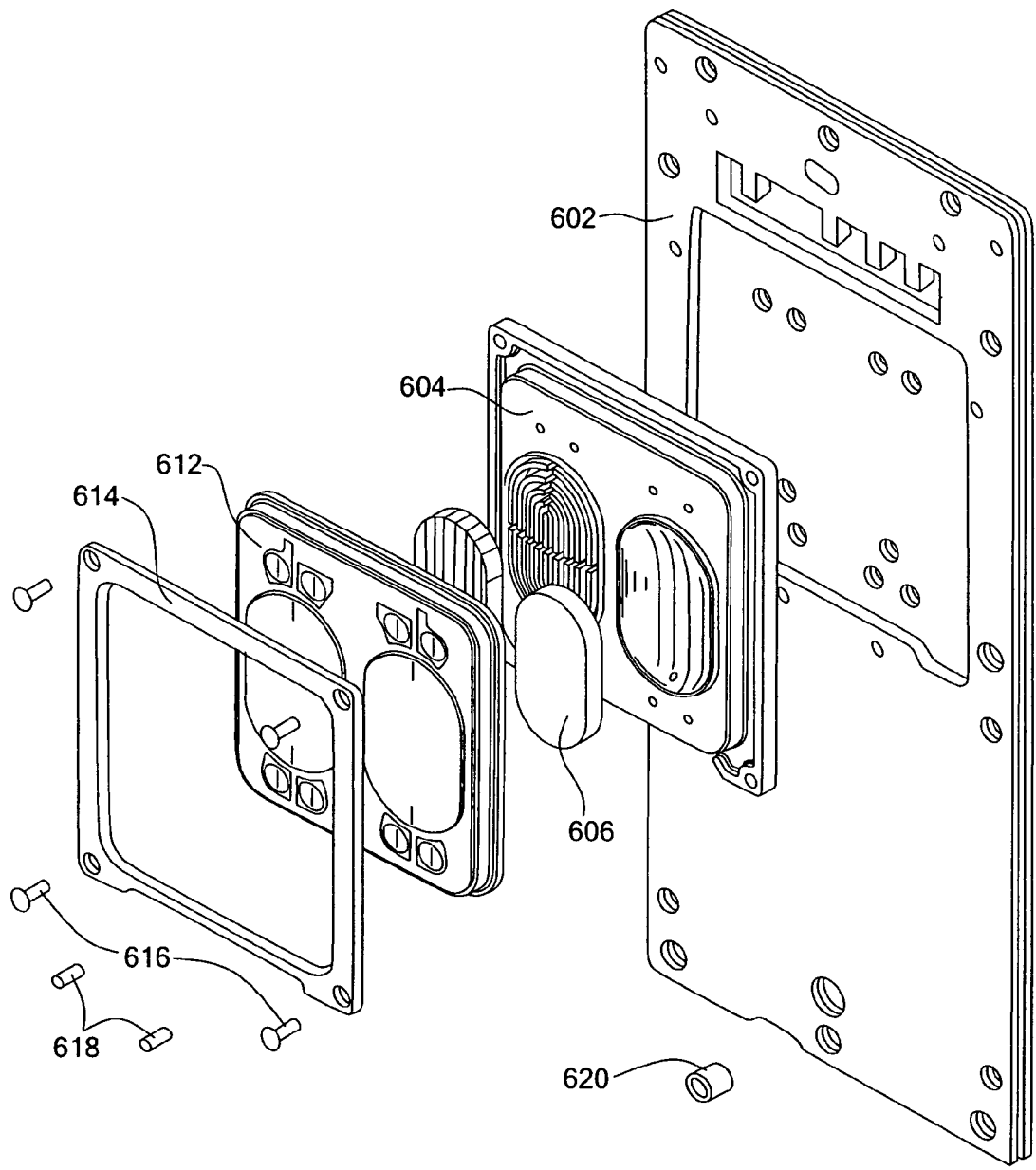
FIG. 6 shows an exploded view of an exemplary front plate assembly in accordance with an embodiment of the present invention.

FIG. 6 shows an exploded view of an exemplary front plate assembly 408 in accordance with an embodiment of the present invention. Among other things, the front plate assembly 408 includes a rigid front plate 602 to which are mounted a bezel 604, chamber foam 606, bezel gasket 612, gasket retainer 614, hardware 616, dowel pins 618, and grommet 620. The bezel 602 includes two chamber cavities for respectively operating the two pump chambers of the pump cassette 306. The bezel 602, chamber foam 606, and bezel gasket 612 are mounted to the front plate 602 by the gasket retainer 614 and associated hardware 616. The front plate 602 includes holes for allowing air tubes to pass between the rear of the bezel 604 and the pneumatic control assembly 410, which is typically situated behind the front plate 602. The front plate 602 also includes openings for an occluder and for engaging a door latch mechanism.

In exemplary embodiments of the present invention, the bezel is a polycarbonate/ABS component that is molded with rib structures in one of the chamber cavities. The rib structures are removed for use in the compounder 102. The bezel with rib structures is described in greater detail in Application D75.

The pneumatic system's tubing connections are typically accomplished using integral ports on the bezel 604, eliminating independent fittings and accompanying O-rings. The bezel gasket 612 is used in conjunction with the bezel 604. The bezel gasket 612 is used to seal the fluid paths of the pump cassette and to provide an interface to actuate the pump cassette valves. The tubing is fed through clearance holes in the front plate 602, so that it can be connected to the pneumatic manifold system located behind the front plate 602. The front plate 602 supports the bezel from behind. The bezel gasket 612 is placed over the bezel 604, on the front side, and held in place using the gasket retainer 614 (which also fastens the bezel 604 to the front plate 602).

Door Assembly

The door assembly 402 provides a means to load and align the disposable cassettes within the compounder 102. The door assembly 402 provides a force on the disposable cassette against the bezel components of the front plate assembly 408 in order to provide sealing of the cassette's fluid paths and valves, as described in greater detail in Application D73. The door assembly 402 includes a special latch system that helps maintain the seal, and also helps prevent accidental opening of the door during processing, as described in greater detail in Application D74. The door assembly 402 also provides a surface for the occluders to function against.

Figure 7A:
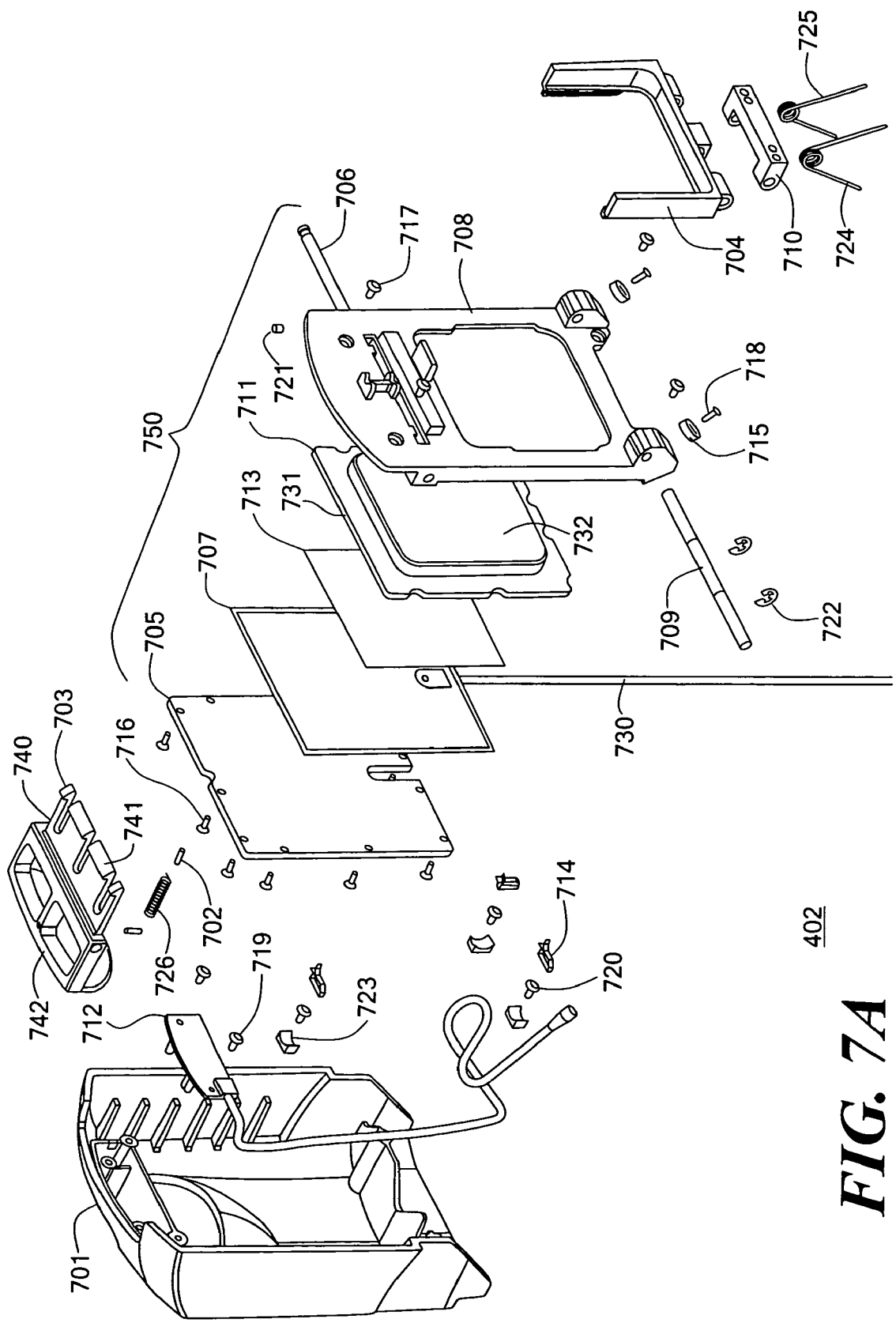
FIG. 7A shows an exploded view of the door assembly in accordance with an embodiment of the present invention.

FIG. 7A shows an exploded view of the door assembly 402 in accordance with an embodiment of the present invention. Among other things, the door assembly 402 includes a door cowl 701, a latch spring post 702, a door latch 703, a cassette receptacle 704, a back plate 705, a latch pin 706, a bladder 707 with an attached pneumatic circuit 730, a frame 708, a door pin 709, a door mounting bracket 710, a piston assembly 711 including a piston plate 731 and a piston cover 732, a human interface board assembly 712, double coated tape 713, a miniature cable tie 714, recessed bumpers 715, E-rings 722, cable tie mount 723, torsion springs 724 and 725, extension spring 726, a cassette orientation tab 799, and various screws 716, 717, 718, 719, 720, and 721. The human interface board assembly 712 is mounted to the inside of the door cowl 701. The piston assembly 711 includes a rigid plate 731 having a protrusion that is covered by the piston cover 732. The bladder 707, double coated tape 713, and piston assembly 711 are sandwiched between the back plate 705 and the frame 708, which are mechanically coupled together to form a frame assembly 750. The door latch 703 is positioned so that a handle portion is accessible from a front side of the door cowl 701. The frame assembly 750 is mounted to the inside of the door cowl 701 so that a latch portion of the door latch 703 protrudes through the frame assembly 750 and the frame assembly 750 holds the door latch 703 in place. The cassette receptacle 704 is pivotally mounted to the frame 708 using the door mounting bracket 710, the door pin 709, and the E-rings 722. Recessed bumpers 715 reduce strain on the door if the door is opened too far or with excessive force. The torsion springs 724 and 725 aid the operator in closing the door, as the door has considerable weight due to the many components. The cassette orientation tab 799 prevents the door from being closed if the pump cassette is oriented incorrectly in the cassette receptacle 704.

The bladder 707 is coupled to, and controlled by, a pneumatic circuit 730 that provides positive and/or negative air pressure to the bladder 707. Positive pressure supplied to the bladder 707 causes the bladder 707 to expand in the direction of the frame 708. This, in turn, causes the entire piston assembly 711 to move toward the control assembly 408, such that the piston cover 732 presses against the pump cassette 202 and/or cassette receptacle 704, thereby producing an outward force on the door 402 away from the control assembly 408. Alternatively, supplying negative pressure to the bladder 707 causes the piston assembly 711 to move away from the pump cassette 202 and/or cassette receptacle 704, thereby reducing the outward force on the door 402 away from the control assembly 408.

The door assembly is designed to permit single-handed operation, specifically by pulling up on the handle. However, the door latch 703 is designed so that the door cannot be easily opened when the pump cassette is in place in the cassette receptacle 704 with the door closed and the bladder 707 is inflated. Specifically, the latch portions of the door latch 703 have undercuts that are engaged by recesses in the front plate assembly 408. When the pump cassette is in place in the cassette receptacle 704 with the door closed and the bladder 707 is inflated so as to push the pump cassette against the bezel components of the front plate assembly 408, a sufficient force is generated between the door assembly 402 and the front plate assembly 408 to prevent the door handle from being easily lifted. This door locking mechanism is described in greater detail in Application D74.

Figure 7B:
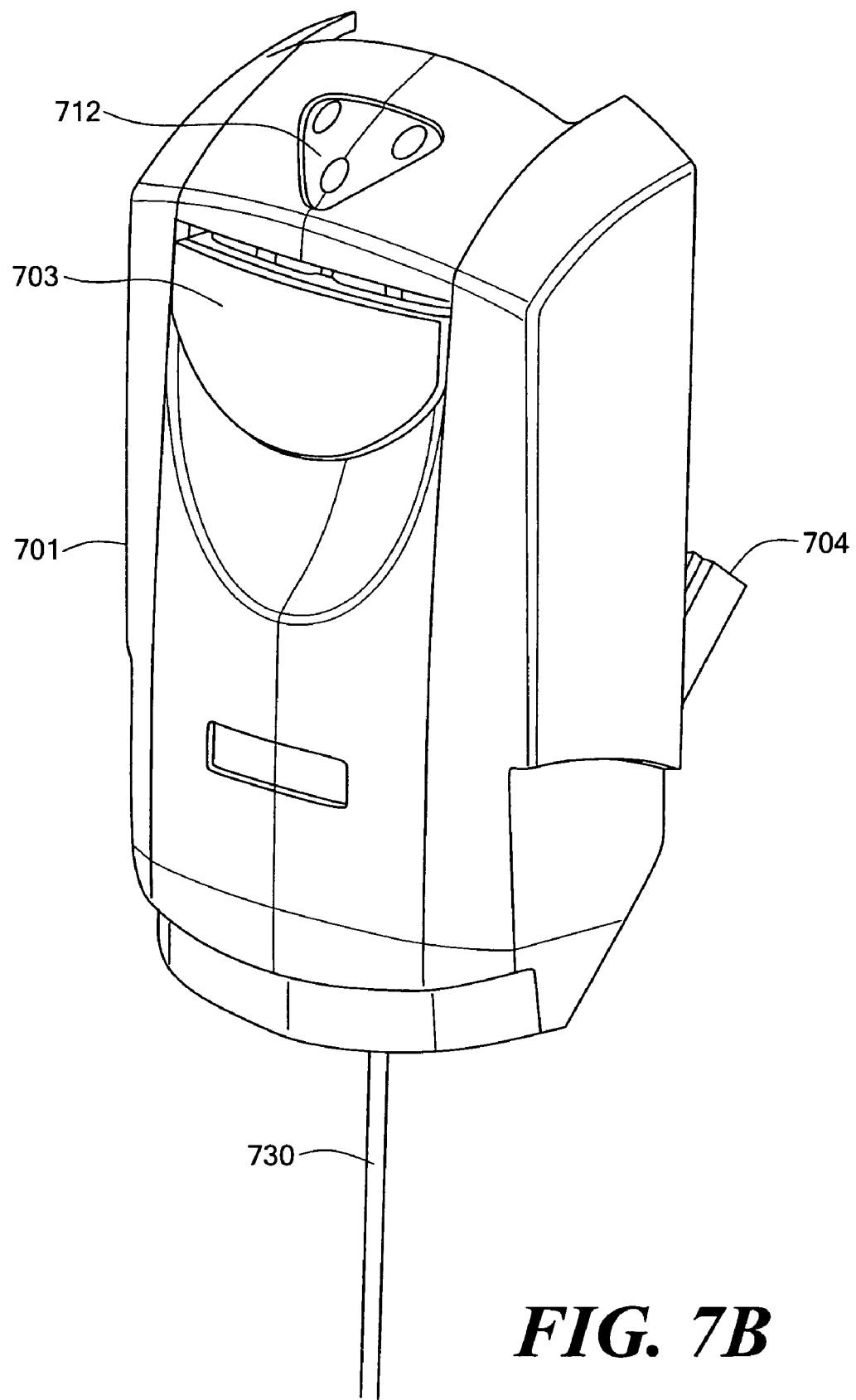
FIG. 7B shows a front perspective view of the door assembly shown in FIG. 7A in accordance with an embodiment of the present invention.

FIG. 7B shows a front perspective view of the door assembly 402 in accordance with an embodiment of the present invention. The human interface board assembly 712 having LEDs and the handle portion of the door latch 703 are visible from the front of the door cowl 701. A portion of the cassette receptacle 704 and a portion of the pneumatic circuit 730 are also visible.

Figure 7C:
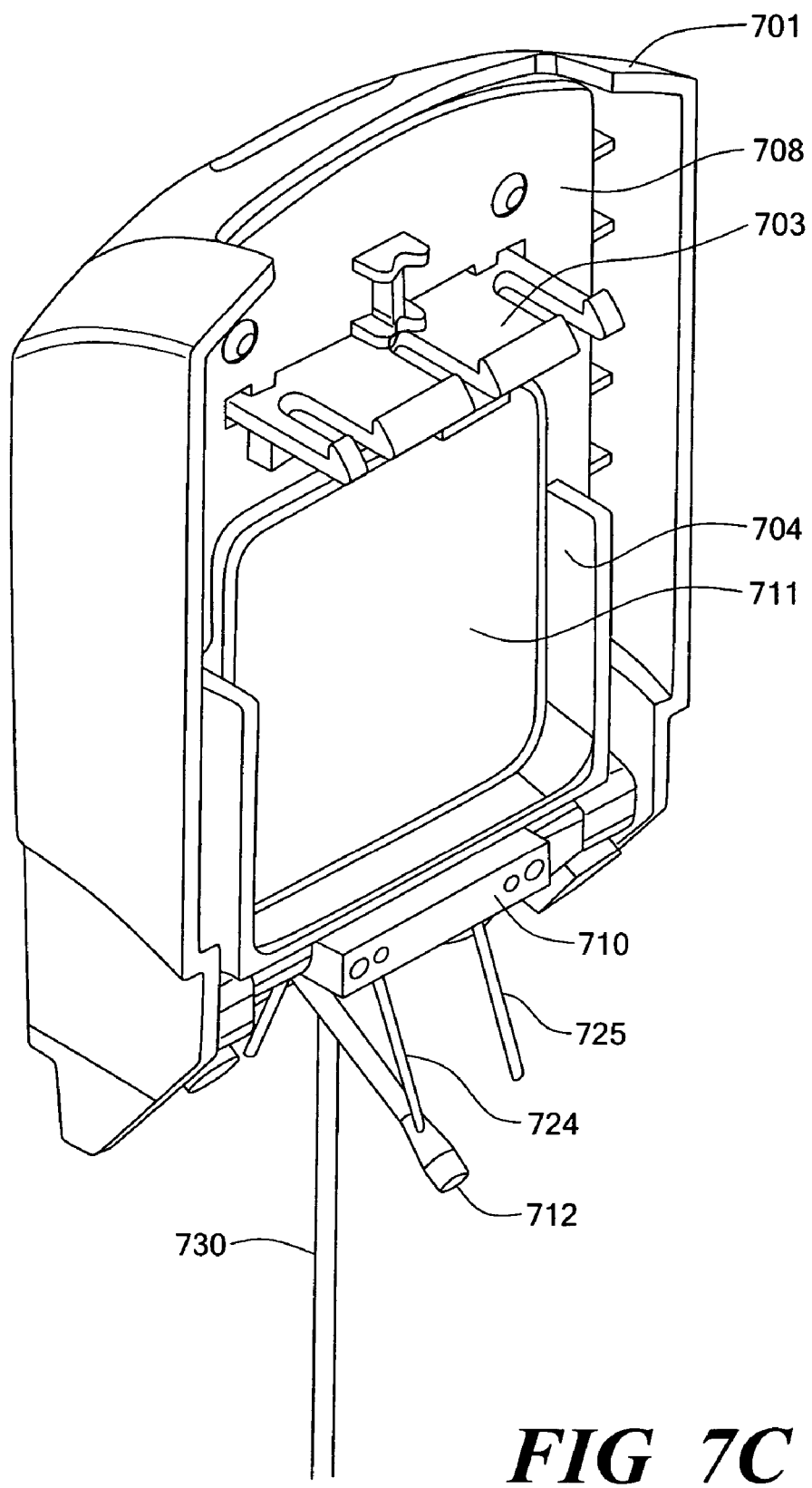
FIG. 7C shows a rear perspective view of the door assembly shown in FIG. 7A in accordance with an embodiment of the present invention, in which the cassette receptacle is in a retracted position.

FIG. 7C shows a rear perspective view of the door assembly 402 in accordance with an embodiment of the present invention, in which the cassette receptacle 704 is in a retracted position. Visible at the rear of the door cowl 701 are the frame 708, the latch portion of the door latch 703, the cassette receptacle 704, the piston assembly 711, the door mounting bracket 710, the torsion springs 724 and 725, a portion of the human interface board assembly 712, and a portion of the pneumatic circuit 730.

Figure 7D:
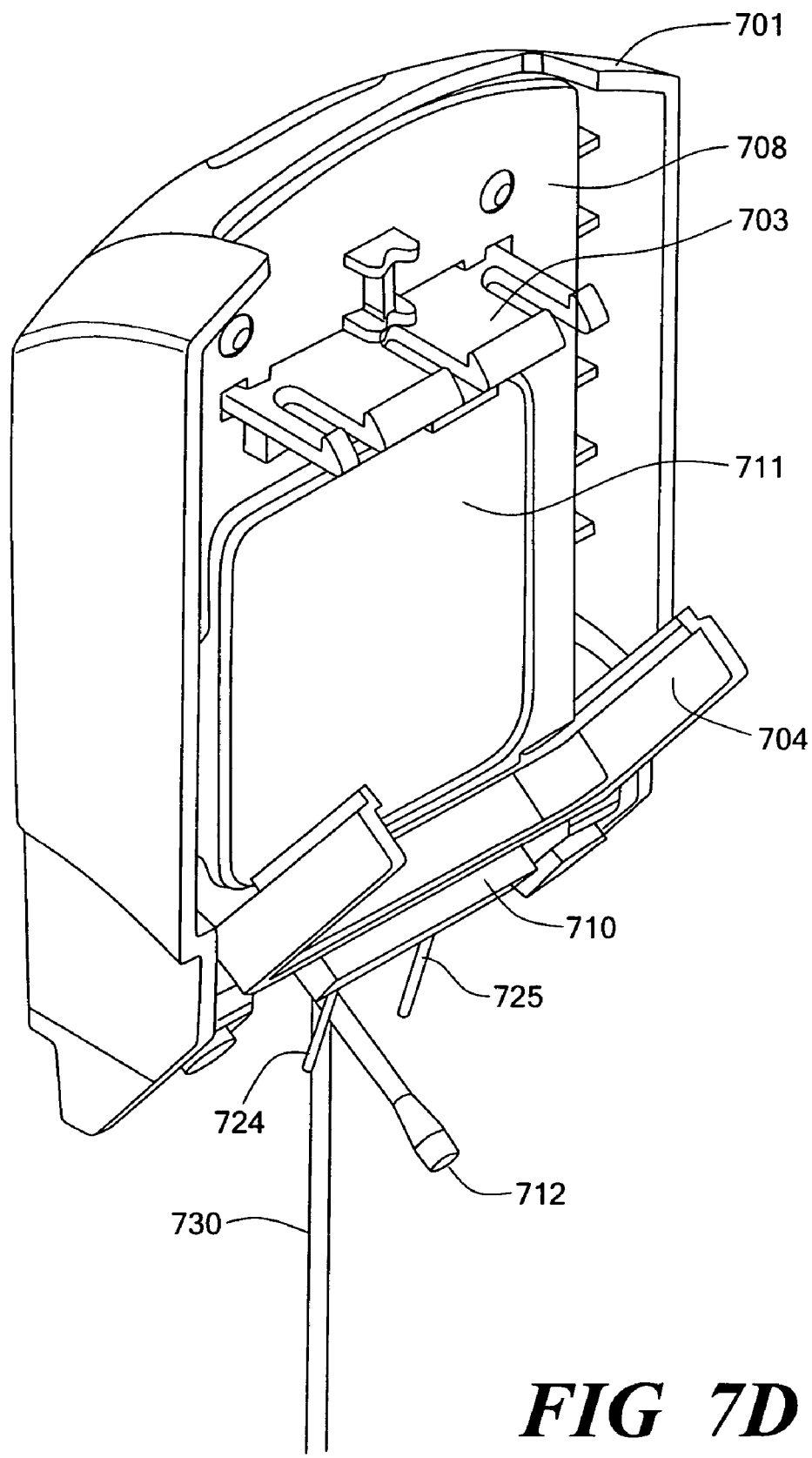
FIG. 7D shows a rear perspective view of the door assembly shown in FIG. 7A in accordance with an embodiment of the present invention, in which the cassette receptacle is in an open position.

FIG. 7D shows a rear perspective view of the door assembly 402 in accordance with an embodiment of the present invention, in which the cassette receptacle 704 is in an open position. Visible at the rear of the door cowl 701 are the frame 708, the latch portion of the door latch 703, the cassette receptacle 704, the piston assembly 711, the door mounting bracket 710, the torsion springs 724 and 725, a portion of the human interface board assembly 712, and a portion of the pneumatic circuit 730.

Occluder Assembly

The occluder assembly 404 is used to occlude various tubes as needed for testing, compounding, and protection in the event of a failure. The occluder assembly 404 includes an occluder blade, an occluder spring, a two-piece sheet metal enclosure, an occluder bladder, guide bushings, connectors, spacers, shafts, and miscellaneous hardware. The occluder assembly 404 for the compounder 102 includes a single occluder blade. The occluder assembly 404 includes a bladder that, when inflated, retracts the occluder, which enables fluid to pass through the tubing. In the event of a loss of pneumatics, the occluder assembly 404 defaults to the occluded position so as to prevent fluid from passing through the tubing. The occluder assembly 404 is mounted to the front plate assembly 408, and provides a mounting point for the vial spike assembly 406.

Figure 8A:
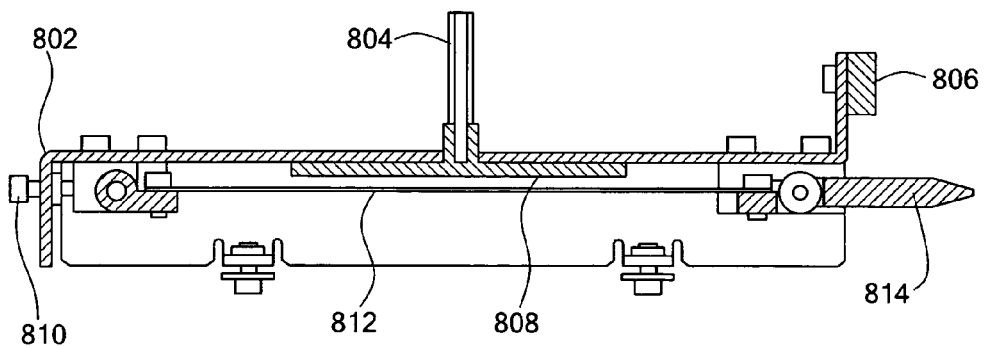
FIG. 8A shows a cross-sectional view of an occluder assembly in accordance with an embodiment of the present invention.

FIG. 8A shows a cross-sectional view of an occluder assembly 404 in accordance with an embodiment of the present invention. Among other things, the occluder assembly 404 includes a housing 802, tubing 804 connected to a bladder 808, a spacer 806 coupled to the front of the housing 802, an occluder blade 814, an occluder spring 812, and an adjuster 810. The occluder spring 812 is essentially a flat spring. The occluder blade 814 is connected to the end of the occluder spring 812. When the bladder 808 is inflated, the occluder spring 812 is deflected downward at the middle so as to shorten the effective length of the occluder spring 812 and retract the occluder blade 814. When the bladder 808 is deflated, the occluder spring 812 extends flat and therefore extends the occluder blade 814.

Figure 8B:
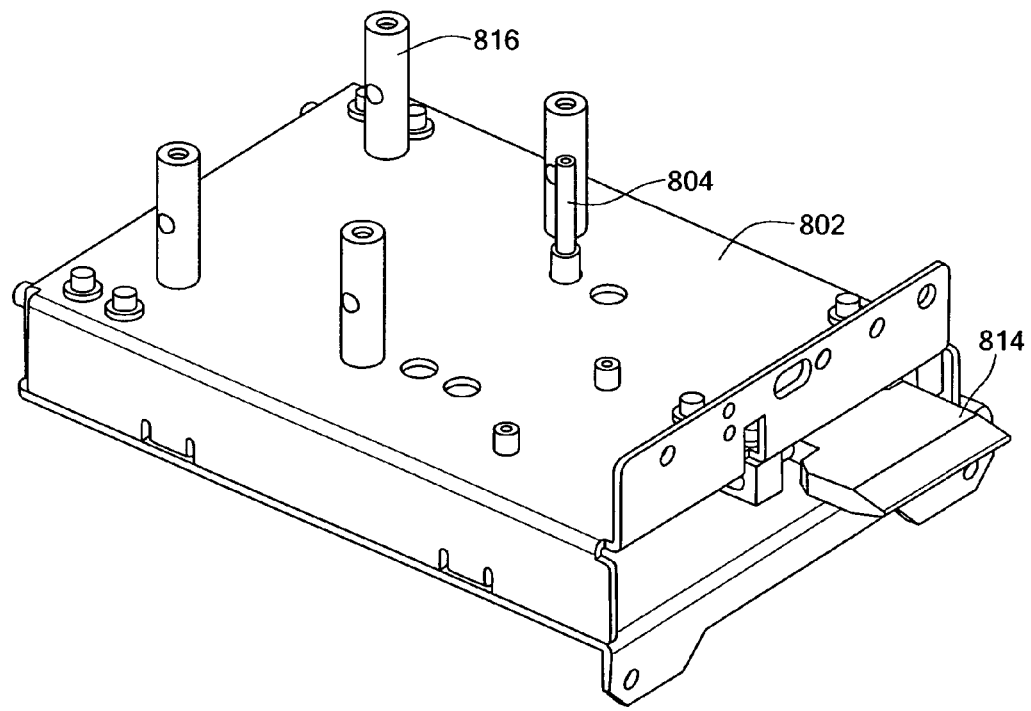
FIG. 8B shows a side perspective view of the occluder assembly shown in FIG. 8A in accordance with an embodiment of the present invention.

FIG. 8B shows a side perspective view of the occluder assembly 404 in accordance with an embodiment of the present invention. The housing 802, the tubing 804, the occluder blade 814, and various standoffs 816 are shown.

Figure 8C:
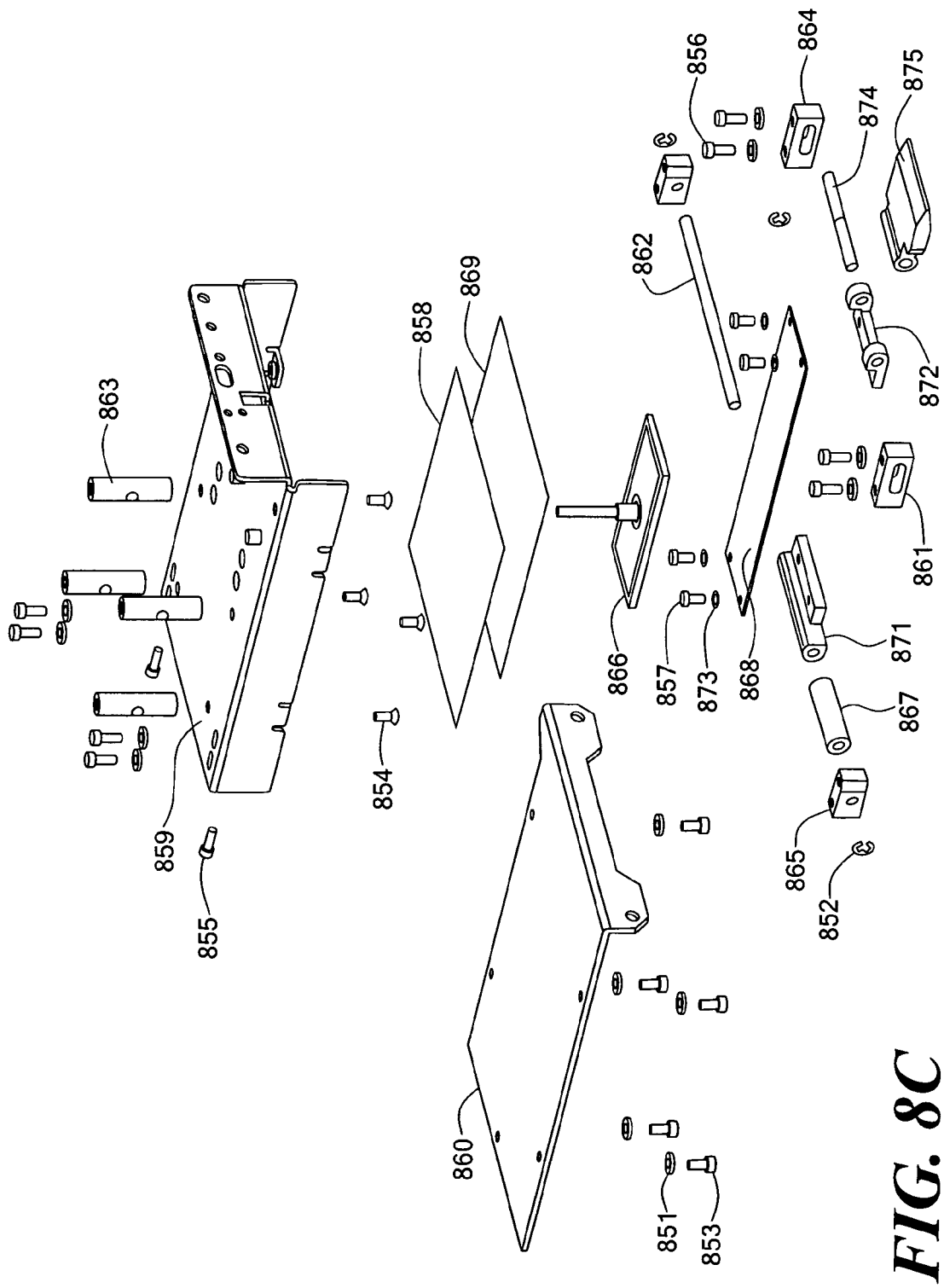
FIG. 8C shows an exploded view of the occluder assembly shown in FIG. 8A in accordance with an embodiment of the present invention.

FIG. 8C shows an exploded view of the occluder assembly 404 in accordance with an embodiment of the present invention. The occluder assembly 404 includes an occluder blade 875, a shaft 874, a front bracket 872, a rear bracket 871, a mylar sheet 869, a spring 868, a shaft spacer 867, an occluder bladder 866, rear blocks 865, sliding blocks 864 and 861, four spike standoffs 863, a rear shaft 862, an enclosure bottom 860, an enclosure top 859, double coated tape 858, three E-rings 852, and various hardware, 873, 857, 856, 855, 854, 853, and 851. The occluder blade 875 mounts to the front bracket 872 via the shaft 874. The rear bracket 871 is mounted to the enclosure top 859 via shaft 862, blocks 865, spacer 867, and clamps 852. The rear bracket 871 is held in a substantially fixed position, although the rear bracket 871 is able to rotate about the shaft 862 as needed for operation of the occluders. The front bracket 872 is mounted to the enclosure top 859 via shaft 874 and sliding blocks 861 and 864. The front bracket 872 is able to slide forward and backward along channels formed in the sliding blocks 861 and 864 as needed for operation of the occluders. Thus, the blocks 865 constrain the position of the occluder blade and act as bearing surfaces as the rear shaft rotates, and the sliding blocks 861 and 864 act as bearing surfaces for the front shaft as the occluder blade is actuated and released. It should be noted that the present invention is not limited to the block-type bearings shown, but rather various types of bushings, bearings, fixed blocks, moving blocks, or any combination thereof could be used to permit rotation of the rear shaft and/or brackets and translational movement of the front shaft. The occluder blade 875 can be manually retracted if necessary. The edge of the occluder blade 875 that engages the tubing is typically rounded so as not to cut or crease the tubing.

Vial Spike Assembly

The vial spike assembly 406 is used to join the vial assembly 200 with the spike receptacle 310 so as to cause spiking of the vial. The vial spike assembly 406 is preferably positioned so as to protrude through the top of the compounder 102. This provides easy access to the vial spike assembly 406 for inserting and removing the vial assembly 200 and spike receptacle 310 in support of compounding operations.

Figure 9A:
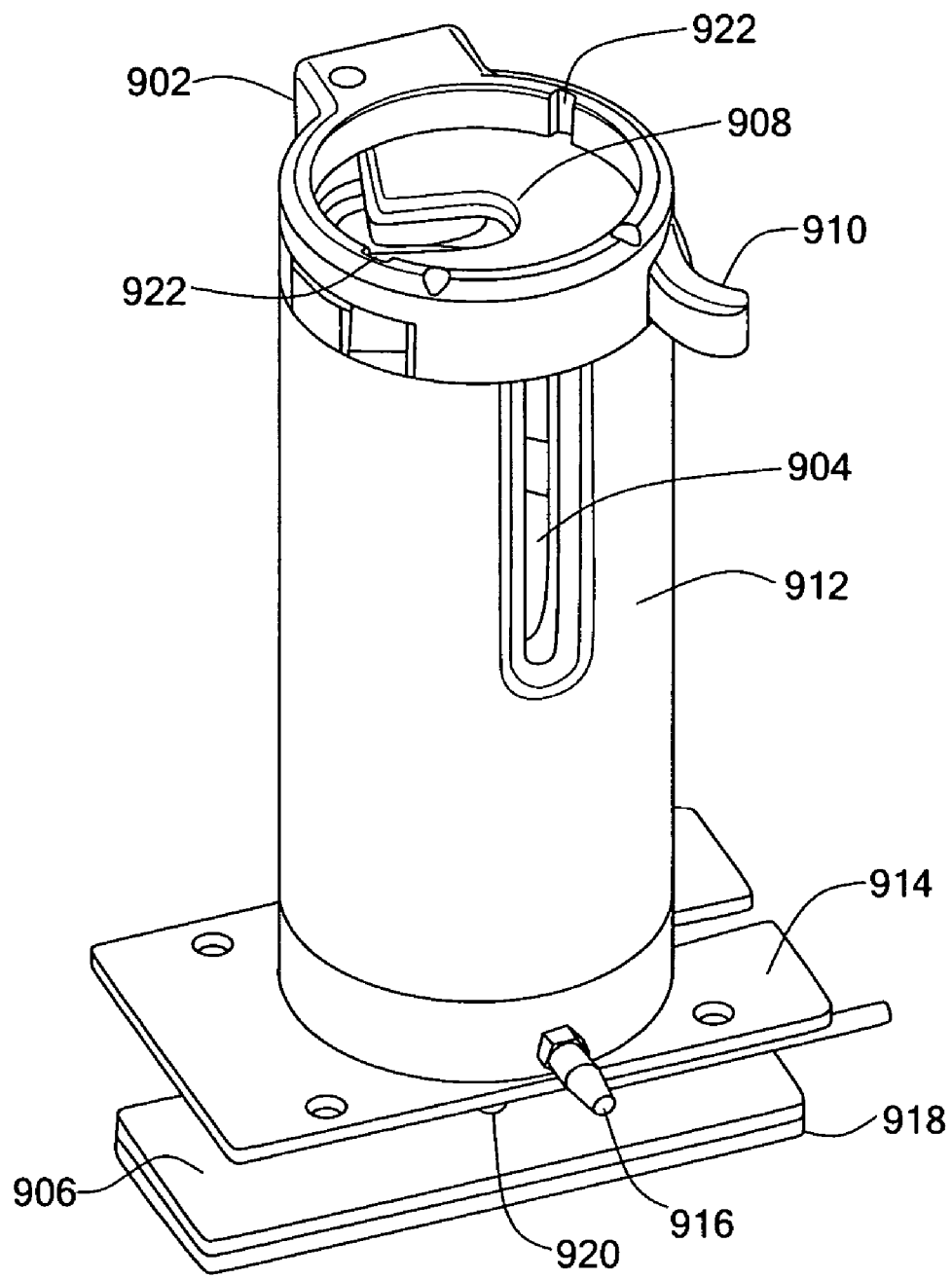
FIG. 9A shows an exemplary vial spike assembly in accordance with an embodiment of the present invention.

FIG. 9A shows an exemplary vial spike assembly 406 in accordance with an embodiment of the present invention. The vial spike assembly 406 includes a cylinder 912 for receiving the vial assembly 200 and the spike receptacle 310, a base 914 for supporting the cylinder 912, a piston 904 operating within the cylinder and connected to a bladder plate 906 by a shaft 920, a bladder 918 for controlling movement of the piston 904 within the cylinder 912 by operating on the bladder plate 906, three switches (sensors) for sensing the presence and position of the vial assembly 200 and spike receptacle 310 (one of which is shown as switch 908, and the other two located within the cylinder 912 and shown in later figures), a sensor cover 902, a spike cover 910 acting as a locking mechanism and including switch 908 that is operated by the sensor feature 346 of the spike receptacle 310, a drain port 916, and associated plumbing and mounting hardware (not shown).

In order to perform spiking to allow for dilution of the anti-pathogen compound, the vial assembly 200 is first inserted into the cylinder 912. Sensors in the cylinder 912 detect the presence of the vial assembly 200 within the cylinder 912 and also the position of the vial assembly 200 within the cylinder 912.

Once the vial assembly 200 is in place within the cylinder 912, the spike receptacle 310 is inserted into the cylinder 912. As the spike receptacle 310 is installed in the cylinder 912, the fit between the spike receptacle housing 344 and the inner wall of the cylinder 912 causes the release tabs 358 on the spike guard 360 to move inward so as to release the guard 360. This enables the guard 360 to move easily. The spike cover 910 is then closed. The switch 908 in the cover 910 is engaged by the sensor feature 346 of the spike receptacle 310 and so detects the presence of the spike receptacle 310 and also closure of the cover 910.

Figure 9B:
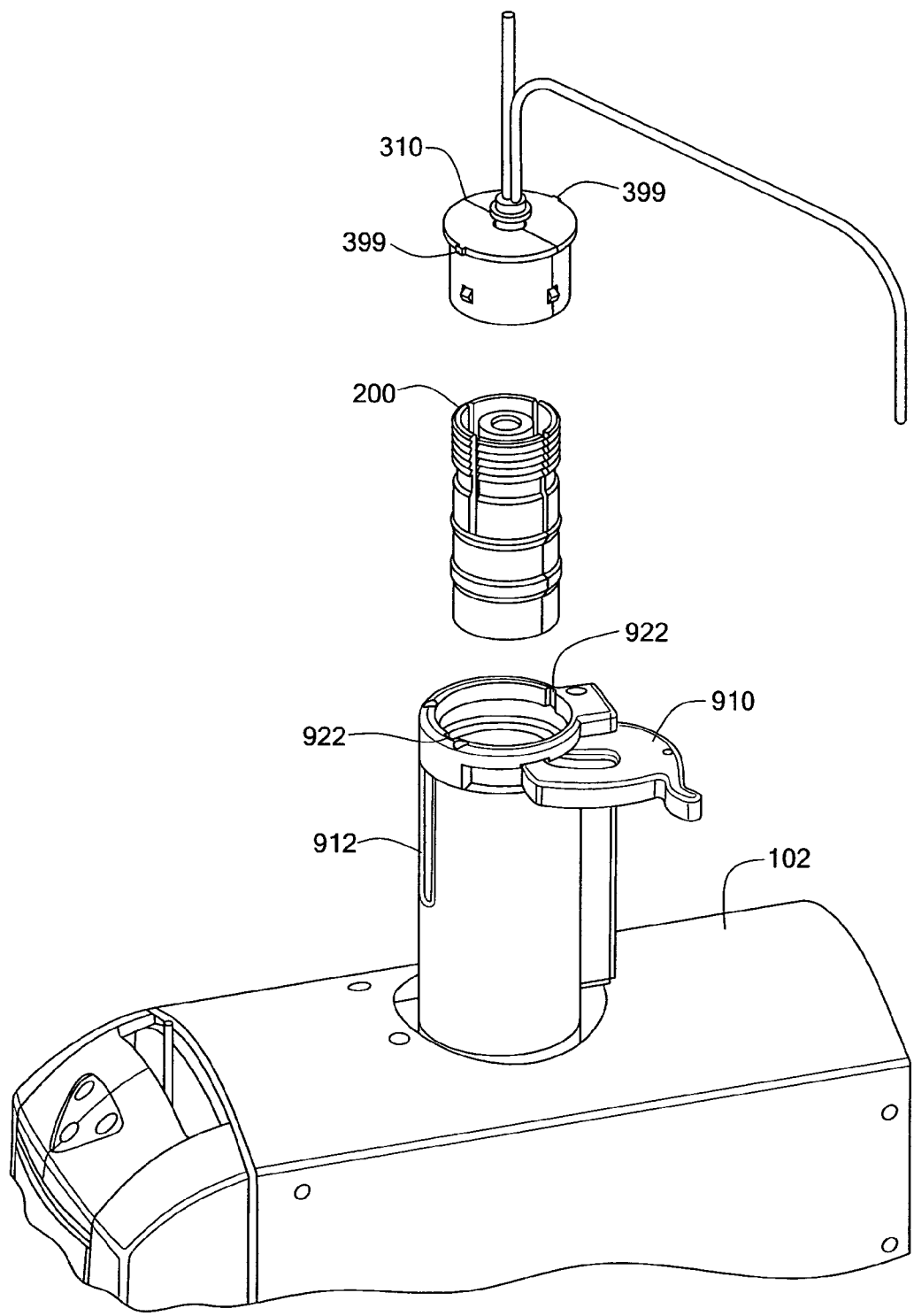
FIG. 9B is a schematic diagram showing the vial spike assembly shown in FIG. 9A prepared for insertion of the vial assembly and the spike receptacle in accordance with an embodiment of the present invention.

FIG. 9B is a schematic diagram showing the vial spike assembly 406 prepared for insertion of the vial assembly 200 and the spike receptacle 310 in accordance with an embodiment of the present invention. The cylinder 912 and cover 910 are shown, with the cover 910 in an open position so that the vial assembly 200 and spike receptacle 310 can be inserted into the cylinder 912. The spike receptacle 310 includes orientation tabs 399 that align with orientation slots 922 in the cylinder 912.

Figure 9C:
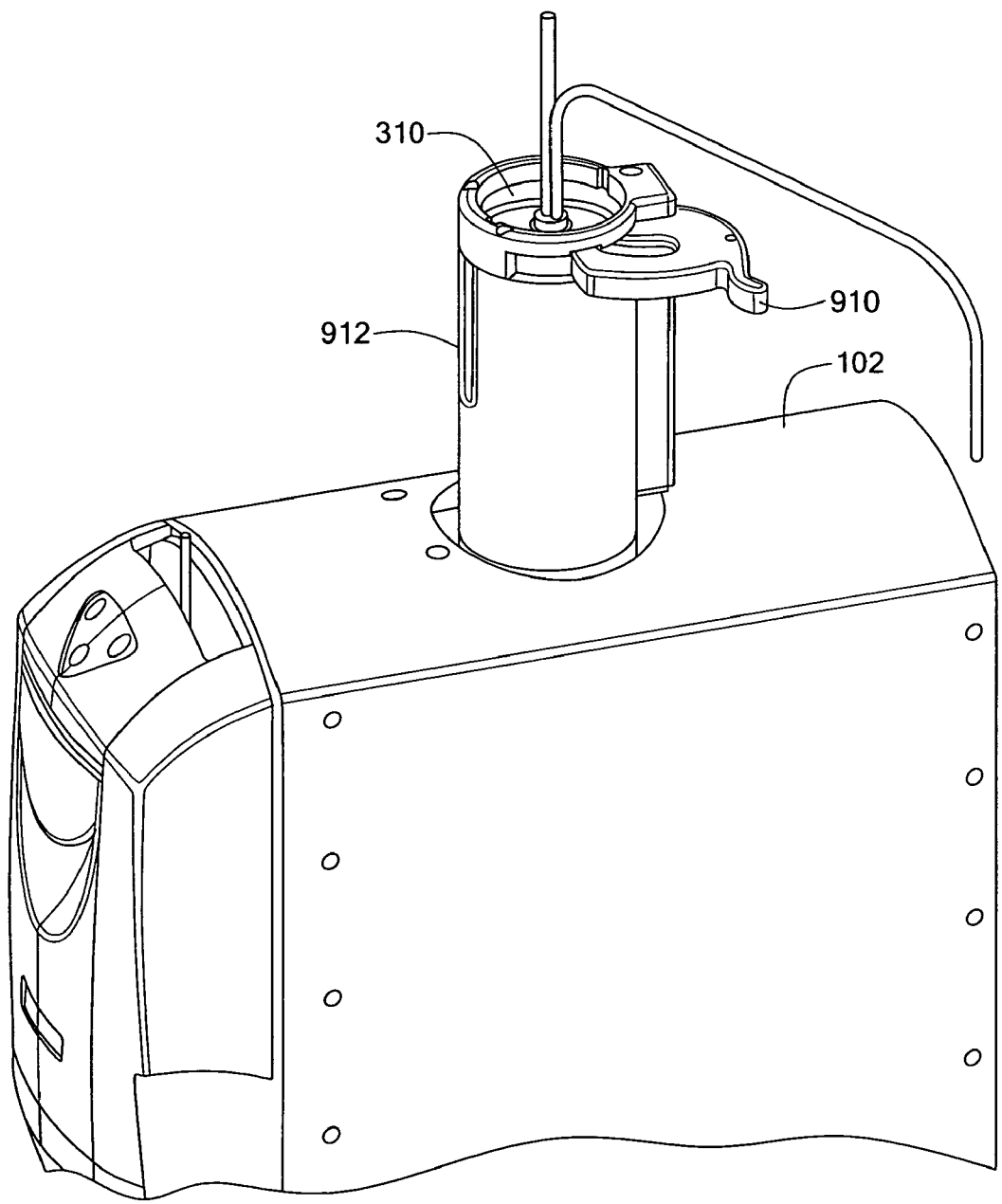
FIG. 9C is a schematic diagram showing the vial spike assembly shown in FIG. 9A with the vial assembly and spike receptacle inserted into the cylinder and the cover in an open position in accordance with an embodiment of the present invention.

FIG. 9C is a schematic diagram showing the vial spike assembly 406 with the vial assembly 200 and spike receptacle 310 inserted into the cylinder 912 and the cover 910 in an open position in accordance with an embodiment of the present invention. In this configuration, the sensors in the cylinder will detect the presence of the vial assembly 200 within the cylinder 912 and will also detect that the vial assembly 200 is in a pre-spiking position within the cylinder 912. The switch 908 will not detect presence of the spike receptacle 310 within the cylinder 912, as the cover 910 is in the open position.

Figure 9D:
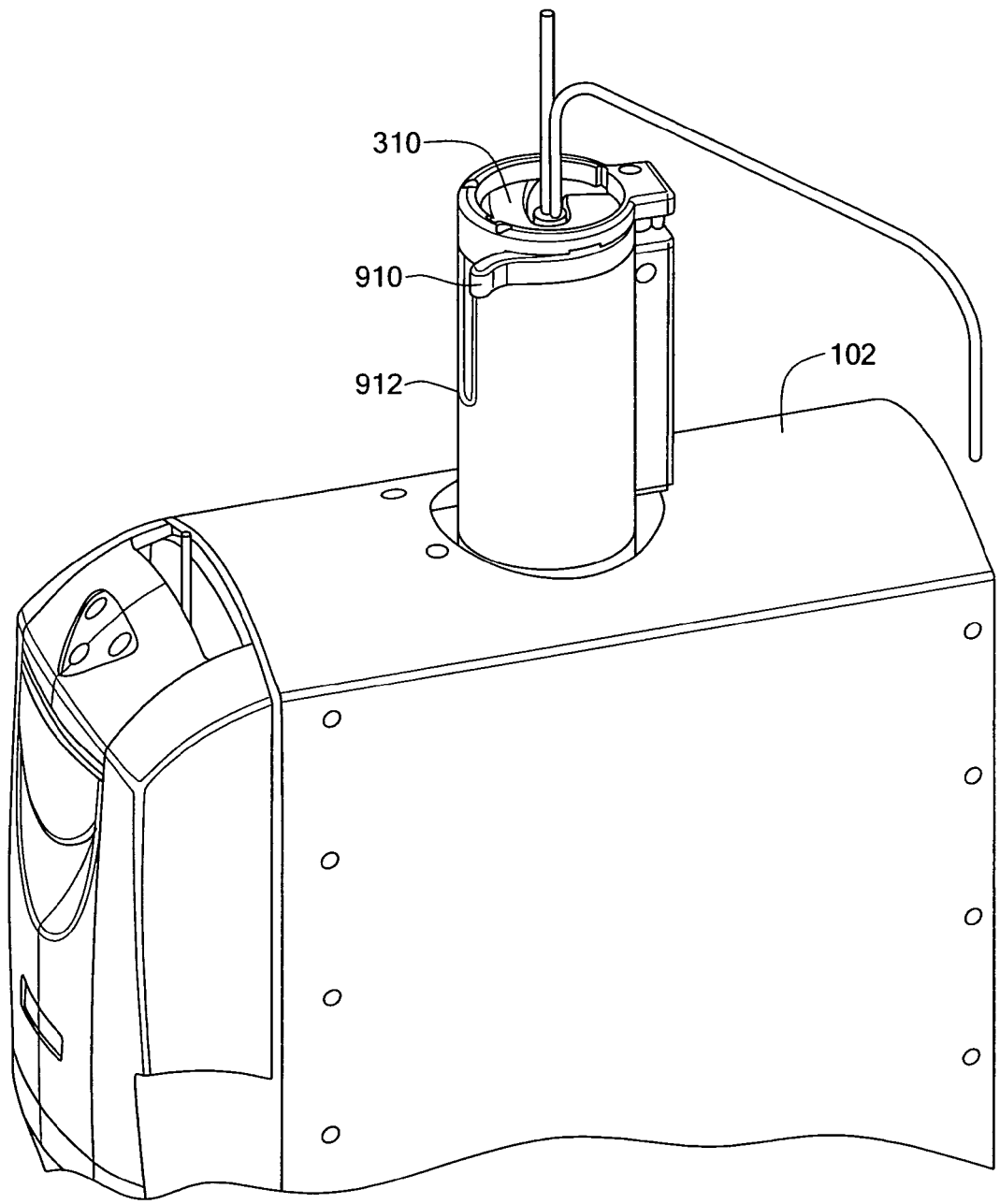
FIG. 9D is a schematic diagram showing the vial spike assembly shown in FIG. 9A with the vial assembly and spike receptacle inserted into the cylinder and the cover in a closed position in accordance with an embodiment of the present invention.

FIG. 9D is a schematic diagram showing the vial spike assembly 406 with the vial assembly 200 and spike receptacle 310 inserted into the cylinder 912 and the cover 910 in a closed position in accordance with an embodiment of the present invention. In this configuration, the switch 908 will indicate presence of the spike receptacle 310 within the cylinder 912 and closure of the cover 910.

Figure 9E:
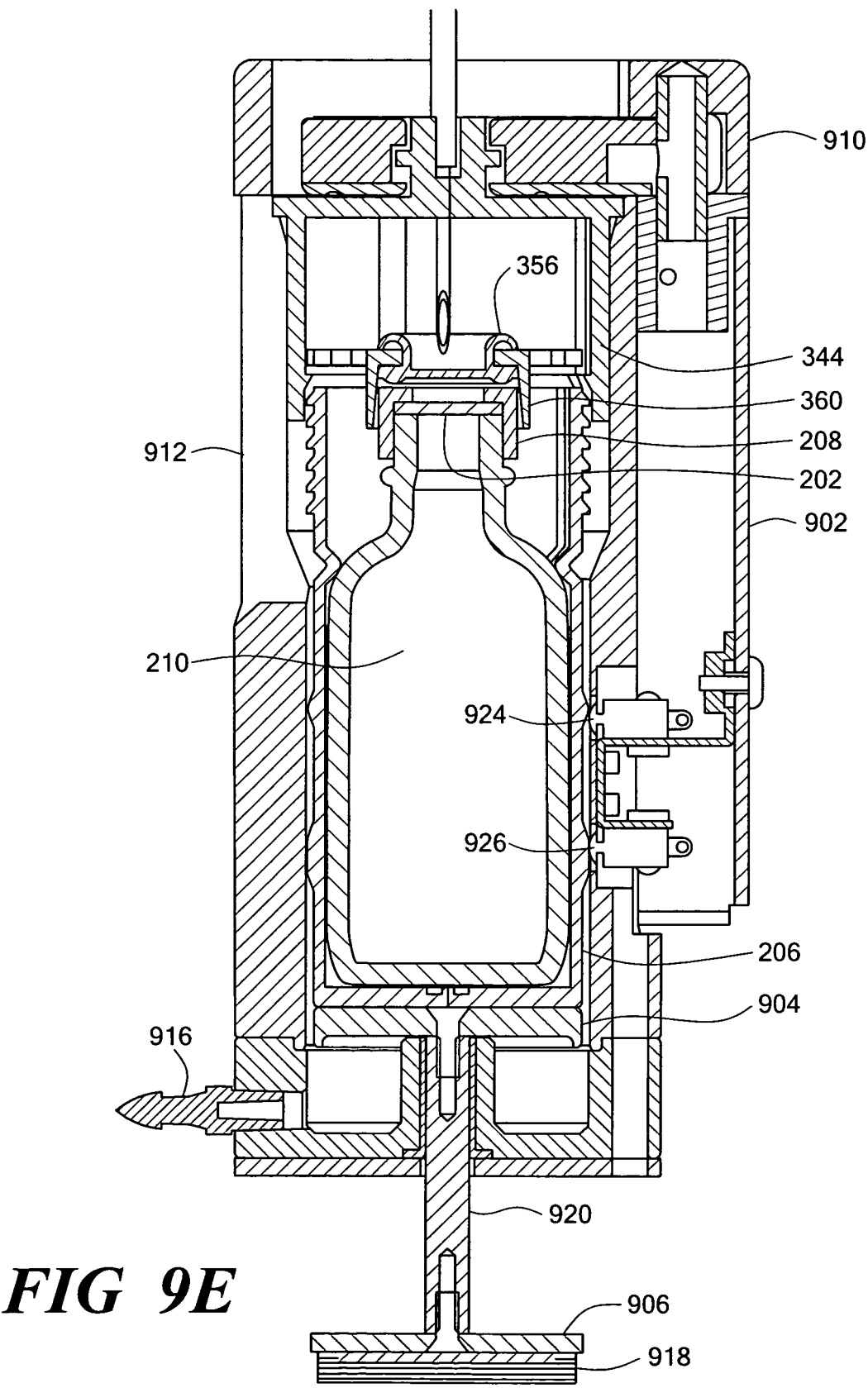
FIG. 9E shows a cross-sectional view of the vial spike assembly with the vial assembly and spike receptacle locked and loaded and ready for spiking, in accordance with an embodiment of the present invention.

FIG. 9E shows a cross-sectional view of the vial spike assembly 406 with the vial assembly 200 and spike receptacle 310 locked and loaded and ready for spiking, in accordance with an embodiment of the present invention. The vial receptacle 206 carrying the vial 210 with vial cap 208 and vial septum 202 is positioned within the cylinder such that a vial loaded sensor 926 is actuated and a vial spiked sensor 924 is not actuated by the switch engagement features 214. The spike housing 344 is locked by cover 910 such that the spike guard 360 with grommet 356 is aligned with the vial cap 208. The bladder 918 is deflated so that the bladder plate 906, shaft 920, and piston 904 are retracted.

Once the vial assembly 200 and spike receptacle 310 are positioned and locked in place, the bladder 918 can be inflated to cause the bladder plate 906 to push the shaft 920 and piston 904 upward. This forces the vial assembly 200 upward into the spike receptacle 310, causing spiking of the vial. The sensors in the cylinder 912 detect the movement of the vial assembly 200 and completion of the spiking operation. The sensors can also detect incomplete spiking, for example, insufficient movement of the vial assembly 200, in which case an anomaly signal is typically sent to the process controller 120.

Figure 9F:
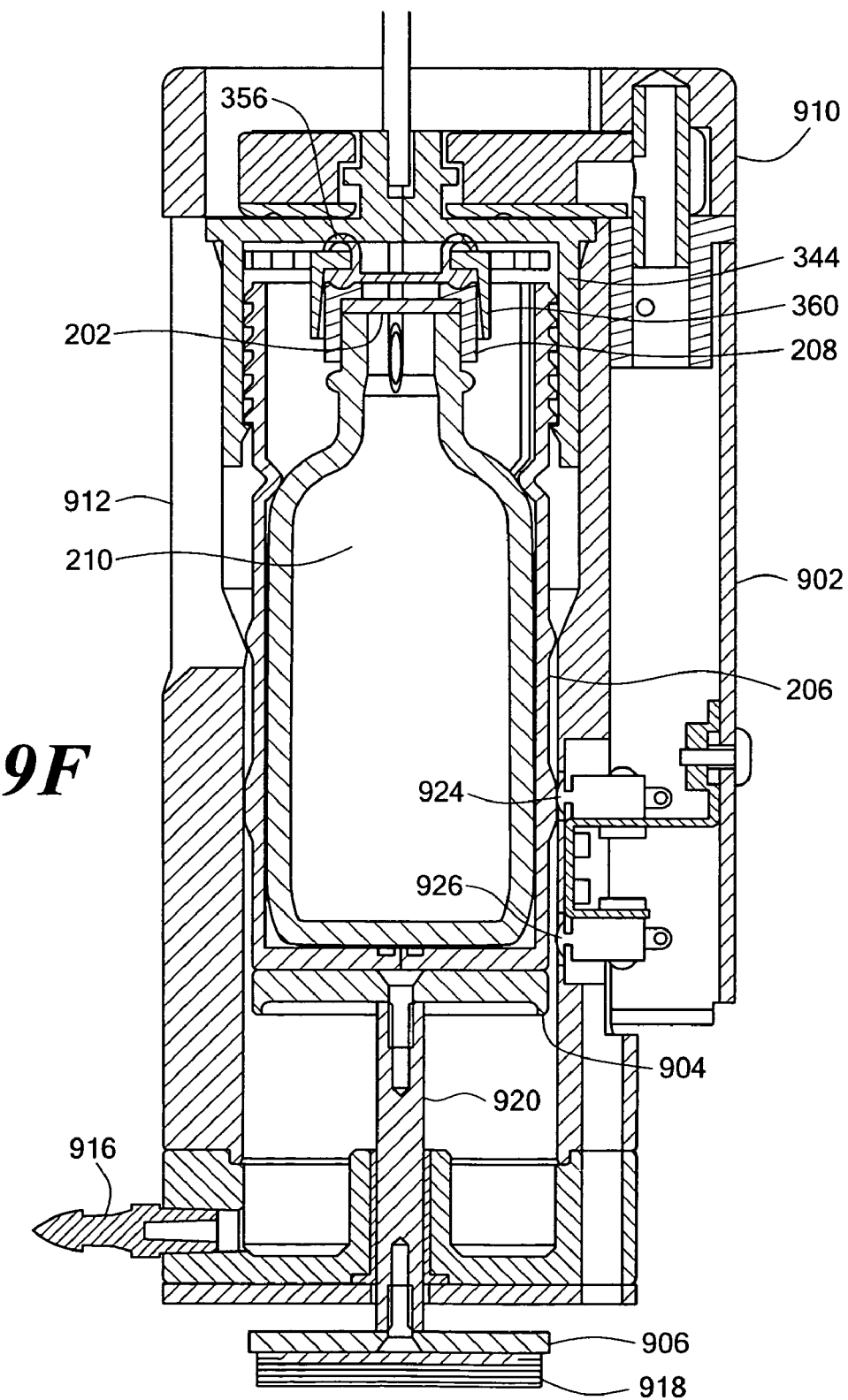
FIG. 9F shows a cross-sectional view of the vial spike assembly after spiking is completed, in accordance with an embodiment of the present invention.

FIG. 9F shows a cross-sectional view of the vial spike assembly 406 after spiking is completed, in accordance with an embodiment of the present invention. The bladder 918 is inflated so that the bladder plate 906, shaft 920, and piston 904 have pushed the vial receptacle 206 carrying the vial 210 with vial cap 208 and vial septum 202 up and into the spike housing 344, which is held in place by the cover 910. With the vial receptacle 206 in this position, the vial loaded sensor 926 is not actuated and the vial spiked sensor 924 is actuated by the switch engagement features 214. During the spiking operation, the spike guard 360 with grommet 356 was also pushed upward along with the vial receptacle 206, and the grommet 356 is pressed tightly against the vial cap 206 so as to provide a secondary seal for the spikes in case fluid were to leak through the septum 202 around the spikes 354 during pumping.

When the spiking operation is complete, the bladder 918 can be deflated. The vial assembly 200 and the spike receptacle 310 will be permanently connected, specifically by the engagement of the spike receptacle engagement teeth 204 on the vial receptacle 206 with the vial receptacle locking feature 348 of the spike receptacle 310. The vial assembly 200 and spike receptacle 310 can be removed from the cylinder by pull on the tubing that connects to the spike receptacle 310. As discussed above, the tubing is strongly attached to the spike receptacle 310 and so will not disengage from the spike receptacle 310.

Figure 10:
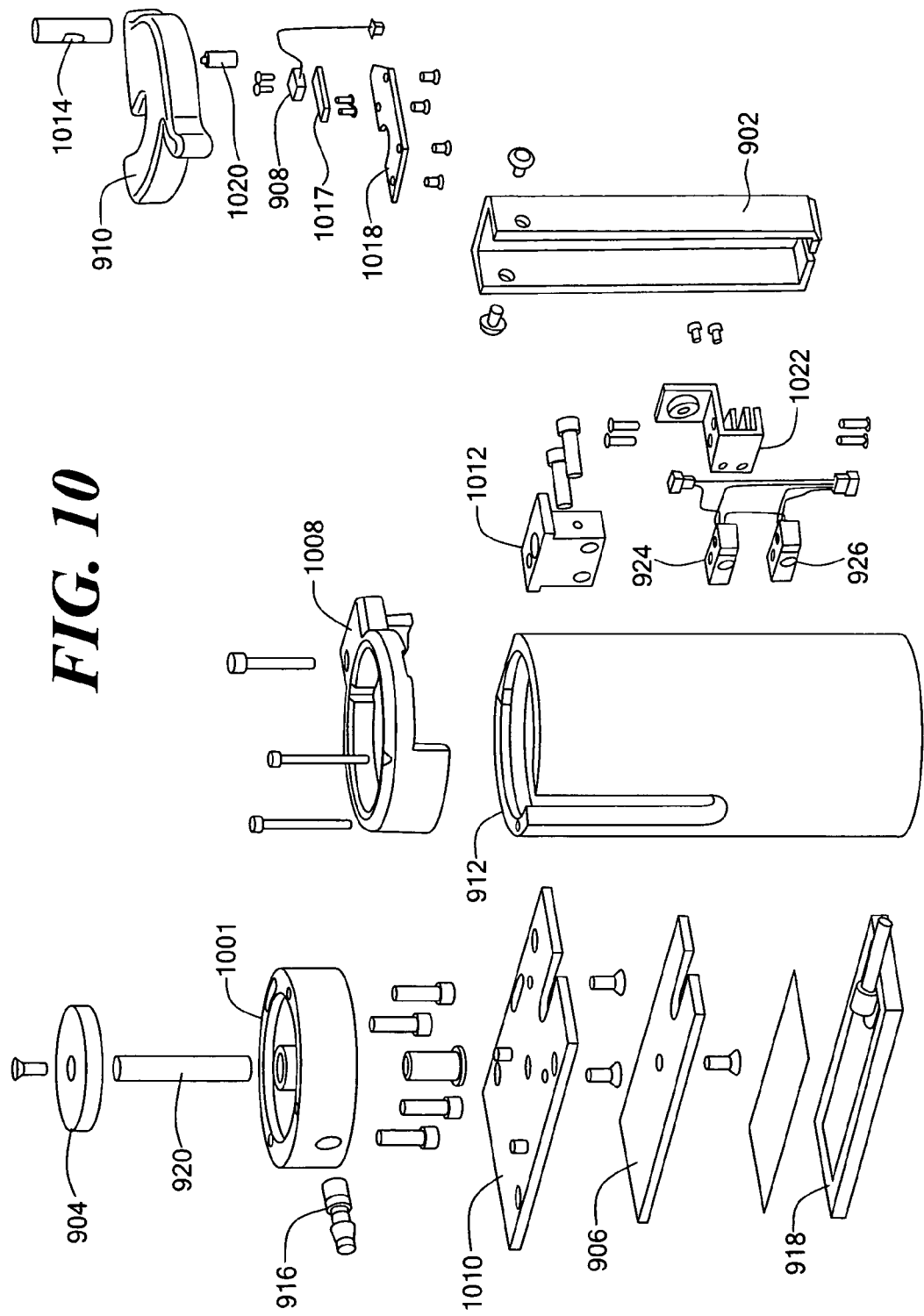
FIG. 10 shows an exploded view of the vial spike assembly shown in FIG. 9A in accordance with an embodiment of the present invention.

FIG. 10 shows an exploded view of the vial spike assembly 406 in accordance with an embodiment of the present invention. Among other things, the vial spike assembly 406 includes a cylinder base 1001, a spike cylinder 912, a piston 904, a shaft 920, a bladder plate 906, a spike cover guide 1008, a spike cylinder base 1010, a bladder 918, a cover bracket 1012, a spike cover 910, an ultra-subminiature snap-action switch 908, a plate 1017, a sensor cover 1018, a plunger 1020, two snap-action enclosed switches 924 and 926, a dual sensor bracket 1022, a sensor channel 902, and assorted hardware (not numbered). The piston 904 is connected to the shaft 920 and is positioned within the spike cylinder 912. The cylinder base 1001 is attached to the bottom of the spike cylinder 912 and to the spike cylinder base 1010. The shaft 920 extends through the cylinder base 1001 and the spike cylinder base 1010 and is attached to the bladder plate 906, which in turn is attached to the bladder 918. The switches 924 and 926 are attached to the dual sensor bracket 1022 and are positioned within corresponding openings in the side of the spike cylinder 912. The sensor channel 902, cover bracket 1012, and spike cover guide 1008 are attached to the spike cylinder 912, with the sensor channel 902 covering the dual sensor bracket 1022. The switch 908 is attached to the spike cover 910 using the plate 1017 and the sensor cover 1018. The spike cover 910 is rotatably coupled to the spike cover guide 1008.

It should be noted that the vial spike assembly 406 can be designed to cause spiking in different ways while remaining within the scope of the present invention. For example, in alternative embodiments of the invention, the vial assembly 200 can be held stationary while the spike receptacle 310 is pushed onto the vial assembly 200 so as to cause spiking. Also, the orientation of the vial assembly 200 and the spike receptacle 310 can be reversed, such that the vial is inverted and the spikes enter the vial from below.

Figure 11:
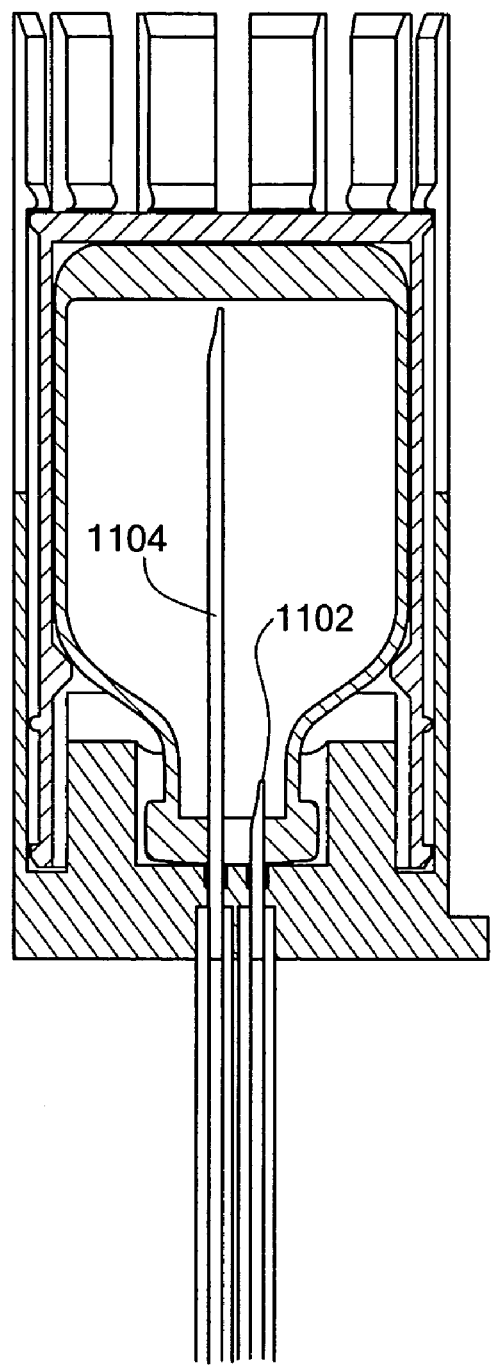
FIG. 11 shows an exemplary spiking mechanism in which the vial is inverted and the spikes enter the vial from below, in accordance with an alternative embodiment of the present invention.

FIG. 11 shows an exemplary spiking mechanism in which the vial is inverted and the spikes enter the vial from below, in accordance with an alternative embodiment of the present invention. In this embodiment, the spikes are of different length, with the shorter spike 1102 acting as the inlet spike and the longer spike 1104 acting as the outlet spike. As buffer solution is added to the vial through the inlet spike 1102, the anti-pathogen compound in the vial becomes partially diluted. When the vial fills with fluid past the hollow of the outlet spike 1104, the diluted solution flows out the outlet spike 1104 to the working solution container.

Chassis Components

The chassis components 414 include various mechanical hardware components that are not considered part of the other assemblies. Among other things, the chassis components 414 include the DC air pump 511, a chassis base, a door sensor (and cable), mounting foot grommets, skins (housing), and associated hardware and fasteners. The housing includes a mounting point, on the back of the unit, for the manual piston bladder (door) vent 503.

Compounding

As discussed above, the compounder 102 and the blood pumps 104 operate under control of the process controller 120. In exemplary embodiments of the present invention, introduction of the anti-pathogen compound into the RBCC is performed in two stages, a first stage in which the anti-pathogen compound is mixed with buffer solution to a first concentration, and a second stage in which the working solution is mixed with the RBCC to a second concentration. The two-stage process is described in more detail in Application D72.

Figure 12:
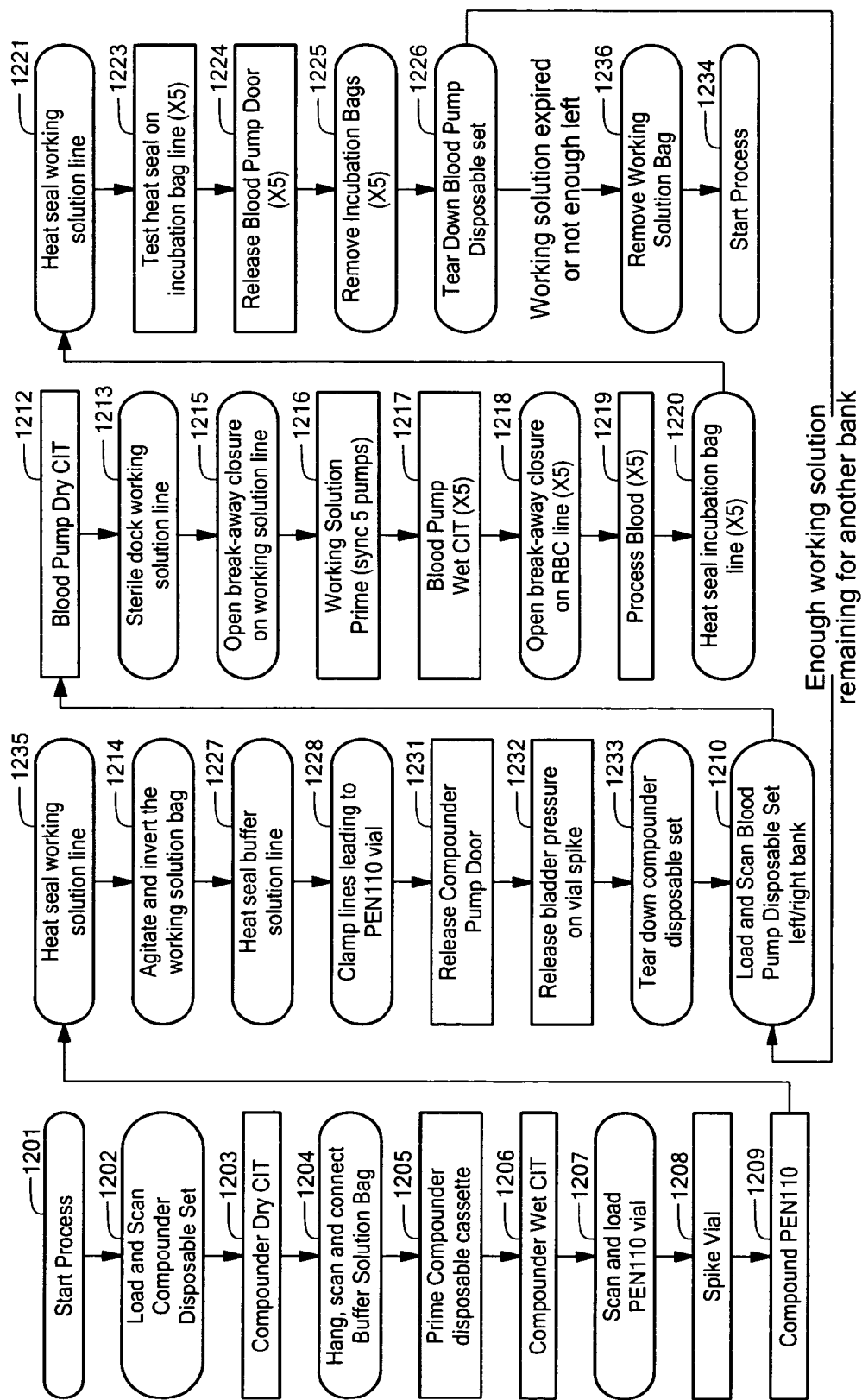
FIG. 12 shows a process flow diagram describing the compounding and blood treatment process in accordance with an embodiment of the present invention.

FIG. 12 shows a process flow diagram describing the compounding and blood treatment process in accordance with an embodiment of the present invention. Rectangular blocks indicate commands sent to the pump by the process controller 120. Rounded blocks indicate instructions sent to the operator by the process control 120.

The process starts in block 1201. In block 1202, the process controller instructs the operator to load and scan a compounder disposable set. After the compounder disposable set is loaded into the compounder, the process controller instructs the compounder to run a dry cassette integrity test (CIT) in block 1203. The compounder dry CIT is described in more detail with reference to FIG. 14 below. Assuming the dry CIT is acceptable, the process controller instructs the operator to hang, scan, and connect the buffer solution bag so that the buffer solution bag is connected to the inlet port of the pump cassette, in block 1204. The process controller then instructs the compounder to prime the compounder disposable set, in block 1205. Compounder priming is described in more detail with reference to FIG. 15 below. The process controller then instructs the compounder to run a wet CIT, in block 1206. The compounder wet CIT is described in more detail below with reference to FIG. 16. Assuming the wet CIT is acceptable, the process controller then instructs the operator to scan and load the vial assembly and spike receptacle into the vial spike assembly, in block 1207. The process controller then instructs the compounder to spike the vial, in block 1208. Once spiking is completed, the process controller instructs the compounder to perform the compounding operation, in block 1209.

As discussed above, compounding involves drawing buffer solution from the buffer solution container and pumping the buffer solution to the vial to dilute the anti-pathogen compound and pump the working solution to the working solution container. The compounder measures the volume of buffer solution pumped to the vial so that the resulting working solution will have a predetermined concentration of anti-pathogen compound, within predetermined limits. After compounding is complete, the vial will contain some amount of fluid including buffer solution and perhaps a very small amount of anti-pathogen compound.

After compounding is complete, the process controller coordinates "teardown" of the compounder for removal and disposal of the compounder disposable set from the compounder. Specifically, with reference again to FIG. 12, the process controller instructs the operator to heat seal the working solution line, in block 1235, and then agitate and invert the working solution bag, in block 1214. The process controller then instructs the operator to heat seal the buffer solution line, in block 1227. The process controller then instructs the operator to clamp the lines leading to the vial, in block 1228. The process controller then instructs the compounder to release the compounder door, in block 1231, which is accomplished by deflating the bladder in the door assembly. The process controller then instructs the compounder to release the bladder pressure on the vial spike (piston), in block 1232. The process controller then instructs the operator to remove the compounder disposables from the compounder 1233.

After compounder "teardown" is complete, the process controller coordinates the blood processing operations in which the RBCC is mixed with working solution by the blood pumps 104 in order to produce the incubation solutions. Specifically, the process controller instructs the operator to load and scan a blood pump disposable set in a bank of blood pumps, in block 1210, and runs a blood pump dry cassette integrity test (CIT), in block 1212. The process controller then instructs the operator to connect the disposable set to the working solution line using the sterile dock, in block 1213, and to open the break-away closure on the working solution line, in block 1215. The process controller then primes the blood pumps with working solution, in block 1216, and runs a blood pump wet CIT on each of the blood pumps, in block 1217. The process controller then instructs the operator to open the break-away closure on each of the RBCC lines, in block 1219, and then operates each of the blood pumps to mix RBCC with working solution to produce incubation solution, in block 1219. When blood processing is complete, the process controller instructs the operator to heat seal each of the incubation bag lines, in block 1220, and also to heat seal the working solution line, in block 1221. The process controller then tests the heat seal on the incubation bag lines, in block 1223, and then instructs each of the blood pumps to release the door (by deflating the door bladder), in block 1224. The process controller then instructs the operator to remove each of the incubation bags, in block 1225, and tear down the blood disposable set, in block 1226. Blood processing operations are described in greater detail in Application D71.

If there is enough working solution remaining for another blood processing cycle, then the process may recycle to block 1210 to coordinate blood processing operations for another bank of blood pumps. If and when the working solution has expired or there is not enough working solution remaining for another blood processing cycle, then the process controller typically instructs the operator to remove the working solution bag, in block 1236. The process ends in block 1234.

Figure 13A:
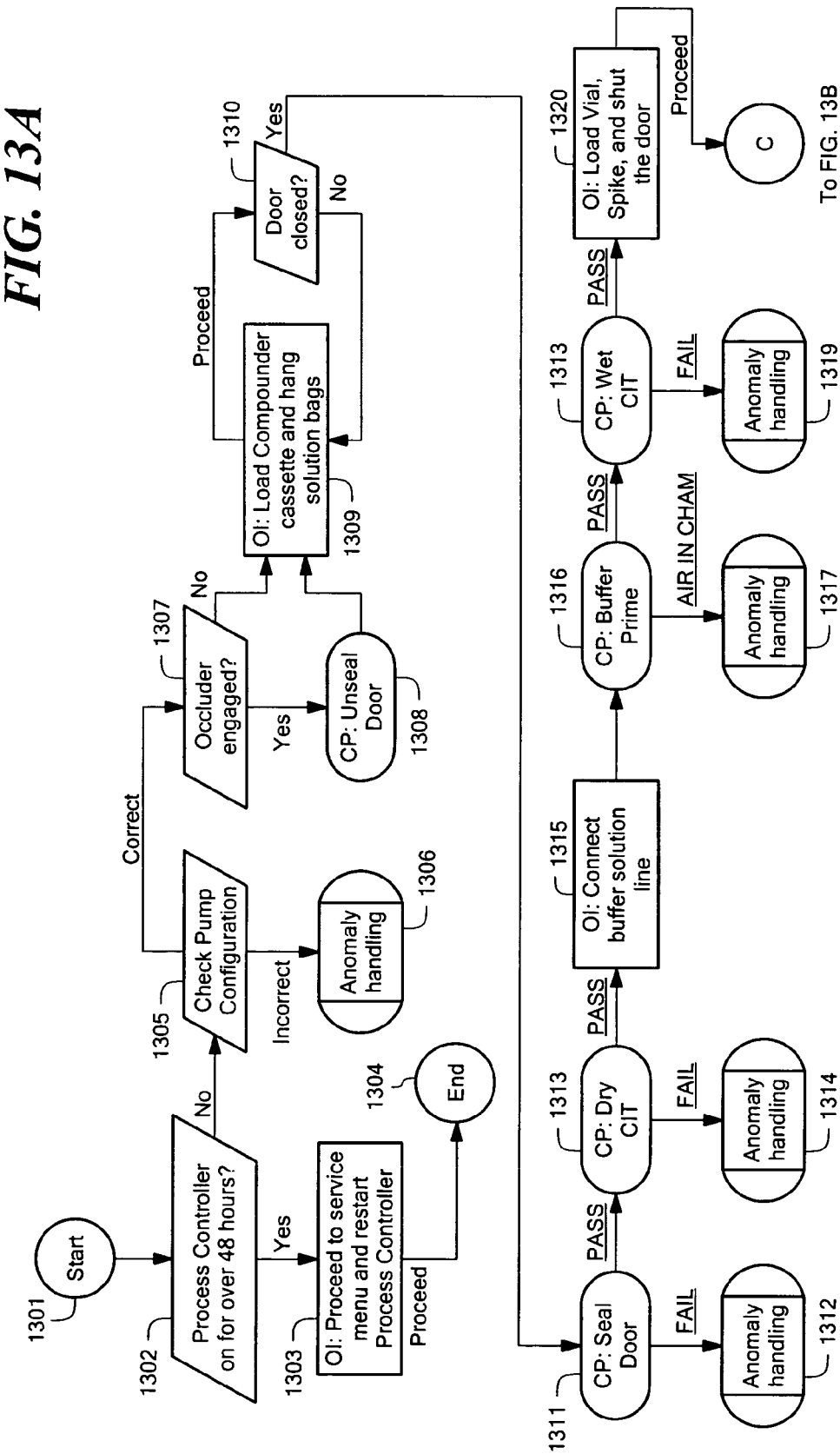
FIGS. 13A-B show a process flow diagram showing additional details of the compounding process shown in FIG. 12 in accordance with an embodiment of the present invention.
Figure 13B:
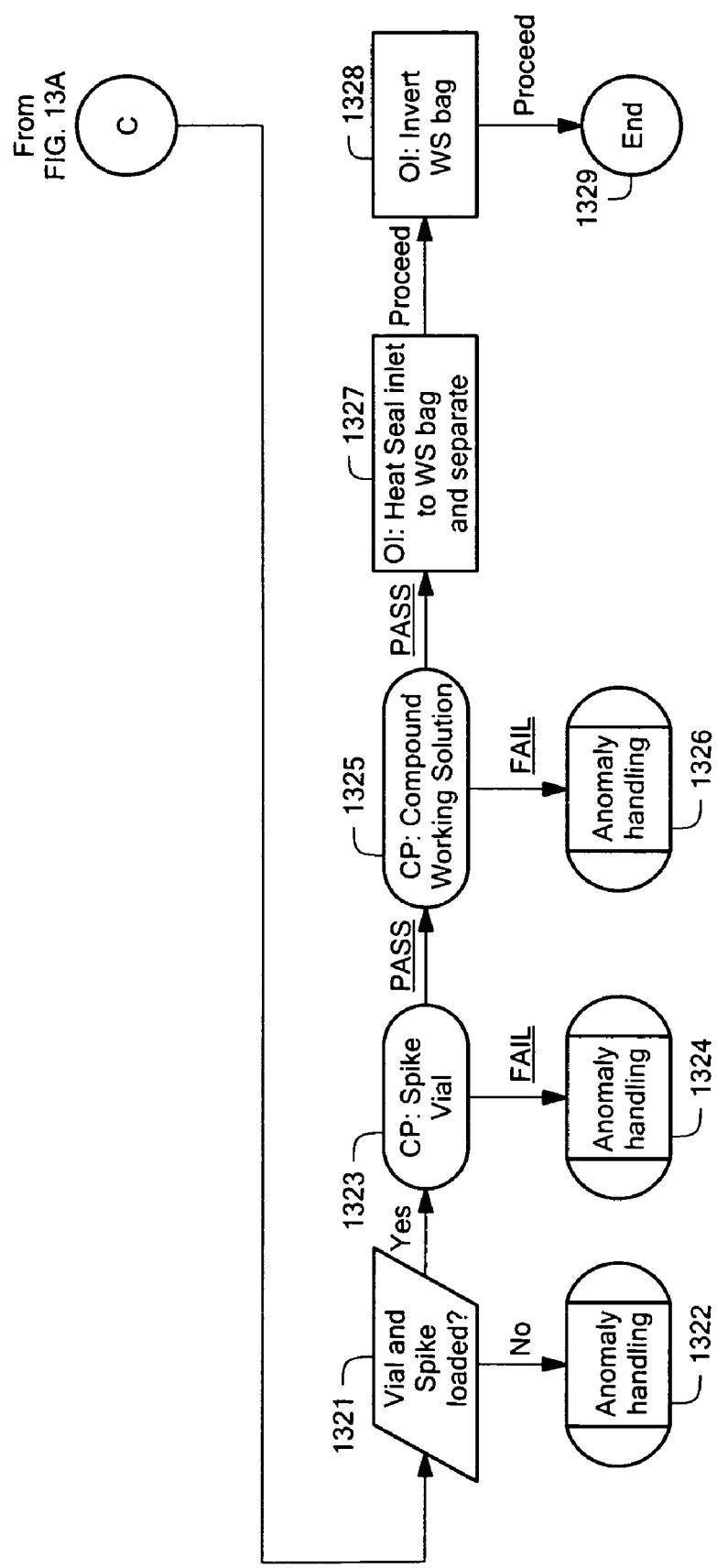

FIGS. 13A-B show a process flow diagram showing additional details of the compounding process in accordance with an embodiment of the present invention. The process begins in block 1301. A determination is made whether the process controller has been on for more than 48 hours, in block 1302. If so, then the process controller is restarted, in block 1303, which essentially ends this iteration of the process, in block 1304. If the process controller has not been on for more than 48 hours, then the pump configuration is checked, in block 1305. If the pump configuration is incorrect, then the process enters anomaly handling, in block 1306. If the pump configuration is correct, then a check is made as to whether the occluder is engaged, in block 1307. If the occluder is engaged, then the process controller instructs the compounder to unseal the door, in block 1308. The operator is then instructed to load the compounder cassette and hang the solution bags, in block 1309. When the door is confirmed to be closed, in block 1310, the process controller instructs the compounder to seal the door, in block 1311, which is done by inflating the bladder in the door assembly. If door sealing fails, then the process enters anomaly handling, in block 1312. If the door seals, then the process controller instructs the compounder to perform the dry CIT, in block 1313. If the dry CIT fails, then the process enters anomaly handling, in block 1314. If the dry CIT passes, then the process controller instructs the operator to connect the buffer solution line, in block 1315, and then instructs the compounder to prime, in block 1316. If priming fails, then the process enters anomaly handling, in block 1317. If priming is successful, then the process controller instructs the compounder to perform the wet CIT, in block 1318. If the wet CIT fails, then the process enters anomaly handling, in block 1319. If the wet CIT passes, then the process controller instructs the operator to load and lock the vial assembly and spike receptacle into the vial spike assembly, in block 1320. The process controller confirms that the vial assembly and spike receptacle are loaded and locked, in block 1321. If the vial assembly and spike receptacle cannot be loaded and locked, then the process enters anomaly handling, in block 1322. Upon confirmation that the vial assembly and spike receptacle are loaded and locked, then the process controller instructs the compounder to perform the spiking operation, in block 1323. If spiking fails, then the process enters anomaly handling, in block 1324. If spiking is successful, then the process controller instructs the compounder to perform the compounding operation, in block 1325. If the compounding operation fails, then the process enters anomaly handling, in block 1326. Upon successful completion of the compounding operation, the process controller instructs the operator to heat seal the buffer solution line, in block 1327, and perform other operations (such as clamping the lines leading to the spike receptacle). The process controller instructs the operator to invert the working solution bag, in block 1328. The process ends in block 1329.

Figure 14:
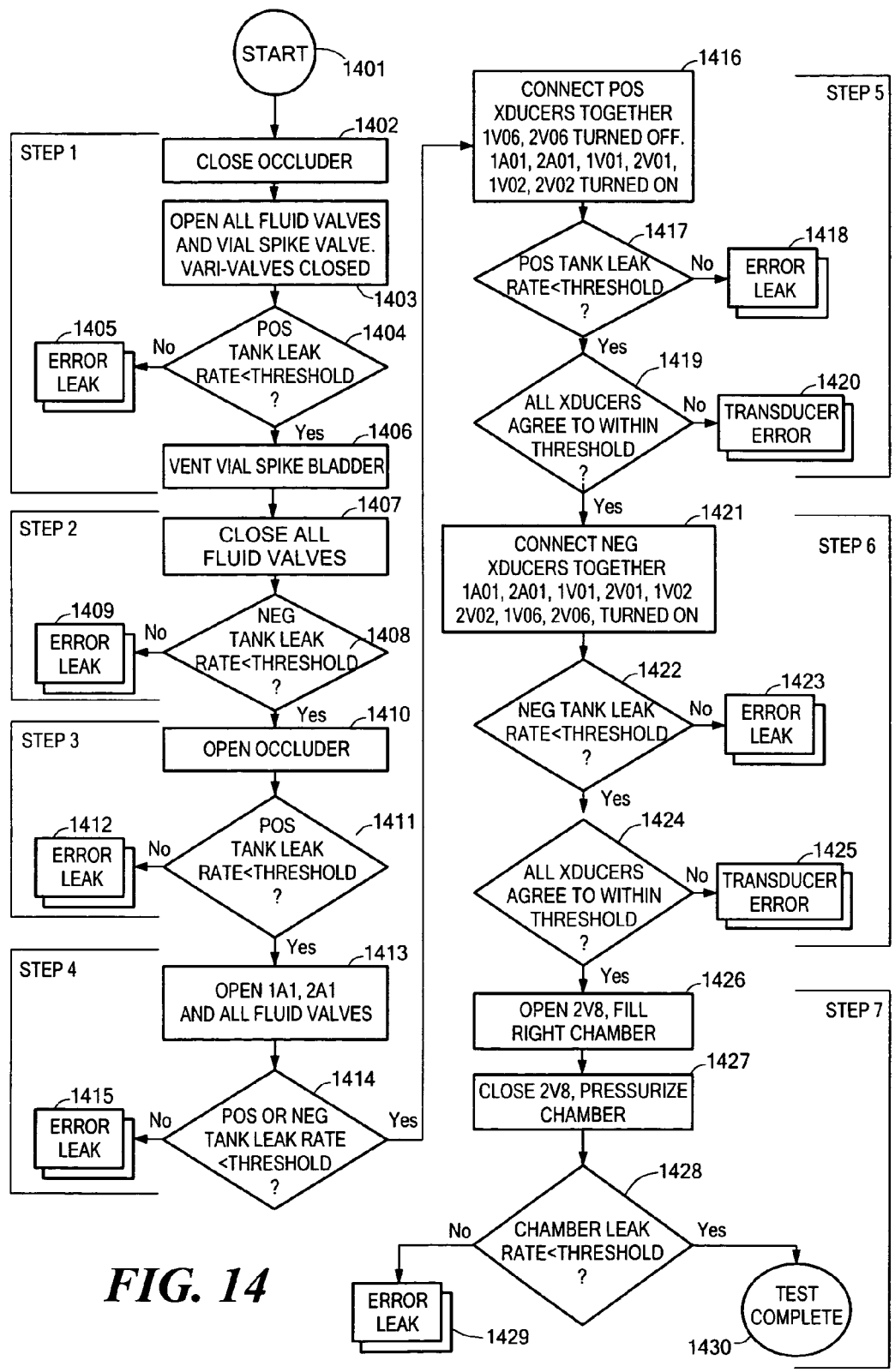
FIG. 14 shows a process flow diagram describing the compounder dry CIT process shown in FIGS. 12 and 13 in accordance with an embodiment of the present invention.

FIG. 14 shows a process flow diagram describing the compounder dry CIT process in accordance with an embodiment of the present invention. The dry CIT process begins in block 1401. The positive pneumatic system is first isolated from the cassette and a baseline leak rate for the positive assembly is obtained, specifically by closing the occluder, in block 1402, opening all fluid valves and vial spike valve and closing the variable valves, in block 1403, measuring the positive tank leak rate, in block 1404, venting the vial spike bladder if the positive tank leak rate is less than a predetermined threshold, and generating an error signal if the positive tank leak rate is greater than or equal to the predetermined threshold, in block 1405.

Then, the negative pneumatic system is isolated from the cassette and a baseline leak rate for the negative assembly is obtained, specifically by closing all fluid valves, in block 1407, measuring the positive tank leak rate, in block 1408, and generating an error signal if the negative tank leak rate is greater than or equal to a predetermined threshold, in block 1409.

Then, the process tests the cassette sheeting of the valves outside of the volcano valves, specifically by opening the occluder, in block 1410, measuring the positive tank leak rate, in block 1411, and generating an error signal if the positive tank leak rate is greater than or equal to a predetermined threshold, in block 1412.

Then, the process tests the cassette sheeting at the center of the volcano valves, specifically by opening valves 1A1 and 2A1 and all fluid valves, in block 1413, measuring the positive and negative tank leak rates, in block 1414, and generating an error signal if the positive or negative tank leak rate is greater than or equal to a predetermined threshold, in block 1415.

Then, the process verifies calibration of the positive transducers, specifically by isolating the positive transducers and connecting the positive transducers together, in block 1416, measuring the positive tank leak rate, in block 1417, generating an error signal if the positive tank leak rate is greater than or equal to a predetermined threshold, in block 1418, determining whether all positive transducers agree to within a predetermined threshold, in block 1419, and generating an error signal if the positive transducers do not agree to within a predetermined threshold, in block 1420.

Then, the process verifies calibration of the negative transducers, specifically by isolating the negative transducers and connecting the negative transducers together, in block 1421, measuring the negative tank leak rate, in block 1422, generating an error signal if the negative tank leak rate is greater than or equal to a predetermined threshold, in block 1423, determining whether all negative transducers agree to within a predetermined threshold, in block 1424, and generating an error signal if the negative transducers do not agree to within a predetermined threshold, in block 1425.

Finally, the process tests integrity of the fluid valve leading to the vent filter, specifically by filling the chamber, in block 1426, pressurizing the chamber, in block 1427, measuring the chamber leak rate, in block 1428, and generating an error signal if the chamber leak rate is greater than or equal a predetermined threshold, in block 1429. The dry CIT process ends in block 1430.

Figure 15:
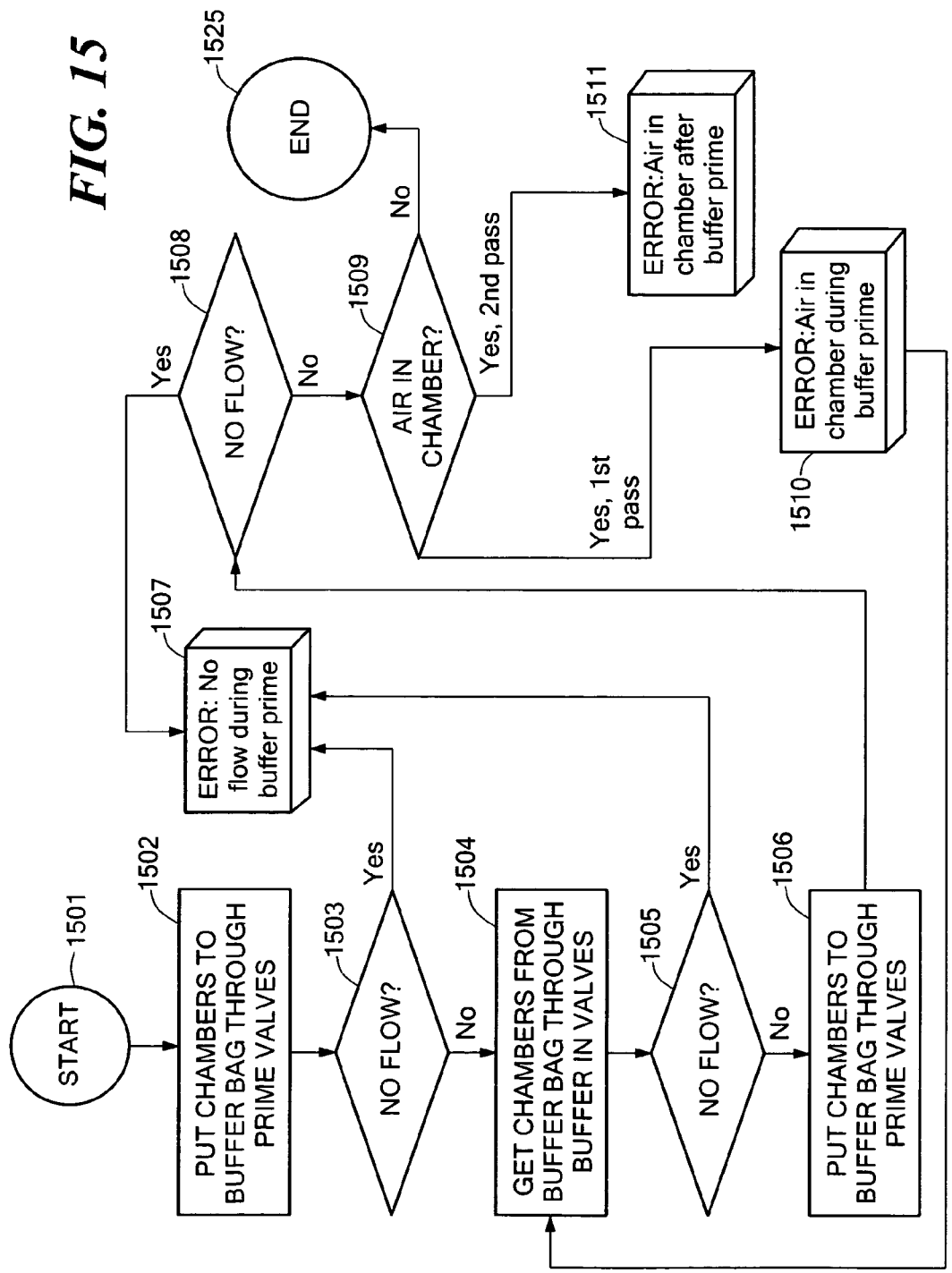
FIG. 15 shows a process flow diagram describing the compounder buffer solution priming process shown in FIGS. 12 and 13 in accordance with an embodiment of the present invention.

FIG. 15 shows a process flow diagram describing the compounder buffer solution priming process in accordance with an embodiment of the present invention. The priming process begins in block 1501. The process first puts the chambers to the buffer bag through prime valves, in block 1502, and attempts to draw buffer solution from the buffer bag, in block 1503. If there is no flow, then an error signal is generated, in block 1507. Assuming there is flow, the process then gets the chambers from the buffer bag through buffer in valves, in block 1504, and attempts to draw buffer solution from the buffer bag, in block 1505. If there is no flow, then an error signal is generated in block 1507. If there is flow, then the process puts the chambers to the buffer bag through prime valves, in block 1506, and attempts to draw buffer solution from the buffer bag, in block 1508. If there is no flow, then an error signal is generated, in block 1507. If there is flow, then the process checks for air in the chamber, in block 1509. If there is no air in the chamber, then the priming completes successfully in block 1525. If there is air in the chamber during this first pass, then this is considered an error condition, in block 1510, but the process recycles to block 1504 for a second pass. If, during the second pass, air is still detected in the chamber in block 1509, then an error signal is generated, in block 1511.

Figure 16:
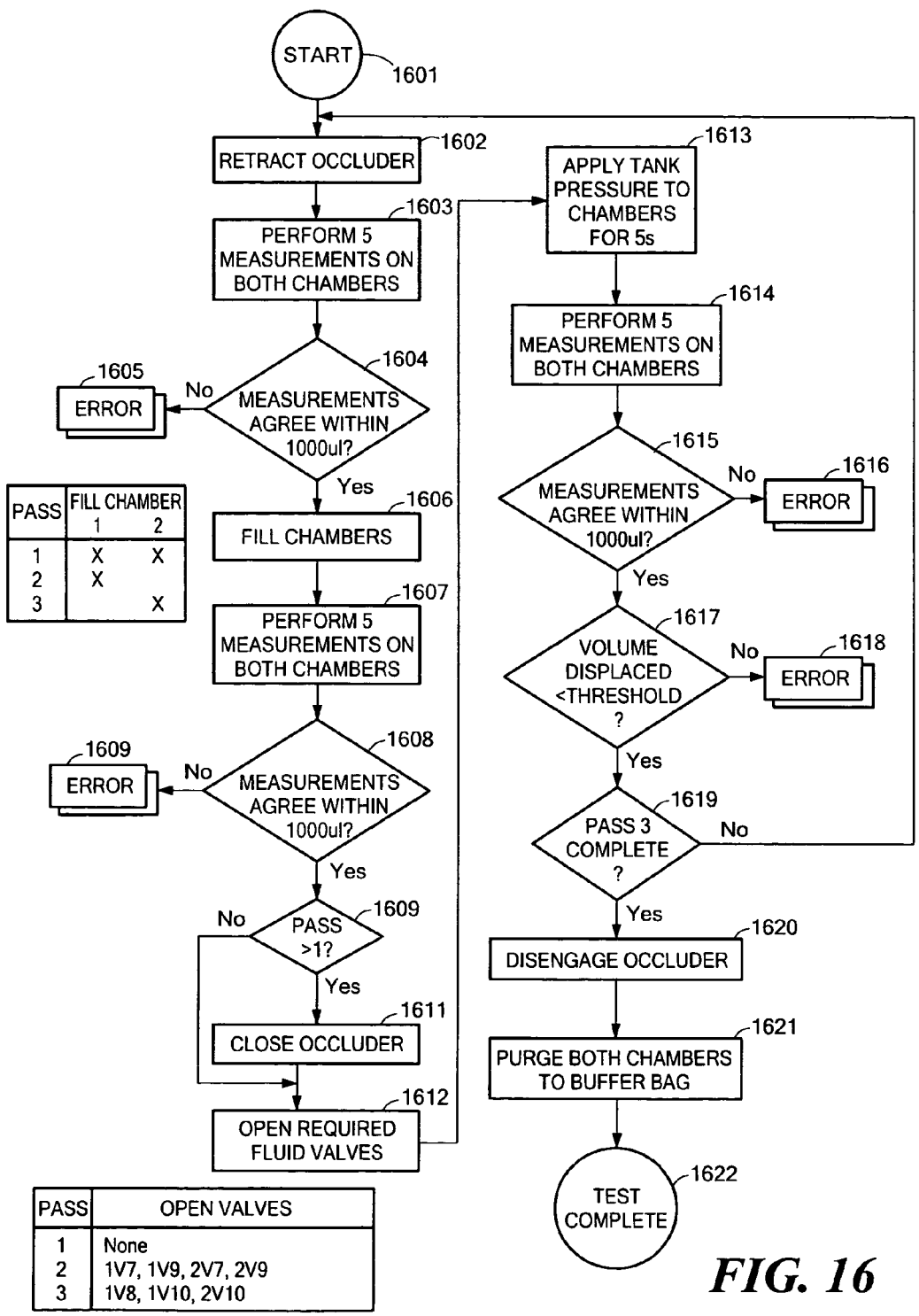
FIG. 16 shows a process flow diagram describing the compounder wet CIT process shown in FIGS. 12 and 13 in accordance with an embodiment of the present invention.

FIG. 16 shows a process flow diagram describing the compounder wet CIT process in accordance with an embodiment of the present invention. The wet CIT process begins in block 1601, and involves three passes of blocks 1602 through 1619. In each pass, the occluder is retracted, in block 1602, and various measurements are performed on both chambers, in block 1603. If the measurements are outside of a predetermined threshold (NO in block 1604), then an error signal is generated, in block 1605. Otherwise, a chamber filling operation is performed, in block 1606. During the first pass, both chambers are filled; during the second pass, only one chamber is filled; during the third pass, only the other chamber is filled. After the chamber filing operation, various measurements are performed on the chambers, in block 1607. If the measurements are outside of a predetermined threshold (NO in block 1608), then an error signal is generated, in block 1609. At this point, the occluder is left retracted during the first pass, but is closed during the second and third passes, in blocks 1610 and 1611. The required fluid valves are then opened, in block 1612, tank pressure is applied to the chambers for a predetermined amount of time, in block 1613, and various measurements are performed on the chambers, in block 1614. If the measurements are outside of a predetermined threshold (NO in block 1615), then an error signal is generated in block 1616. Otherwise, the process determines whether the volume displaced is within some threshold, in block 1617. If not, then an error signal is generated, in block 1618. After all three passes are complete, the occluder is disengaged, in block 1620, and both chambers are purged to the buffer solution bag, in block 1621. The process ends in block 1622.

Manual Teardown

During normal compounder teardown, the compounder receives commands from the process controller to release pressure against the pump door so that the door can be opened by the operator. The pressure against the door comes from both the door piston bladder and the tubing occluder. While the door piston bladder is pressurized and the tubing occluder is engaged, it is virtually impossible for the operator to open the pump door and remove the pump cassette. If communication between the process controller and the compounder is lost, then the operator will need to relieve this pressure manually in order to remove the cassette. Among other things, this involves the operator pressing the manual door release valve on the back of the pump to deflate the bladder in the door assembly. The operator may also manually retract the occluder if necessary.

Figure 17:
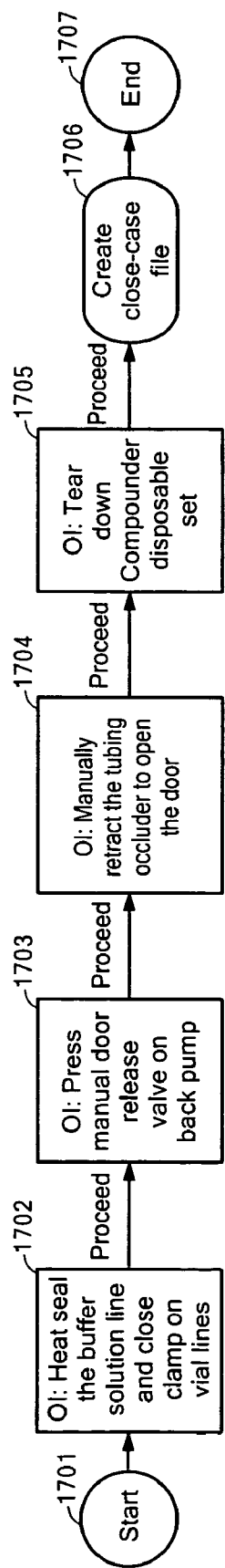
FIG. 17 shows a process flow diagram describing the process for manual compounder teardown in accordance with an embodiment of the present invention.

FIG. 17 shows a process flow diagram describing the process for manual compounder teardown in accordance with an embodiment of the present invention. The process begins in block 1701. The operator is instructed to heat seal the buffer solution line and close the clamps on the lines leading to the spike receptacle, in block 1702. The operator then presses the manual door release valve on the back of the pump to deflate the bladder in the door assembly, in block 1703. The operator then manually retracts the occulder if necessary to allow opening of the door, in block 1704. The operator then removes the compounder disposables, in block 1705. A close-case file is created indicating the failure, in block 1706. The process ends in block 1707.

Volumetric Calibration Check

The compounder is typically checked for calibration periodically to verify its ability to accurately measure volumes of pumped fluids. In exemplary embodiments of the invention, this calibration check is done by running test measurements with two different test cassettes having different but known chamber volumes.

Figure 18:
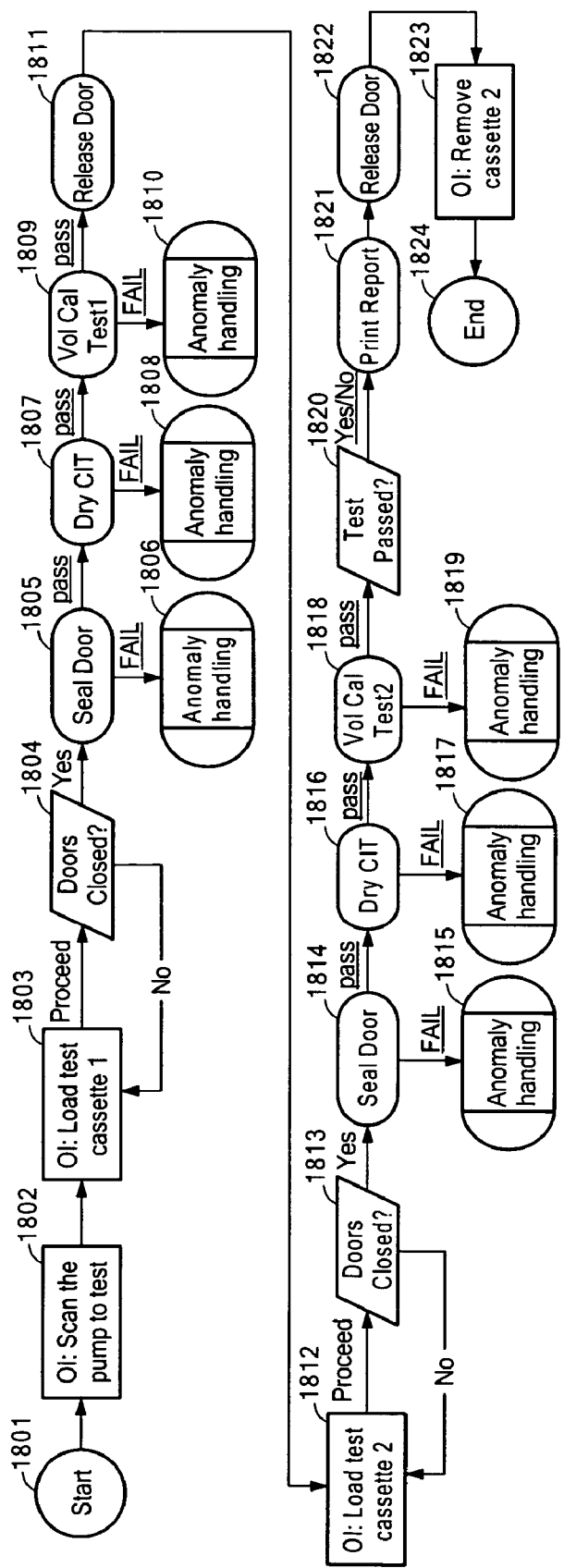
FIG. 18 shows a process flow diagram describing the compounder volumetric calibration process in accordance with an embodiment of the present invention.

FIG. 18 shows a process flow diagram describing the volumetric calibration check process in accordance with an embodiment of the present invention. The process begins in block 1801. The operator is instructed to scan a bar code on the compounder in block 1802 in order to test the compounder. The operator is then instructed to load the first test cassette, in block 1803. Upon confirmation that the door is closed, in block 1804, the door is sealed, in block 1805. If the door fails to seal properly, then the process enters anomaly handling, in block 1806. If the door seals properly, a dry CIT is run, in block 1807. If the dry CIT fails, then the process enters anomaly handling, in block 1808. If the dry CIT passes, then a volume calibration test is run to measure the volume of the chambers, in block 1809. If the difference between the measured volume and the known volume of the first cassette is greater than or equal to some predetermined threshold, then the process enters anomaly handling, in block 1810. Otherwise, the door is released, in block 1811, and the operator is instructed to load the second test cassette, in block 1812. Upon confirmation that the door is closed, in block 1813, the door is sealed, in block 1814. If the door fails to seal properly, then the process enters anomaly handling, in block 1815. If the door seals properly, a dry CIT is run, in block 1816. If the dry CIT fails, then the process enters anomaly handling, in block 1817. If the dry CIT passes, then a volume calibration test is run to measure the volume of the chambers, in block 1818. If the difference between the measured volume and the known volume of the second cassette is greater than or equal to some predetermined threshold, then the process enters anomaly handling, in block 1819. Otherwise, a test pass determination is made, in block 1820, and a report is printed, in block 1821. The door is released, in block 1822, and the operator is instructed to remove the second test cassette, in block 1823. The process ends in block 1824.

It should also be noted that the flow diagrams are used herein to demonstrate various aspects of the invention, and should not be construed to limit the present invention to any particular flow or implementation. In some cases, certain process steps can be omitted or performed in a different order than shown without changing the overall results or otherwise departing from the true scope of the invention.

The present invention may be embodied in other specific forms without departing from the true scope of the invention. The described embodiments are to be considered in all respects only as illustrative and not restrictive.

What is claimed is:

1. An apparatus for mixing a substance in a sealed container with a liquid, the container being positioned in a container receptacle, the container receptacle configured to couple with a port assembly to permit liquid to enter the container through the port assembly, the apparatus comprising:
   a container spiking assembly comprising a movable member adapted to move the container receptacle toward the port assembly;
   a container spiking assembly controller in communication with the container spiking assembly for controlling coupling of the container receptacle with the port assembly; and
   a liquid controller for controlling the flow of the liquid through the port assembly into the container to produce a combined substance and liquid, wherein:
   the container spiking assembly controller is configured to control the movement of the movable member of the container spiking assembly to couple the container receptacle with the port assembly while the port assembly is immobilized relative to the container receptacle, and wherein upon coupling, the container receptacle and port assembly are configured to lock together through engagement of one or more engagement teeth between the container receptacle and the port assembly.

2. The apparatus as defined by claim 1 wherein the liquid controller also controls the flow of combined substance and liquid from the container.

3. The apparatus as defined by claim 1 wherein the container spiking assembly controller includes logic for determining the relative locations of the container receptacle and the port assembly, using input from at least one sensor associated with the container spiking assembly.

4. The apparatus as defined by claim 1 wherein the container spiking assembly further comprises a cover capable of being in either an open position or a closed position, the cover securing the container receptacle and port assembly within the container spiking assembly when in the closed position, and the container spiking assembly controller having logic for determining if the cover is in the closed position.

5. The apparatus as defined by claim 4 wherein the container spiking assembly controller includes logic to direct the container receptacle to couple with the port assembly after detecting that the cover is in the closed position.

6. The apparatus as defined by claim 4 further including a cover lock that prevents the cover from being moved from the closed position while the liquid is being received by the container.

7. The apparatus as defined by claim 1 further including a pneumatically controlled member within the container spiking assembly, the pneumatically controlled member capable of contributing to the coupling of the container receptacle with the port assembly in response to input from the container spiking assembly controller.

8. The apparatus as defined by claim 1 wherein the liquid controller includes stored commands for directing the delivery of a predetermined amount of liquid to the container via the port assembly.

9. The apparatus as defined by claim 1 further comprising a housing containing at least one of the container spiking assembly controller and the liquid controller.

10. The apparatus as defined by claim 9 wherein the container spiking assembly at least partially extends outwardly from the housing.

11. The apparatus as defined by claim 1 further comprising a sensor within the container spiking assembly for detecting the location of the container relative to the port assembly.

12. The apparatus as defined by claim 1 wherein the container spiking assembly is configured to contain the container receptacle in a single orientation.

13. The apparatus as defined by claim 1 further comprising a set of valves controlled by the liquid controller to control the flow of liquid into the container.

14. The apparatus as defined by claim 1 further comprising a pump chamber used by the liquid controller to measure the volume of the liquid to be directed to the container.

15. The apparatus as defined by claim 1 wherein the substance is a caustic solution.

16. The apparatus as defined by claim 1 wherein the substance is an anti-pathogen compound.

17. The apparatus as defined by claim 1, wherein the container receptacle comprises a plurality of engagement teeth, and wherein a locking feature on the port assembly engages one or more of the plurality of engagement teeth.

18. The apparatus as defined by claim 17, wherein the container receptacle includes a plurality of tabs, each tab having engagement teeth, wherein the engagement teeth on adjacent tabs are staggered relative to one another.

19. The apparatus as defined by claim 18, wherein the engagement teeth are staggered by approximately half the height of one of the engagement teeth.

20. The apparatus defined by claim 11, wherein the container receptacle comprises at least one raised switch engagement feature on an outer surface of the container receptacle for operating a sensor within the container spiking assembly.

21. An apparatus for mixing a substance in a sealed container with a liquid, the container being positioned in a container receptacle, the container receptacle configured to couple with a port assembly to permit liquid to enter the container through the port assembly the apparatus comprising:
    positioning means for moving the container receptacle toward the port assembly;
    coupling means for controlling coupling of the container receptacle with the port assembly; and
    flow means for controlling the flow of the liquid into the container to produce a combined substance and liquid, wherein:
    the positioning means is configured for movement of the container receptacle toward the port assembly while the port assembly is immobilized relative to the container receptacle, and wherein upon coupling, the container receptacle and port assembly are configured to lock together through engagement of one or more engagement teeth between the container receptacle and the port assembly.

22. The apparatus as defined by claim 21 wherein the flow means also controls the flow of combined substance and liquid from the container.

23. The apparatus as defined by claim 21 wherein the coupling means includes means for determining the relative locations of the container receptacle and the port assembly, using input from at least one sensor associated with the positioning means.

24. The apparatus as defined by claim 21 wherein the positioning means includes a cover capable of being in either an open position or a closed position, the cover securing the container receptacle and port assembly within the positioning means when in the closed position, and the coupling means having means for determining if the cover is in the closed position.

25. The apparatus as defined by claim 24 wherein the coupling means includes logic to direct the container receptacle to couple with the port assembly after detecting that the cover is in the closed position.

26. The apparatus as defined by claim 24 further including a cover lock that prevents the cover from being moved from the closed position while the liquid is being received by the container.

27. The apparatus as defined by claim 21 further including a pneumatically controlled means within the positioning means, the pneumatically controlled means capable of contributing to the coupling of the container receptacle with the port assembly in response to input from the coupling means.

28. The apparatus as defined by claim 21 wherein the flow means includes means for controlling the delivery of a predetermined amount of liquid to the container via the port assembly.

29. The apparatus as defined by claim 21 further comprising a housing containing at least one of the coupling means and the flow means.

30. The apparatus as defined by claim 29 wherein the positioning means at least partially extends outwardly from the housing.

31. The apparatus as defined by claim 21 further comprising a means for detecting the location of the container relative to the port assembly.

32. The apparatus as defined by claim 21 wherein the positioning means is configured to contain the container receptacle in a single orientation.

33. The apparatus as defined by claim 21 further comprising a set of valves controlled by the flow means to control the flow of liquid into the container.

34. The apparatus as defined by claim 21 further comprising a means for measuring the volume of the liquid to be directed to the container, the measuring means being used by the flow means.

35. The apparatus as defined by claim 21 wherein the substance is a caustic substance.

36. The apparatus as defined by claim 21 wherein the substance is an anti-pathogen compound.

37. The apparatus as defined by claim 1 wherein the container spiking assembly has a cover for securing the port assembly within the container spiking assembly, and wherein the container spiking assembly controller is configured to control the movement of the container within the container spiking assembly so as to connect the container with a fluid flow lumen of the port assembly.

38. The apparatus is defined by claim 7 further including an inflatable bladder in communication with the pneumatically controlled member for pneumatic control of the pneumatically controlled member in response to input from the container spiking assembly controller.

39. The apparatus as defined by claim 21 wherein the positioning means is cylindrical.

40. The apparatus as defined by claim 21 wherein positioning means includes means for securing the port assembly and wherein the coupling means includes means for moving the container so as to couple the container with a fluid flow lumen of the port assembly.

41. The apparatus as defined by claim 27 wherein the pneumatically controlled means includes a pneumatically controlled member and an inflatable means in communication with the pneumatically controlled member for pneumatic control of the pneumatically controlled member in response to input from the coupling means.

* * * * *